United States Patent [19]
Cornsweet et al.

[11] Patent Number: 4,715,703
[45] Date of Patent: Dec. 29, 1987

[54] OCULAR-FUNDUS ANALYZER

[75] Inventors: Tom N. Cornsweet; Samuel Hersh, both of Mission Viejo, Calif.

[73] Assignee: Rodenstock Instrument Corporation, Los Angeles, Calif.

[21] Appl. No.: 818,913

[22] Filed: Jan. 14, 1986

Related U.S. Application Data

[63] Continuation of Ser. No. 433,813, Oct. 12, 1982, abandoned.

[51] Int. Cl.[4] .......................... A61B 3/10; A61B 3/14
[52] U.S. Cl. .................................. 351/205; 351/206; 351/208; 351/214
[58] Field of Search ............... 351/205, 206, 207, 209, 351/214; 354/62

[56] References Cited

U.S. PATENT DOCUMENTS

| | | | |
|---|---|---|---|
| 3,533,342 | 10/1970 | McMillin | 351/206 |
| 3,664,730 | 5/1972 | Cardona | 351/205 |
| 4,252,420 | 2/1981 | Kohayakawa | 351/206 |
| 4,370,333 | 1/1983 | Kani et al. | 351/206 |
| 4,405,215 | 9/1983 | Sano et al. | 351/208 |
| 4,436,389 | 3/1984 | Sano | 351/208 |

Primary Examiner—Rodney B. Bovernick
Attorney, Agent, or Firm—Paul M. Craig

[57] ABSTRACT

An apparatus for examining the ocular fundus of an eye, in which an illuminating device is provided with non-overlapping apertures positioned substantially side by side, and in which an image of the apertures is formed on a part of the ocular fundus; an image of the illuminated ocular fundus is formed in a detecting plane in response to reflection from this fundus in such a manner as to provide a stereo pair of images of the ocular fundus in the detecting plane which are detected and then electronically processed and digitally analyzed thereby to display information about the ocular fundus under examination; the pupil position is also detected and the eye is then automatically aligned relative to the optical axis of the image, at least part of which is common to the axis of the illuminating device.

24 Claims, 9 Drawing Figures

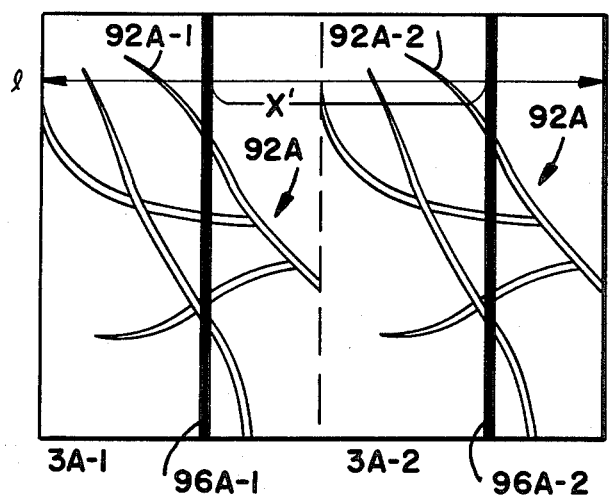
FIG _ 3A
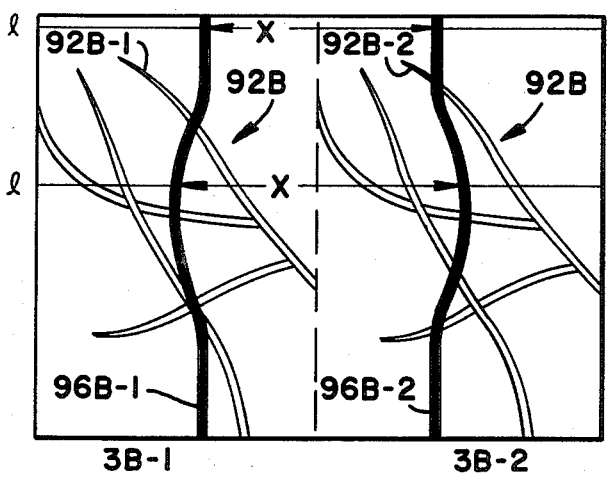
FIG _ 3B
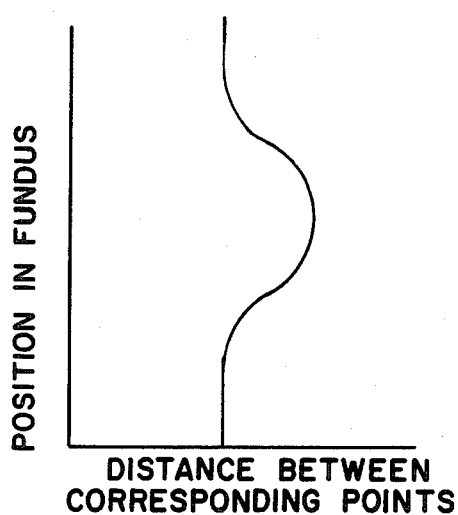
FIG _ 3C

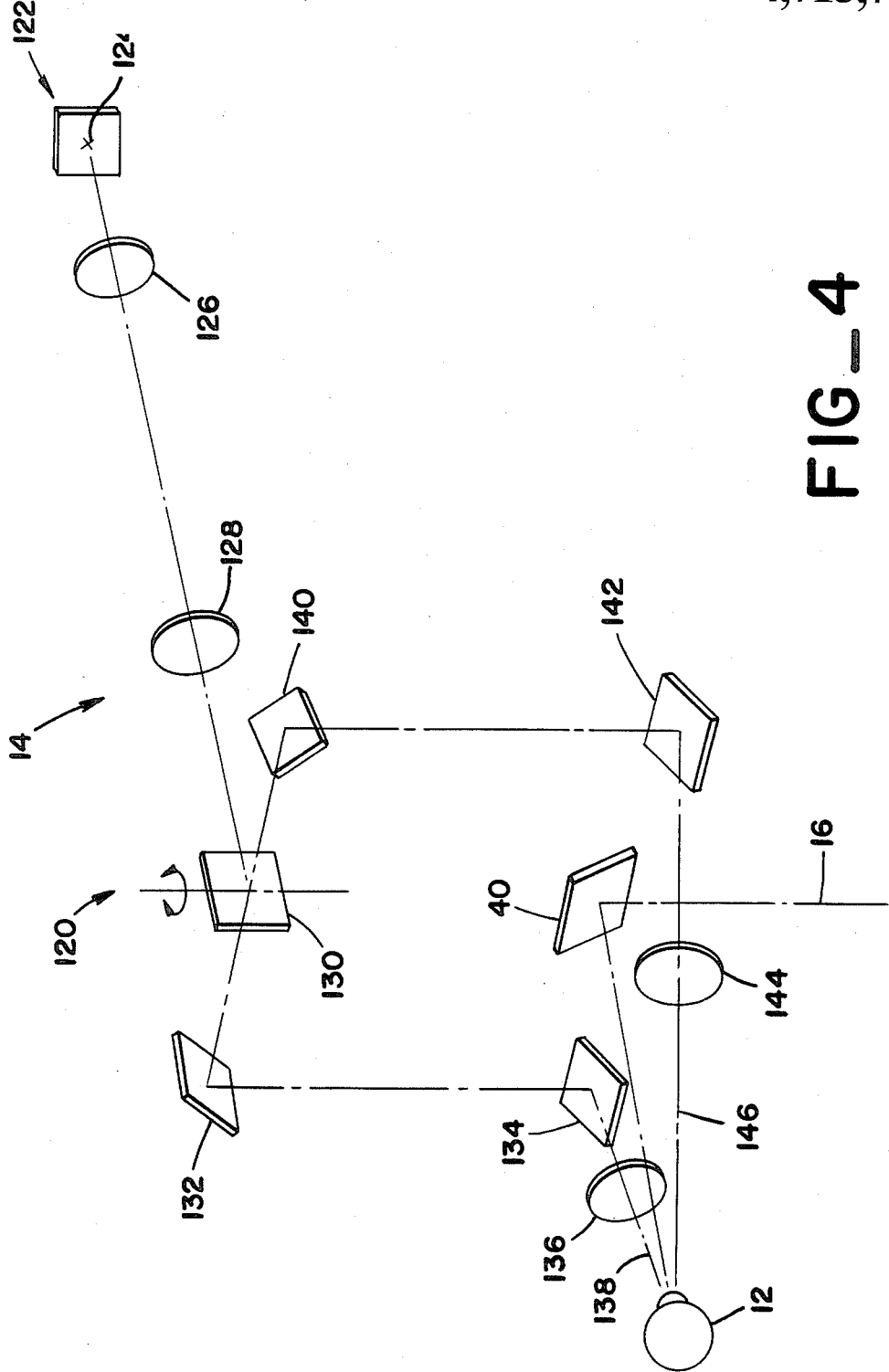
FIG_4

FIG_6

OCULAR-FUNDUS ANALYZER

This is a continuation of application Ser. No. 433,813 filed Oct. 12, 1982, now abandoned.

TECHNICAL FIELD

This invention relates to apparatus for examining the ocular fundus of the eye and, more particularly, to an optoelectronic ocular fundus analyzer.

BACKGROUND ART

Many disorders of the eye, a common one of which is glaucoma, cause changes in the color and/or shape of regions of the surface lining the inside of the eyeball, which is the ocular fundus. Other disorders of the entire body, such as diabetes and atherosclerosis, also produce such changes in the ocular fundus. These changes usually occur at the early stages of the disorders, and often the disorders are first detected during an examination of the ocular fundus known as a fundoscopic examination.

The detection of disorders by the fundoscopic examination may be divided into three aspects. These are (1) detection of abnormalities or changes in the color of regions of the ocular fundus, (2) detection of abnormalities or changes in the two dimensional shape of regions of the ocular fundus, e.g., changes in the tortuosity of fundus blood vessels that occur in atherosclerosis or changes in the size of a discolored region, and (3) detection of abnormalities or changes in the third dimension of regions of the ocular fundus, i.e., along the optic axis or visual axis of the eye.

Abnormal color of a region of the ocular fundus is a consequence of physical abnormalities in the fundus that cause the region to reflect light abnormally. For example, the leakage of certain chemicals from the blood into the tissue of the fundus can change the chemical composition of the region. Therefore, the way in which the region interacts with light may be changed so that, for example, a greater fraction of long wavelength light and a smaller fraction of short wavelength light are reflected. If so, the region will appear abnormally more red.

As another example, there are regions of the ocular fundus that should normally appear reddish. These regions constitute a white surface, i.e., a surface that reflects equally most wavelengths of the visible spectrum, overlaid by a fine mesh of tiny blood vessels which circulate blood, i.e., a substance that reflects long wavelength light much more strongly than short wavelength light. Abnormal color of these regions may be a consequence of impaired blood circulation. If so, if illuminated with white light, these regions will appear abnormally more white and exhibit pallor.

Various ophthalmological instruments have been developed to examine the ocular fundus to detect abnormal color, as well as changes in the two-dimensional and three-dimensional shape of the fundus. One instrument, called an ophthalmoscope, illuminates the inside of a patient's eye and provides an optical path for the physician to see the fundus. The physician relies on his own or subjective color vision to detect subtle abnormalities in the color of the fundus. This is neither highly accurate nor objective since the physician cannot visually determine the amount or intensity of light being reflected at each wavelength, which is data that provide more subtle color information. Furthermore, because many disorders are detected or their treatments monitored by evaluating changes in the fundus over time, the physician using the ophthalmoscope may have to depend either on her memory or her sketches of the appearance of the fundus. The same problems occur when evaluating changes in the two-dimensional and three-dimensional shapes of the fundus.

Another instrument is a special camera called a fundus camera that is used to photograph the ocular fundus. A series of black and white photographs can be taken with the fundus camera using light at various wavelengths. In essence, the series of photographs taken at different wavelengths represent a set of "reflectance spectra", that is, they represent the amount of light reflected from each point in the picture at each wavelength. Then, the photographs are compared visually or with a densitometer. While the reflectance spectrum is more objective data than can be obtained using the ophthalmoscope, this photographic procedure is awkward and suffers seriously from the fact that slight variations in the conditions under which the black and white film is developed can cause significant changes in the resulting photographic densities.

Also, the fundus camera can be used to take photographs over time. While these photographs provide better and more objective data than the above-mentioned sketches for detecting changes in color, as well as shape, the variability of the conditions of illumination, and especially of the chemistry of the photographic film processing, makes accurate measures of change difficult.

Furthermore, and with respect to abnormalities in the three-dimensional shape of the ocular fundus, during the course of, for example, undetected or uncontrolled glaucoma, a region of the ocular fundus called the optic disk develops cupping or excavation. That is, the surface of the optic disk recedes from the front of the eye. On the other hand, brain tumors, for example, can cause the optic disk to bulge toward the front of the eye, as can fundus tumors.

The three-dimensional shape and changes in this shape of the fundus are very difficult to evaluate with the two-dimensional photographs taken with the standard fundus camera. A modified fundus camera has been used that produces stereo pairs of fundus photographs. When viewed with a stereo viewer, these stereo pictures provide better data on which to evaluate the three-dimensional shape of the optic disk. However, the evaluation is essentially visual and subjective and, therefore, not highly accurate.

SUMMARY OF THE INVENTION

It is an object of the present invention to provide a novel apparatus for examining the ocular fundus of the eye.

It is another object of the present invention to provide an ocular fundus examination apparatus for objectively determining eye disorders.

Yet another object of the present invention is to provide objective, highly accurate and quantitative data having information about the ocular fundus.

Still another object of the present invention is to utilize state-of-the-art optoelectronics for the novel ocular fundus examining apparatus.

These and other objects of the present invention are obtained through the use of apparatus for examining the ocular fundus of the eye, including means for illuminating the ocular fundus, means, responsive to the light reflected by the ocular fundus, for forming an image of the ocular fundus at a detecting plane, means for sensing and scanning the image of the ocular fundus at the detecting plane, and data processing means, coupled to said sensing and scanning means, for storing digitally and displaying data about the ocular fundus.

The light that illuminates and is reflected by the ocular fundus forms an image of the fundus at the detecting plane. The sensing and scanning means can be, for example, a TV camera receiving the image as a picture which is then scanned. The output data of the camera are then digitized, stored and processed by the data processing means. The optical and digital data that are obtained constitute objective, highly accurate and quantitative information about the ocular fundus, including information about the color, two-dimensional shape and three-dimensional shape of the fundus, as well as changes in these parameters.

BRIEF DESCRIPTION OF THE DRAWINGS

FIG. 3A and FIG. 3B are stereo images of a region of the ocular fundus providing data about the three-dimensional shape of the fundus.

FIG. 3C is a depth profile of a region of the ocular fundus obtained from the optical data of FIG. 3B.

FIG. 4 shows schematically an optical system used in conjunction with the optical system of FIG. 1.

DETAILED DESCRIPTION OF THE INVENTION

Figure 1:
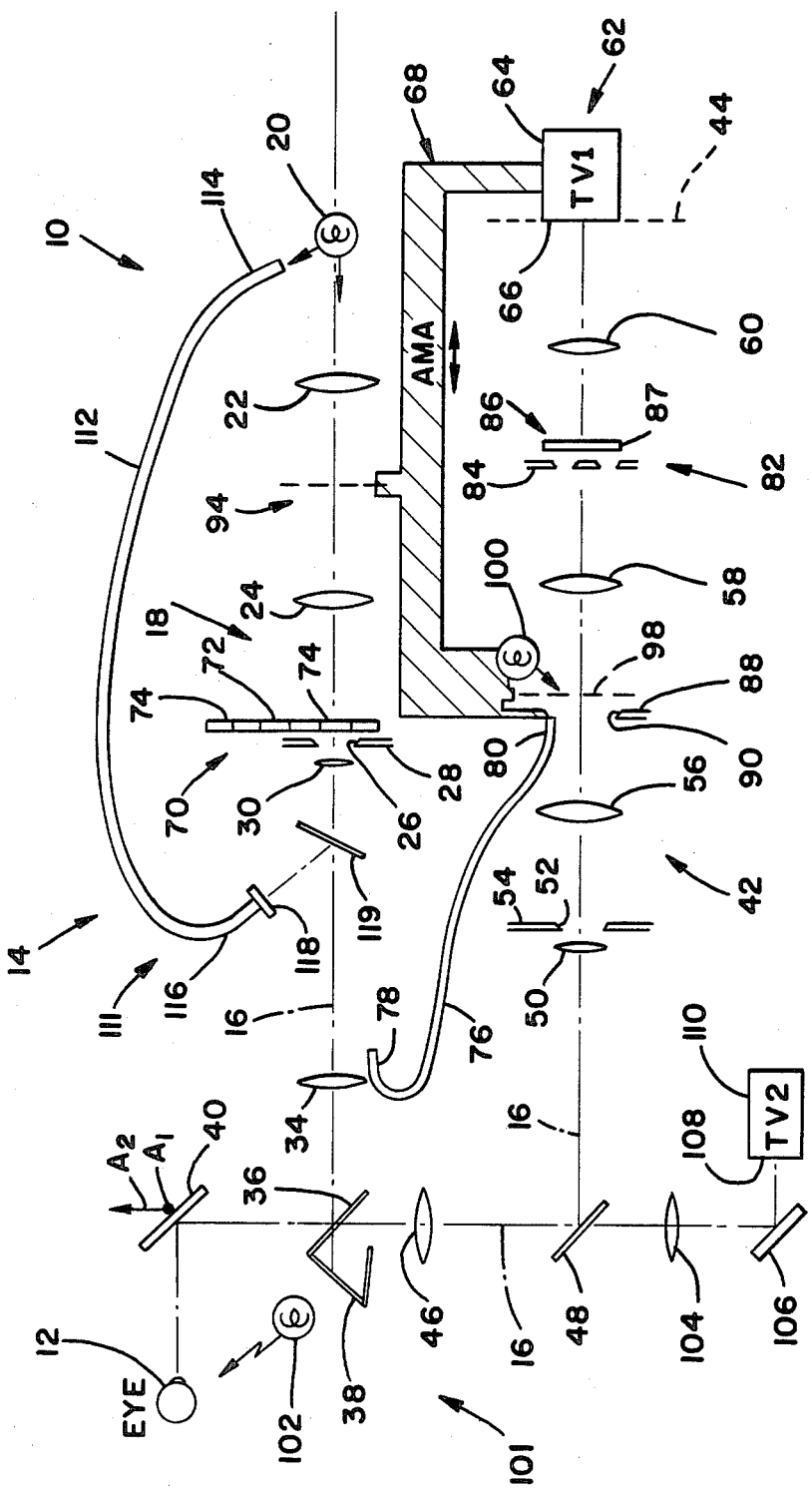
FIG. 1 is a schematic side view illustration of an optical system of the present invention.

FIG. 1 illustrates a portion of an apparatus or instrument 10 used to examine the ocular fundus of an eye 12. In particular, the portion shown in FIG. 1 is an optical system 14 having an optical axis 16 and used to acquire optical data for examining the fundus. While the optical components are shown in full lines in FIG. 1, it will become appreciated that several of these are used or introduced into the optical system 14 to carry out particular modes of operation.

The optical system 14 includes a subsystem 18 for illuminating the ocular fundus of the eye 12. Subsystem 18 has a light source 20 whose light passes through a lens 22 and a lens 24. Lenses 22 and 24 form an image of the light source 20 at a circular aperture 26 provided by a mask 28.

Light from aperture 26 then propagates through a lens 30 and a lens 34 to a beam splitter 36. Half of the light then passes through beam splitter 36 and is absorbed by a light trap 38 and the other half of the light is reflected by the beam splitter 36 onto a movable mirror 40 which then reflects the light into the eye 12. Lenses 30 and 34 form an image of aperture 26 in the plane of the pupil of the eye 12, and the light then passes through the pupil and falls on the ocular fundus, illuminating it. Mirror 40 is rotatable about a horizontal axis A1 and a vertical axis A2 for optical alignment reasons to be described.

Optical system 14 has another subsystem 42 for forming an image of the ocular fundus at a detecting plane 44. Subsystem 42 includes the mirror 40 which receives some of the light reflected by the ocular fundus outside the eye 12 and reflects the light towards the beam splitter 36. Half the light is then reflected by the beam splitter 36 towards the source 20 and is lost, but the other half passes through the beam splitter 36 and a lens 46 towards a cold mirror 48. The light is then reflected by cold mirror 48 through a lens 50 towards a circular aperture 52 provided by a mask 54. Lens 46 and lens 50 form an image of the pupil of the eye 12 in the plane of aperture 52. The diameter of aperture 52 is smaller than the image of the typical pupil to prevent any light that might be reflected from the iris of the eye 12 from propagating along the remainder of subsystem 42.

The light passing through aperture 52 is then propagated by a lens 56, a lens 58 and a lens 60 onto the detecting plane 44. Lenses 46, 50, 56, 58 and 60, in combination with the optics of the eye 12, form an image of the ocular fundus at the detecting plane 44.

Also shown in FIG. 1 is an apparatus 62 for sensing and scanning the image of the fundus. For example, apparatus 62 can be a TV camera 64 whose screen 66 is at the detecting plane 44 to receive the image. Thus, the image or a picture of the fundus is on the screen 66 which senses the light falling on it. TV camera 64 is supported on an axial motion assembly 68 in such a way that screen 66 can be moved toward or away from lens 60 to bring the image of the fundus in sharp focus should the eye 12 exhibit a refractive error. For example, if the patient is nearsighted, the camera 64 can be moved toward the lens 60 to focus the image on screen 66.

In summary, thus far, light from source 20 illuminates the fundus, and light reflected from the fundus forms an image or picture of the fundus on screen 66. As will be described below, the picture can then be scanned, digitized and stored for processing. Any number of scans or pictures can be taken, either at one examination or over a period of time, the latter to aid in detecting changes in the fundus.

To obtain objective optical data about the color of the fundus, optical system 14 has a subsystem 70 for filtering the light from source 20. Subsystem 70 can be a rotatable wheel 72 having a plurality of different light filters 74, any one of which can be rotated into the path of the light along the optical axis 16. As will be further described, two or more pictures of the fundus can be taken under different illuminating wavelengths, i.e., with two or more different filters 74, to provide data from which a reflectance spectrum of the fundus can be determined. The wheel 72 can support an aperture in lieu of one of the filters 74 to transmit unfiltered light should color information not be required.

To provide highly accurate reflectance spectrum data about the fundus, differences in the sensitivity of the TV camera 64 to different wavelengths preferably should be taken into account. Therefore, subsystem 70 can include a fiber optic bundle 76 having one end 78 located near lens 34 to intercept a small amount of light that is filtered by filters 74 and that is illuminating the fundus. The other end 80 of fiber optic bundle 76 is positioned as shown so that light entering end 78 and exiting end 80 forms a small bright spot on a corner of screen 66 after being propagated by lens 58 and lens 60. Consequently, the level or intensity of the video signal corresponding to this bright spot on screen 66, for each fundus picture taken with a different filter 74, provides data about the sensitivity of camera 64 to different wavelengths.

The optical system 14 can include another subsystem 82 to obtain data at the detecting plane 44 having three-dimensional or depth information about the ocular fundus. This subsystem 82 includes an aperture mask 84 and a prism 86 shown in more detail in FIG. 2 to which reference is now made. Mask 84 has two semicircular apertures 84a, 84b positioned side-by-side, as shown. Prism 86 is, for example, a bi-prism 87, constituting two wedge prisms 87a, 87b connected base-to-base. Light in one path passing through aperture 84a is deviated horizontally by wedge prism 87a in one direction from the optical axis 16 and light in the other path passing through the other aperture 84b is deviated horizontally by the other prism 87b in the other direction from the optical axis 16, i.e., the light is spatially separated by prism 86.

Lenses 46, 50, 56 and 58 combine to form an image of the patient's pupil in the plane 84. Therefore, the light in one of the paths forms an image of the region of the fundus under examination as if it were viewed through one side of the pupil and the light in the other path forms an image of the same region of the fundus as if it were viewed through the other side of the pupil. These two images form a stereo pair or picture of this region of the fundus on screen 66 as shown, for example, and as will be further described, in FIG. 3A-1. and FIG. 3A-2. Also shown in FIG. 1 as part of subsystem 82 is a mask 88 which has a rectangular aperture 90 whose horizontal width is designed to block those portions of the stereo pair that would overlap on screen 66.

Figure 2:
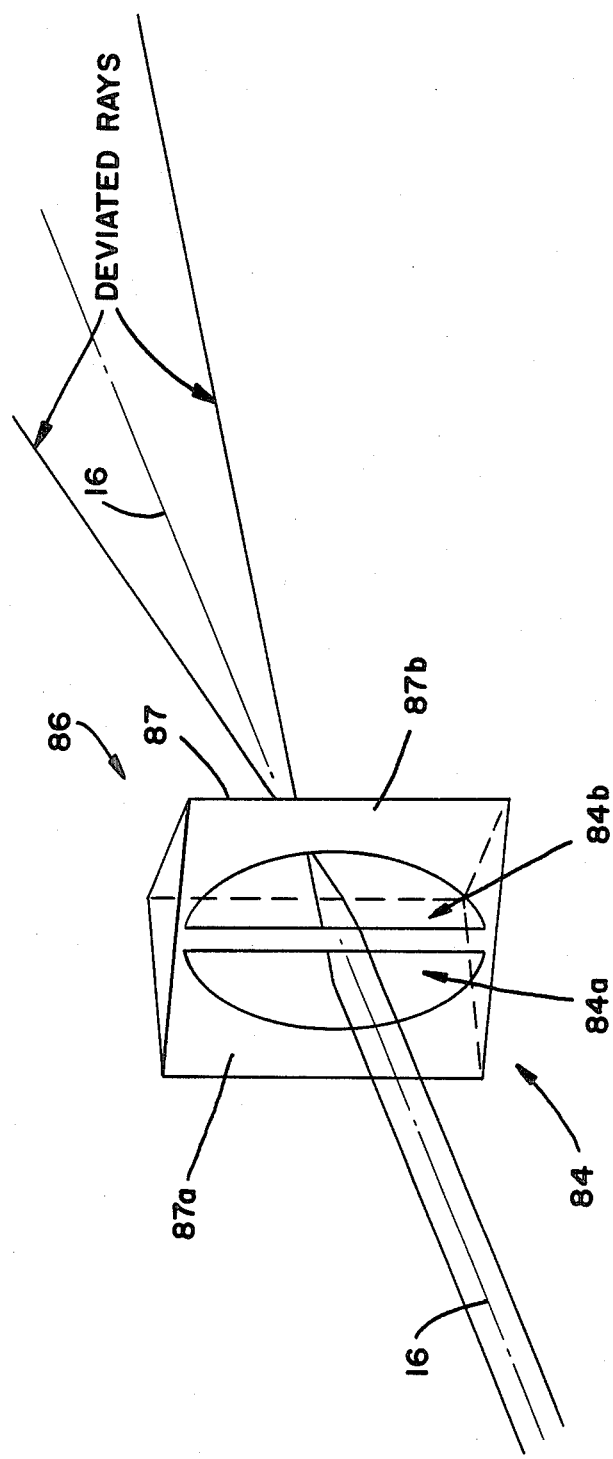
FIG. 2 is a pictorial view of an optical component of the optical system of FIG. 1.

More particularly, as previously mentioned, lenses 46 and 50 form an image of the pupil at aperture 52. Lens 56 then collimates the light from aperture 52 and lens 58 reimages the pupil in the plane of apertures 84a, 84b. Lenses 46, 50 and 56, in combination with the optics of the eye 12, form an image of the fundus in the plane of the rectangular aperture 90. If bi-prism 87 were removed from the axis 16, lenses 58 and 60 would simply reimage the region of the fundus on screen 66. However, when bi-prism 87 is in place, as illustrated, two laterally displaced images of this region of the fundus are formed on screen 66, as shown in FIG. 3A-1 and FIG. 3A-2. Because all the light in one of the images passes through aperture 84a and all the light in the other of the images passes through aperture 84b, and are deviated by bi-prism 87, these two images form a stereo pair of the same region on screen 66.

With reference to FIG. 3A-1 and FIG. 3A-2, the stereo pair of fundus images that are formed on screen 66 have the same blood vessels 92, e.g., a blood vessel 92A-1 in the left stereo picture and the identical blood vessel 92A-2 in the right stereo picture. As will be described below, three-dimensional or depth data can be obtained from the distance X along a horizontal scan line 1 between pairs of corresponding areas or features in the stereo pair, e.g., the distances between corresponding areas on the blood vessels 92A-1, 92A-2.

More generally, three-dimensional optical data are obtained whenever there are features of the fundus imaged on screen 66 that have a directional component perpendicular to a horizontal line joining the centers of the two apertures 84a 84b through which the stereo pair were taken. However, if the region of the fundus being examined or illuminated were featureless, (e.g., no blood vessels), as some regions are, no features would be imaged on the screen 66 and, therefore, no three-dimensional data would be available. Some regions of the ocular fundus may even have features but would appear featureless to TV camera 64 if illuminated with certain wavelengths. Therefore, to obtain three-dimensional data of these featureless or apparently featureless regions, subsystem 82 also has the following.

A mask 94 illustrated in FIG. 1 and having a narrow vertical slit (not shown) can be selectively interposed between lenses 22 and 24. The combination of lenses 24, 30 and 34, together with the optics of the eye 12, form an image of the slit on the ocular fundus. Then, when the stereo pair of images of a region is formed on screen 66, the images are of the fundus region having a pair of vertical lines 96A-1, 96A-2 shown in FIGS. 3A-1, 3A-2. As will be further described, the distance X' along horizontal scan line 1 between line 96A-1 and line 96A-2 provides the three-dimensional data used to examine the region of the fundus. Mask 94, as shown in FIG. 1, is mounted on the axial motion assembly 68 so that the mask 94 can be moved towards and away from lens 24 to bring the vertical slit in sharp focus on the fundus. Of course, as will become apparent, more than one such slit of mask 94 can be used to acquire more three-dimensional data.

The acquisition of the most accurate output data from TV camera 64 is dependent on the amount of any geometric distortion introduced by the camera 64 in scanning the image on screen 66. The TV camera 64 may be a silicon intensified target vidicon camera, in which the image is scanned by a deflected electron beam. The electrooptics of the camera 64 permit small distortions of the scan and, therefore, of the apparent spatial positions of the analog signals proportional to the intensity of the light of the fundus features and outputted from the camera 64. These distortions may change with, for example, temperature or component age. Because the extraction of depth or three-dimensional information from the stereo pair of images requires precise spatial localization of the images on screen 66 for high accuracy purposes, such distortion would compromise this accuracy if it were not corrected.

Consequently, the subsystem 82 can also include optical components for obtaining optical data to calibrate the distortion in the camera 64. Specifically, a mask 98 having a narrow vertical slit (not shown), identical to mask 94, can be moved into the position shown near the plane of aperture 90. A light source 100 then can be actuated to illuminate the slits of mask 98. Because aperture 90 is in the plane where the image of the fundus is formed if illuminated with source 20, lens 58, bi-prism 87 and lens 60 form two adjacent images of the slit of mask 98 on screen 66. These slit images are identical with the slit images 96A-1, 96A-2 that would appear on screen 66 if mask 98 were removed from the optical path and a perfectly flat region of the fundus were illuminated through mask 94.

Then, if there were no distortion in the TV camera 64, the calibration information read out of the camera 64 would comprise data identifying two adjacent slits of perfectly straight and parallel vertical lines. To provide the calibration data, mask 98 is moved into the position shown and source 100 is energized to illuminate the mask 98. The resulting image or calibration picture on screen 66 is then scanned and data are read out by camera 64. As will be further described, irregularities in this calibration picture are measured and corrections are calculated that, if applied to the calibration picture, would yield perfectly straight, vertical slit images. These same corrections can then be applied to an actual stereo pair of images of the type shown in FIG. 3A-1, 3A-2 to correct for distortion. If more than one slit is in mask 94 then the same number of slits is used in mask 98.

An alternative to the above-described calibration technique is to use a distortion-free TV camera for camera 64, such as a microchannel plate intensifier coupled to a solid-state array sensor. However, presently this device is new and expensive.

Optical system 14 should be accurately aligned with respect to the eye 12 so that the light properly enters the pupil and falls on the fundus. Therefore, optical system 14 can include optical components to provide manual coarse alignment and automatic fine alignment of the eye 12 relative to the optical axis 16.

To achieve manual coarse alignment, optical system 14 can include a subsystem 101 that has a near infrared light source 102 which casts diffuse illumination onto the area where the eye 12 is expected to be. Light from the source 102 that is reflected by the front of the eye 12 is reflected by movable mirror 40 through beam splitter 36, lens 46, and cold mirror 48. A lens 104 then propagates the near infrared light onto a mirror 106 which reflects the light onto a screen 108 of a TV camera 110 which is sensitive to the near infrared light. Lenses 46 and 104 combine to form an image on screen 108 of the facial area about the eye 12, e.g., an area of about 25 mm. in diameter including the pupil. As will be further described, the entire instrument 10, including optical system 14, can be driven toward and away from the eye 12 to focus the pupil image on screen 108 and can be driven sideways horizontally (in and out of the plane of the FIG. 1) with respect to the eye 12 until the pupil image is roughly horizontally centered on the screen 108. Then, the mirror 40 can be rotated around its horizontal axis A1, which results in the image of the pupil on screen 108 moving up and down, until the image is roughly vertically centered on screen 108.

To achieve automatic fine alignment, optical system 14 includes a subsystem 111 that has a fiber optic bundle 112 having a light input end 114 receiving light from source 20 and a light output end 116 having an infrared filter 118. The infrared light outputted through filter 118 is reflected by a hot mirror 119 through lens 34 and is then reflected by beam splitter 36 and rotatable mirror 40 to the eye 12, where it passes through the pupil and illuminates the fundus. The output end 116 of fiber optic bundle 112 is at a distance optically from lens 34 such that lens 34 forms an image of the end 116 in the plane of the pupil. This image is smaller than the usual pupil, e.g., it is about 1.5 mm. in diameter, and when alignment is correct, is centered on the pupil.

Thus, the infrared light from filter 118 at output end 116 passes into the eye 12 and illuminates the fundus. Then, the infrared light is reflected diffusely by the fundus and emerges from the pupil, in effect backlighting the latter. This light then is reflected by mirror 40 through beam splitter 36, lens 46, cold mirror 48, lens 104 and mirror 106 onto screen 108. The image now falling on screen 108 is of a bright pupil on a dark background, and this image is used for automatic fine alignment purposes. As will be further described, mirror 40 will be automatically rotated about its horizontal axis A1 and vertical axis A2 until this image is precisely centered on screen 108. When this occurs, the instrument 10 and eye 12 are accurately aligned.

Another feature of the optical system 14 is an optical subsystem 120, shown in FIG. 4, which is used to obtain images or pictures of different regions of the fundus, such as the optic disk, which is a region about 5 mm. toward the temple from the fovea. To obtain these images, the visual axis or optic axis of the eye 12 should be moved with respect to the optical axis 16. This is accomplished with the optical subsystem 120 by maintaining the optical axis 16 fixed and controlling the orientation of the visual axis or optic axis of the eye 12.

More particularly, subsystem 120 includes the rotatable mirror 40 through which the optical axis 16 passes exactly as shown in FIG. 1 and indicated in FIG. 4. A patient's viewing screen 122, which may be a display device such as a TV screen, displays a movable target 124, such as an "X". Light from the X-shaped target 124 passes through a lens 126 and a lens 128. A rotatable mirror 130, which can rotate about its vertical axis as shown by the double-headed arrow, reflects the light from lens 128 onto a mirror 132 which then reflects the light onto a mirror 134. The reflected light from mirror 134 then passes through a lens 136 into the eye 12. Lenses 126, 128 and 136, together with the optics of the eye 12, combine to form an image of the target 124 on the fundus along an axis 138.

Assume that the target 124 is positioned, for example, on screen 124 corresponding to an angle of about 17 degrees relative to optical axis 16. Therefore, the axis 138 is at an angle of about 17 degrees from the optical axis 16, so that when the patient moves eye 12 to look at the target 124, the region of the fundus illuminated by subsystem 18 in FIG. 1 and imaged by subsystem 42 in FIG. 1 onto screen 66 is about 17 degrees toward the temple, which is the optic disk. The movements of the target 124 across screen 122 make for fine adjustment in viewing the optic disk. Lens 128 can be manually controlled to be moved or positioned towards or away from lens 126 to correct for a patient's refractive error. For example, if the patient is nearsighted, lens 128 can be moved away from lens 126 to bring target 124 into focus for the patient. The focal lengths and positions of lenses 126, 128 and 136 are chosen so that the magnification of the image of the target 124 on the fundus is the same regardless of the position of lens 128.

The preceding discussion of subsystem 120 actually referred to the imaging of the optic disk of the right eye 12 on screen 66. To image the optic disk of the left eye 12, the entire instrument 10 can be moved horizontally to align the optical axis 16 with the pupil of the left eye 12. Then, mirror 130 is rotated 90 degrees about its vertical axis. Now, light from target 124 passes through lens 126 and lens 128, and is reflected by mirror 130 onto a mirror 140. From mirror 140, the light is reflected from a mirror 142 through a lens 144 into the eye 12. The combination of lenses 126, 128 and 144, together with the optics of the eye 12, forms an image of the target 124 on the fundus along an axis 146, which is at the angle about 17 degrees from the optical axis 16. Therefore, when the patient views the target 124, the region of the fundus illuminated by subsystem 18 in FIG. 1 and imaged by subsystem 42 onto screen 66 in FIG. 1 is about 17 degrees toward the temple, i.e., the region of the optic disk for the left eye 12. Proper focusing and magnification are obtained with lens 126, lens 128 and lens 144 for imaging the target 124 onto the fundus of the left eye 12 as described above for the right eye 12, and fine positioning is achieved by moving target 124 across screen 122.

To position the visual axis or optic axis of either eye 12 so that the fovea is imaged, the patient simply looks along the optical axis 16 to receive light from the source 20. The target 124 is not displayed at this time, so that no light enters eye 12 along axis 138 or axis 146. Other regions of the fundus than the optic disk can be imaged by providing another suitably positioned light source or target (not shown) on which the patient's vision can be fixed.

Figure 5:
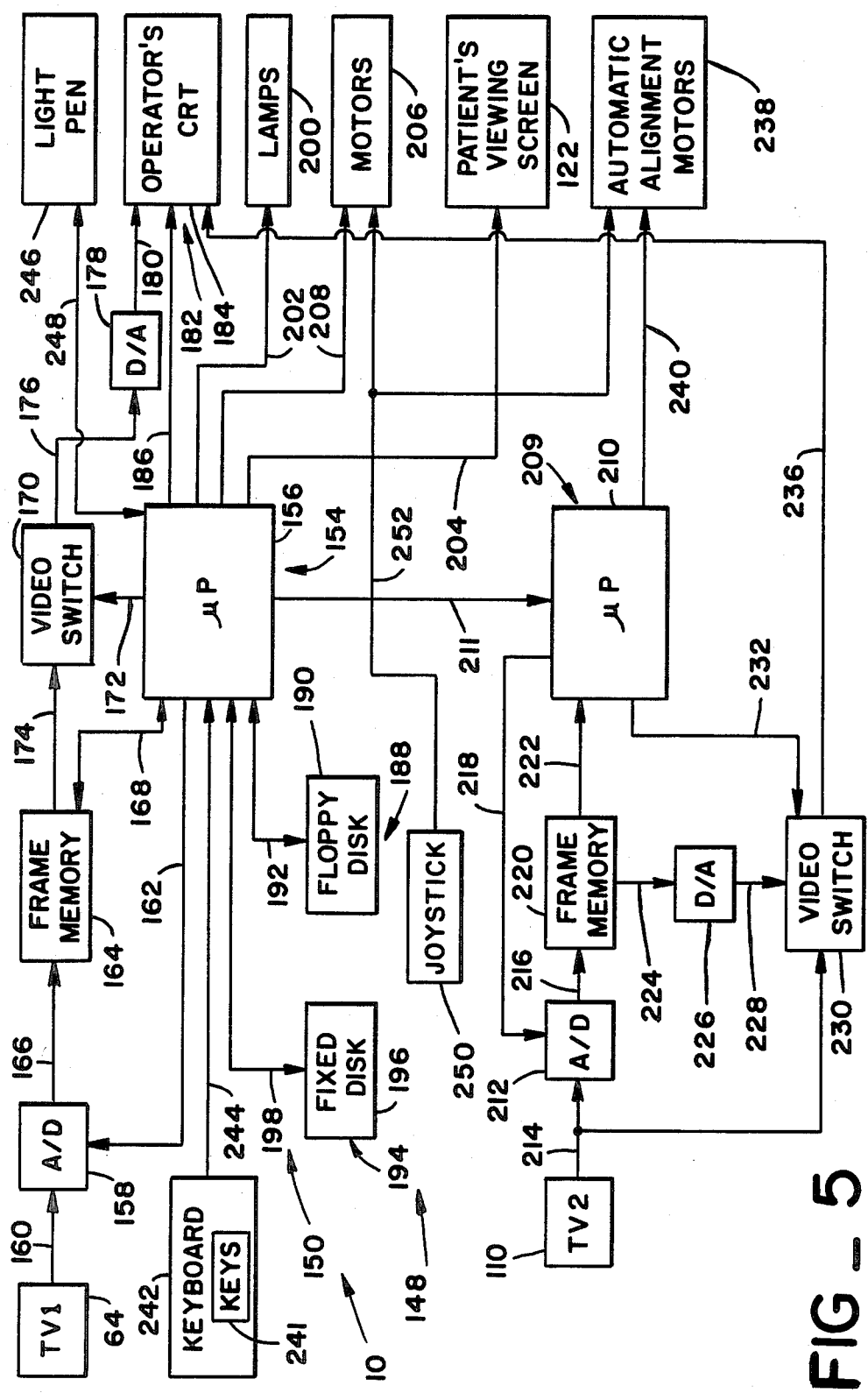
FIG. 5 is a block diagram of the hardware of an electronic data processor of the present invention.

FIG. 5 shows a block diagram of an electronic system 148 of the instrument 10 for storing digitally and displaying data about the ocular fundus and for performing other functions to be described. Electronic system 148 constitutes a data processor 150 having a microcomputer 154, such as a Model 8086 microprocessor 156 manufactured by the Intel Corporation, Santa Clara, Calif. Microprocessor 156, under software control, primarily performs the data storage and display functions.

An analog-to-digital (A/D) converter 158 receives, on a line 160, output video analog signals from the screen 66 in response to the scanning by TV camera 64 and converts the analog signals to a series of digital signals of, for example, 8-bit length. Thus, the intensity of the light falling on each small region of the screen is converted to analog data by camera 64 and then digitized by A/D converter 158. Microprocessor 156 controls the range of the A/D converter 158 over a line 162 to perform the equivalent of automatic gain control, ensuring that the full 8-bit range of the digitized levels is used regardless of the output level or amplitude of the analog signals on line 160. A frame memory 164 receives the digital signals from A/D converter 158 on a line 166 and temporarily stores digitally a frame at a time or one entire scanned picture of the image of the region of the ocular fundus on screen 66. Frame memory 164 is under read/write control of, and transfers an entire frame of data to, microprocessor 156 over a bi-directional line 168.

An on-off video switch 170, when turned on in response to a control signal from microprocessor 156 on a line 172, couples each frame of digital data stored in frame memory 164 from a line 174 to a line 176. A digital-to-analog (D/A) converter 178 converts the digital data on line 176 to video analog signals which are outputted on a line 180. An operator's monitor or display 182, such as a CRT display 184, displays the information received on line 180, i.e., the image of the ocular fundus falling on screen 66 is displayed on CRT display 184. Microprocessor 156 controls the CRT display 184 to display this image information via a control line 186 carrying the usual display control signals.

A digital data storage device 188, such as a floppy disk 190 used with a floppy disk drive (not shown), communicates with microprocessor 156 over a bi-directional line 192 to store a plurality of frames of digital data, each acquired from frame memory 164. Thus, floppy disk 190 can store digitally fundus images acquired over time from a patient during two or more eye examinations, and can store digitally a plurality of fundus images acquired during a single eye examination.

Another digital data storage device 194, such as a hard disk 196 used with a Winchester disk drive (not shown), is in communication with microprocessor 156 via a bi-directional line 198. Hard disk 196 can store the system and applications software to be described for performing the various functions carried on by instrument 10. Hard disk 196 can also be back-up storage for floppy disk 190.

Microprocessor 156 controls the turning on and off of various lamps 200 over a line 202. The lamps 200 include light source 20, light source 100 and light source 102 shown in FIG. 1. Microprocessor 156 controls the patient's viewing screen 122 (see also FIG. 4) via a control line 204 by generating and positioning the target 124 to examine various regions of the optical fundus, as previously described. Furthermore, microprocessor 156 controls the energization and de-energization of a plurality of motors 206 over a line 208 which move various optical components, as will be described.

Data processor 148 also includes a microcomputer 209 such as a Model 8088 microprocessor 210 manufactured by the Intel Corporation. Microprocessor 210 is controlled or instructed by microprocessor 156 via a line 211 primarily to initiate and perform the optical alignment functions. An analog-to-digital (A/D) converter 212 converts the video analog signals being outputted by TV camera 110 over a line 214 to digital data on an output line 216. A/D converter 212 is a one-bit digitizer or comparator which compares each analog signal identifying the intensity of light falling on a corresponding position on screen 108 with a threshold level and produces a logic 1 or 0 on a line 216 for each such comparison. Microprocessor 210 adjusts the threshold level of A/D converter 212 via a control line 218 for reasons to be described.

A frame memory 220 temporarily stores a frame of digital data, i.e., stores all the bits on line 216 constituting one scan by TV camera 110, and transfers this frame of digital data over a line 222 to microprocessor 210. The digital data in frame memory 220 also are fed over a line 224 to a digital-to-analog (D/A) converter 226 that converts the data back to video analog signals which are outputted on a line 228. An on-off video switch 230 is under control by microprocessor 210 over a line 232 to couple, when turned on, the analog signals on line 228 and the analog signals on line 214 onto a line 236. The CRT display 184 receives the signals on line 236 to display the images falling on screen 108 and scanned by TV camera 110.

Microprocessor 210, in response to the digital data on line 222, and under control of the software stored on hard disk 196, controls the energization and de-energization of various automatic alignment motors 238 over a line 240.

Microprocessor 156 and, hence, microprocessor 210, are commanded to perform their functions by means of input keys 241 on a keyboard 242, coupled over a line 244 to microprocessor 156, and a light pen 246 which is coupled to and activated by microprocessor 156 via a bi-directional line 248. Light pen 246 can be applied to the screen of CRT display 184 for reasons to be described. Also shown in FIG. 5 is a manual control lever or joystick 250 which is used to actuate one or more of the motors 206 and one of the motors 238 over a line 252 for manual alignment and other purposes to be described.

In the overall operation of instrument 10, including optical system 14 and data processor 150, for examining the eye 12, assume that the instrument 10 is powered-up and is otherwise ready to perform its functions. Also assume that a patient has been initially positioned with her eye 12 approximately in the correct position relative to optical axis 16 and that the region of the ocular fundus to be examined is the fovea, so that the patient is looking directly along optical axis 16.

Manual and Automatic Alignment

To assure the highest accuracy, the manual and automatic alignment procedures should be sequentially activated. The operator first depresses a manual alignment key 241 on the keyboard 242, causing microprocessor 156 to energize light source 102 and to activate CRT display 184. Microprocessor 156 also instructs microprocessor 210 to close video switch 230 and, thereby, couple TV camera 110 to CRT display 184. An image of the facial area of about 25 mm. in diameter, including the pupil of the eye 12, is then formed on screen 108, scanned and read out by TV camera 110 as analog signals on line 214. Video switch 230 then couples the analog signals onto line 236, ultimately resulting in the pupil image being seen by the operator on CRT display 184.

To coarsely center the pupil image on the optical axis 16, the operator then manipulates joystick 250 to energize one of the motors 206 to move the entire instrument 10 toward or away from the eye 12 until the pupil image appears sharply focused on CRT display 184. Then, the operator manipulates the joystick 250 to energize another of the motors 206 which moves the entire instrument 10 sideways horizontally relative to the eye 12 until the pupil image is centered roughly horizontally on the CRT display 184. Next, the operator manipulates the joystick 250 to energize one of the automatic alignment motors 238 which causes rotatable mirror 40 to rotate about its horizontal axis A1. This causes the image of the pupil seen on CRT display 184 to move vertically and when it is roughly centered the operator ceases this movement. At this time, then, the image of the pupil of the eye 12 is roughly centered on CRT display 184, as well as on screen 108 of TV camera 110 which is fixedly centered on the optical axis 16 of the instrument 10. Therefore, the eye 12 is roughly aligned with optical axis 16.

Having manually and roughly centered the eye 12 relative to the optical axis 16, the operator then depresses an automatic alignment key 241 on the keyboard 242. Microprocessor 156 responds by turning off light source 102 and turning on light source 20, and by instructing microprocessor 210 to switch to the automatic alignment mode. As a result of the infrared light emerging from the output end 116 of fiber optic bundle 112, an image of the pupil on a dark background is now formed on the screen 108 of TV camera 110.

Figure 6:
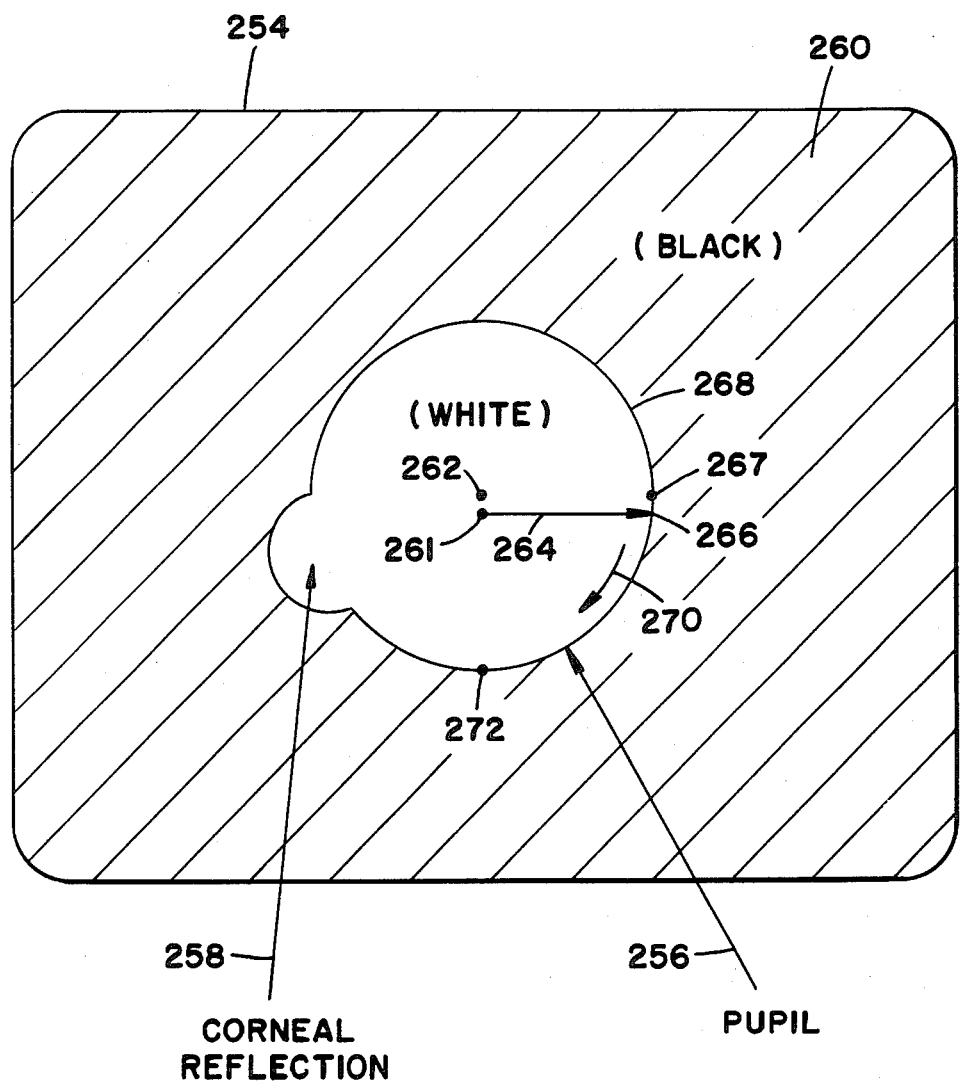
FIG. 6 illustrates an image of the pupil of the eye for explaining an automatic alignment feature of the present invention.

As one example, FIG. 6 illustrates a picture 254 that is at the screen 108 during a threshold setting procedure that is described below. To show a worst case eye reflection situation, the picture 254 includes the white image 256 of the pupil in which a small white area 258 also appears, the area 258 resulting from, for example, some corneal reflection that obscures part of the pupil image. Also shown is the dark background 260.

Next, the threshold of A/D converter 212 is initially set by microprocessor 210 to the highest level. Thereafter, one frame or picture of the pupil image on screen 108 is scanned by TV camera 110, digitized by A/D converter 212 and stored in frame memory 220, with each stored bit representing a single pixel of a white or dark level. Microprocessor 210 then accesses the frame of bits stored in frame memory 220 and counts the total number of bits representing white pixels, which should be few due to the high threshold level while the total number of bits representing the black pixels should be high. Microprocessor 210 then sets the threshold level of A/D converter 212 one step lower, and the above procedure is repeated, i.e., again the total number of bits representing white pixels is counted, which should be several more than previously counted due to the slightly lower threshold level. This procedure of lowering the threshold level and counting the "white" bits is followed until there is an abrupt change in the total number of "white" bits counted. At this point, the appropriate threshold level is reached for continuing with the automatic alignment procedure.

To further adjust the threshold level, if necessary, microprocessor 210 then closes video switch 230 which allows the present digitized picture in frame memory 220, after being converted by D/A converter 226, to be coupled to and displayed on CRT display 184. Thus, the picture falling on screen 108 is displayed on CRT display 184. The operator, by means of a control knob (not shown) can then view the display 184 and fine tune the threshold level of A/D converter 212 until a very clear picture of the white pupil image is seen contrasted against a dark background.

With the picture appearing on screen 108 as shown in FIG. 6, and being scanned by TV camera 110, digitized by A/D converter 212 and stored in frame memory 220, the automatic alignment procedure continues as follows in order to determine the center of the pupil image 256 relative to the center of screen 108. Microprocessor 210 accesses a frame of bits stored in frame memory 220 and examines the bits by starting with the bit corresponding to a pixel 261 near the center 262 of image 256, which bit represents a white pixel since the pupil image 256 has been roughly centered on screen 108 during manual alignment. Then, microprocessor 210 examines sequentially bits corresponding to pixels on a horizontal line to the right of the pixel 261, as shown by the arrow 264 in FIG. 6. When a bit corresponding to a black pixel is encountered, as shown by numeral 266, microprocessor 210 then examines the bits corresponding to the border 268 by following the border 268 vertically upward from pixel 266, so long as the direction of border 268 is toward the right. Otherwise, microprocessor 210 turns around and begins to trace the border 268 vertically downward from pixel 266, so long as the direction of the border 266 is to the right. In this way, the bit corresponding to the rightmost position of border 268 is identified, e.g., the bit corresponding to a pixel 267, thereby defining the vertical position of the center 262 of the pupil.

Thereafter, microprocessor 210 examines the bits identifying pixels around the pixel 267 by following the border 268 downwardly along the arrow 270 until the edge of the border 268 begins to turn upwardly at pixel 272. At this pixel 272, the horizontal position of the center 262 of the pupil is identified. Thus, the bit corresponding to pixel 267 and the bit corresponding to pixel 272 define the X-Y coordinate data of the center 262 of the pupil image 256.

Next, using this X-Y coordinate data of the center 262, and having available the known X-Y coordinate data of the center of the screen 108, microprocessor 210 calculates the difference between the pupil center 262 and the center of screen 108 and generates respective X and Y error signals. In response to these error signals, microprocessor 210 then drives respective X and Y alignment motors 238 to rotate mirror 40 about its vertical axis A2 and its horizontal axis A1 until the pupil image 256 is centered and no error signals are generated. The generation of the error signals and rotation of mirror 40 continuously occur during the examination to follow small eye movements, thereby constantly automatically aligning the eye 12 relative to optical axis 16. The above procedure is for the right eye; for the left eye the corneal reflection 258 lies on the opposite side from that shown and the search commences towards the left rather than towards the right along line 264.

Acquisition of Digital Data, Generally

With the automatic alignment procedure described above being in effect, digital data can be acquired by first depressing a select key 241 on keyboard 242 corresponding to, for example, white light. Microprocessor 156 responds by energizing a motor 206 to rotate filter wheel 70 to position the appropriate filter 74 or aperture on wheel 70 along the optical axis 16. Thus, the ocular fundus is illuminated with white light from source 20.

Then, a read key 241 is depressed, causing microprocessor 156 to read a frame of digital data stored in frame memory 164 and to store this data in floppy disk 190. Other such readings can be taken merely by depressing the read key 241.

Acquisition of Reflectance Spectrum Data

With the automatic alignment procedure being in effect, a select key 241 corresponding to one wavelength of light is depressed. Microprocessor 156 responds by energizing a motor 206 to rotate filter wheel 70 to position the corresponding filter 74 along the optical axis 16. Thus, the ocular fundus is illuminated at the selected wavelength. Then, the read key 241 is depressed, causing microprocessor 156 to read the frame of data in frame memory 164 and to store these data in floppy disk 190. This first frame of data stored in floppy disk 190 may be considered to be a "master" frame for registration purposes to be described.

Then, additional readings at different wavelengths can be taken. For each reading, a different select key 241 is depressed, causing microprocessor 156 to operate a motor 206 to rotate filter wheel 70 until another selected filter 74 is along the optical axis 16. Next, the read key 241 is depressed, resulting in a frame of data being stored in floppy disk 190 corresponding to the other selected wavelength. Thus, frames of data are stored in floppy disk 190, each corresponding to the amplitude of light at a different wavelength falling on the ocular fundus and all the frames taken together thereby containing information from which to derive a reflectance spectrum.

Between readings taken at the different wavelengths, slight movements of the eye 12 will occur, resulting in readings being taken of slightly different regions of the ocular fundus. Consequently, for reasons which will become apparent, all frames of data stored in floppy disk 190 should be registered with one another and this is accomplished in the following manner.

A key 241 calling up the "master" frame is depressed, and microprocessor 156 responds by reading the "master" frame in floppy disk 190 and displaying the corresponding fundus image on CRT display 184 as a positive picture. Then, another key 241 is depressed, causing microprocessor 156 to read another frame of data stored in floppy disk 190 and taken at a different wavelength and to display the corresponding fundus image on display 184 as a negative picture simultaneously with the positive "master". The operator will then manipulate a control knob (not shown) on the CRT display 184 to move or shift the negative image in registration with the positive image until they are precisely aligned or at least well matched. This visual registration is accomplished by aligning features on CRT display 184, such as blood vessels of the ocular fundus. During this movement, microprocessor 156 receives data from CRT display 184 identifying the magnitude of the amount and the direction of the shift. When the shift or registration is completed, the operator depresses a key 241 which instructs the microprocessor 156 to store this magnitude and direction data in floppy disk 190. These data are later used to compute the correct spatial relationships among these two images or pictures so that pixels at the same location in the two pictures can be assumed to represent the same point on the fundus.

Thereafter, with the "master" frame still being displayed on CRT display 184, each of the other frames of data taken at different wavelengths can be sequentially fetched and displayed as a negative on display 184 and then registered with the "master" to acquire the shift magnitude and direction data for the corresponding picture. Alternatively, both the "master" and all other frames of data can appear as positives on display 184. The positive master and a given other positive frame can appear alternately on the display 184 at, for example, two alterations per second. The operator can then move one of these frames until they are superimposed on one another, i.e., registered. Again, the shift magnitude and direction data are acquired.

Once the pictures taken at different wavelengths have been digitally stored in floppy disk 190 and registered as described above, various information about the ocular fundus can be displayed on CRT display 184, as will now be described.

Spot Reflectance Spectrum

The operator depresses a key 241 causing microprocessor 156 to read a selected stored picture in floppy disk 190 and to display this image of the ocular fundus on CRT display 184. Then, the operator uses the light pen 246 to point to any desired spot or pixel on the CRT display 184. In response to this pointing of the light pen 246, microprocessor 156 reads the stored data in each of the stored pictures in floppy disk 190 taken at different wavelengths and corresponding to the spot or pixel at which light pen 246 is pointing. Since each picture was taken at a different wavelength, these read data identify the energy or intensity of the spot reflectance at different wavelengths and are processed by microprocessor 156 to display on CRT display 184 a graph of the light intensity vs. wavelength for that spot, which is the reflectance spectrum. In a similar manner, the light pen 246 can be used to point to any other pixel on the picture called up on CRT display 184 to provide the reflectance spectrum for that spot of the ocular fundus. In producing this reflectance spectrum, microprocessor 156 will correct for the light sensitivity of the camera 64, using the sensitivity data previously acquired, as mentioned above.

Feature Enhancement

Other information that can be obtained relates to various features of the ocular fundus. For example, it may be important to see the distribution of oxygenated blood in the region of the ocular fundus being examined. The operator can then depress a key 241 calling for information about this distribution. Microprocessor 156 responds by reading two particular stored pictures in floppy disk 190 taken at different wavelengths. Microprocessor 156 then takes the ratio of the intensities of each of the corresponding pixels on the two pictures and produces new data that are proportional to each such ratio. These new data constitute a "ratio picture" which is then displayed on CRT display 184. In performing this operation, microprocessor 156 again corrects for the light sensitivity of camera 64.

More specifically, since information about the oxygenated blood is desired, one of the two stored pictures selected by microprocessor 156 is the one taken at a wavelength for which oxygenated and reduced blood have equal reflectances and the other at a wavelength where those two reflectances are as different as possible. Under these conditions, it can be shown that the ratio of the intensities of the two pictures at any pixel is proportional to the concentration of oxygenated blood at that pixel. Thus, the displayed ratio picture is information about the distribution of oxygenated blood.

To further enhance the ratio picture or render this information more visible, the ratio picture can be split by the microprocessor 156 and pseudocolored, e.g., all pixels with ratios between 0.0 and 0.1 can be colored blue, all pixels with ratios between 0.1 and 0.2 can be colored green, etc. Alternatively, iso-ratio contour lines can be calculated and superimposed on the displayed ratio picture. Quantitative measures are also available, such as the total area of the ratio picture in which the ratio is between, for example, 0.4 and 0.5.

Change Enhancement

In this mode, a change in the ocular fundus is the information that is acquired. For this mode, it is assumed that, for example, two pictures of a given region of the ocular fundus have been taken and digitally stored at substantially different times, e.g., weeks apart. The two pictures are first registered with one another in the manner described above. Then, a "change enhancement" key 241 is depressed calling for this feature. In response, microprocessor 156 reads the data stored in floppy disk 190 for these two pictures, calculates the ratio of corresponding pixels and displays on CRT display 184 a ratio picture in the manner described above for the Feature Enhancement mode. This ratio picture will be a uniform grey, except where changes have occurred. The quantitative aspects of the change can be visually enhanced by using level splitting, pseudocolor and contour lines as described above.

Alternatives to Feature Enhancement and Change Enhancement

As an alternative to calculating and displaying a ratio picture for either the Feature Enhancement or the Change Enhancement mode, similar information can be obtained with a "difference picture". Microprocessor 156, instead of calculating a ratio, determines the difference in intensity of the corresponding pixels of the relevant pictures after correcting for the sensitivity of camera 64, and displays the resulting difference picture on CRT display 184.

Abnormalities in the Two-Dimensional Shape

Other important information that can be acquired with the instrument 10 is any abnormality or change in the two-dimensional shape of the region of the ocular fundus under examination. For example, such a change can be in the size of a discolored area or in the tortuosity of blood vessels. The change can be analyzed by using the same procedure described above for the Change Enhancement mode, i.e., by computing a ratio or difference picture and displaying it on CRT display 184.

Abnormalities in the Three-Dimensional Shape

The operator commences this mode by depressing a "three-dimensional shape" key 241 on keyboard 242. Then, microprocessor 156 actuates one of the motors 206 to move mask 94 into position along the optical axis 16 and actuates another of the motors 206 to move system 82 into the position along the optical axis 16. Consequently, a stereo pair of images 92A of a region of the fundus, such as shown in FIG. 3A, may be obtained at detecting plane 66. However, rather than the stereo pair of images shown in FIG. 3A, assume that the stereo pair is as shown in FIG. 3B, i.e., stereo pair 92B. As will become apparent, whereas the straight lines 96A-1, 96A-2 of FIG. 3A indicate a region of the ocular fundus that is flat, the corresponding curved lines 96B-1, 96B-2 indicate that this region is not flat, but is subject to, e.g., cupping.

Thereafter, the stereo pair of images 92B is scanned by TV camera 64, digitized by A/D converter 158 and stored in floppy disk 190 by microprocessor 156. Then, as will be further described, microprocessor 156 measures along horizontal scan lines 1 the distances X shown in FIG. 3B between corresponding features on the stereo pair 92B, such as one of the blood vessels 92B-1, 92B-2 or, preferably, the lines 96B-1, 96B-2. The distances X are each proportional to the distance in the depth dimension between an optical reference point near the center of the pupil of the eye 12 and the region being examined on the fundus. Therefore, if the region being examined were not cupped (and neglecting camera distortions), all the distances X between lines 96B-1, 96B-2 would be identical, as shown for lines 96A-1, 96A-2 in FIG. 3A. However, since the region is cupped, these distances X are not all equal, as can be clearly seen in FIG. 3B.

Having measured the distances X along all the horizontal scan lines, microprocessor 156 can now control CRT display 184 to display a depth profile of the fundus region coincident with lines 96B-1, 96B-2. This depth profile is illustrated in FIG. 3C, which is a graph of the region of the fundus illuminated along the lines 96B-1, 96B-2 vs. distances X. This depth profile of FIG. 3C represents what would be seen if the fundus were cut along the region coincident with lines 96B-1, 96B-2 and then viewed edge-on.

To generate a highly accurate depth profile, the distances X should be measured with great precision. In general the accuracy of the depth profile shown in FIG. 3C depends on the ability to identify corresponding areas along a horizontal scan line 1 of line 92B-1 and line 92B-2. This identification can be difficult because even if the fundus is illuminated with a very fine and sharply focused vertical line as a result of imaging the slit of mask 94 shown in FIG. 1, the resulting images of this line shown in FIG. 3B as lines 96B-1, 96B-2 may appear defocused because of light scatter by the fundus, as well as from optical aberrations in the eye 12 and in the instrument 10.

Figure 7:
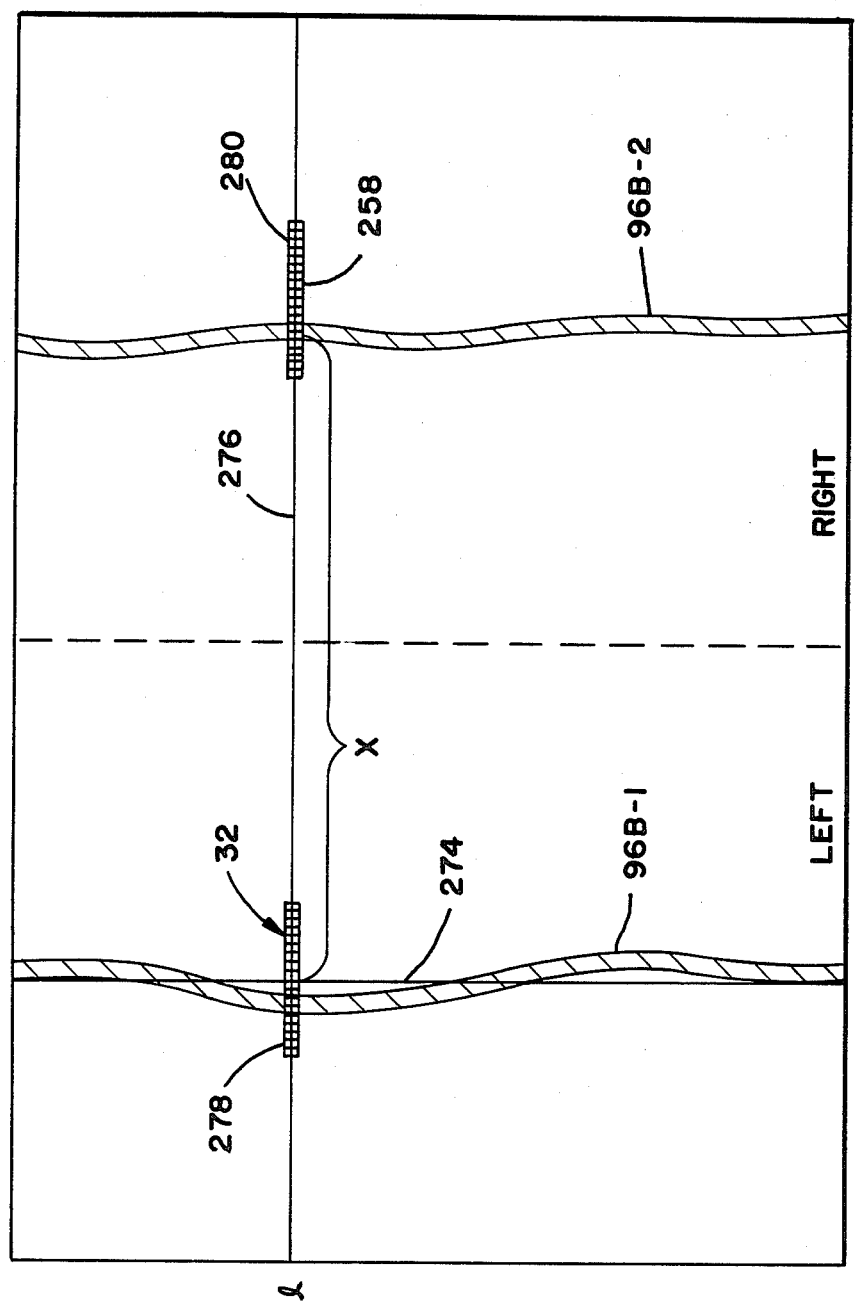
FIG. 7 is a view used to explain a specific manner of obtaining the depth profile of FIG. 3C.

Preferably, therefore, to acquire a highly accurate depth profile, a technique is used that will be described with reference to FIG. 7 which shows an expanded view of the lines 96B-1, 96B-2, but not the other fundus features, such as the blood vessels, to simplify the illustration. Microprocessor 156 generates a fine vertical line 274 on screen 66 that is approximately centered on line 96B-1 of the left image of the stereo pair 92B. Because the exact location of line 274 relative to line 96B-1 is not critical, and because the location of line 96B-1 on screen 66 will be approximately in the same place for all eyes 12, the line 274 can be generated at the same location for all eyes.

Then, microprocessor 156 evaluates each horizontal scan line, such as a scan line 276, in turn in the following way. Assume there are 256 pixels along a scan line 276, with 128 pixels in each image of the stereo pair 92B numbered 0-127 and 128-255, respectively. As a scan along a horizontal line 276 occurs, A/D converter 158 generates the digital data identifying the intensity of the light at each of the 256 pixels and microprocessor 156 temporarily stores these data in system memory (not shown). Then, microprocessor 156 evaluates a pixel group 278 containing, for example, 32 pixels, and centered on the line 274, by reading the digital data stored in system memory (not shown) and corresponding to this group 278. Next, microprocessor 156 evaluates the first 32 pixels of the scan line 276 for the right side of the stereo pair 92B, e.g., pixels numbered 128-159, by reading the corresponding stored digital data. Microprocessor 156 then correlates the pixel group 278 with the group of pixels numbered 128-159. Then, microprocessor 156 reads the stored data corresponding to the next group of pixels 129-160 and correlates this group with the pixel group 278, and so on.

This correlation procedure continues until the pixel group 278 centered on line 274 has been correlated with every group of 32 pixels numbered 128-159, 129-160, 130-161, etc., of the right picture of the stereo pair 92B. The position of the center of the group of 32 pixels in the right picture, for example group 280 shown in FIG. 7, for which the correlation is the highest is determined to be the position in the right picture that corresponds to the center of the pixel group 278. The distance between these two centers is the distance X for that scan line 276. When this procedure is completed for each horizontal scan line, and the distance X determined for each scan line, microprocessor 156 then generates the depth profile shown in FIG. 3C on CRT display 194.

As an example, the pixel group 278 has been given as containing 32 pixels, but the group can contain a different number, e.g., 16. Further, because for even the largest cupping in the fundus, the actual displacement in the third dimension is small, the region of the right picture of the stereo pair 92B having the highest correlation with the pixel group 278 along a scan line 276 can usually be found within a restricted pixel group. Therefore, it is not necessary to correlate every pixel group in the right picture with the group 278. Typically, as few as 16 groups centered around the middle of the right picture need be examined.

As previously mentioned, the only reason for using the mask 94 is to illuminate those areas of the fundus under examination that are essentially featureless, e.g., that have no blood vessels, or any features that cannot be adequately distinguished by optical system 14 and TV camera 64, to acquire the necessary stereo pair of images on screen 66. For those regions that contain features such as blood vessels that are distinguishable, mask 94 is not required. Then, a procedure similar to that described above could be used to display a depth profile of a given region by evaluating the distances X between corresponding blood vessels in the stereo pair.

In summary, therefore, the present invention solves the problems previously mentioned in connection with prior fundoscopic detection techniques for acquiring data for detecting disorders of the eye as well as the entire body. The data that are acquired and processed with the present invention are objective data and highly accurate, unlike the data acquired by a physician using an ophthalmoscope. Also, more accurate reflectance spectra data are acquired using the present invention than are acquired using the prior fundus camera. This is because the present invention does not have the problems associated with developing film that has a plurality of photographs taken at different wavelengths. Moreover, none of the prior techniques provide an accurate and objective technique for evaluating the three dimensional shape or changes in the shape or color of the fundus over time, as does the present invention.

Included as a part of this disclosure at the end of the specification and prior to the claims is a Topograph (Ocular Fundus Analyzer) Procedure Glossary followed by software that is used to perform the previously mentioned functions of the present invention and other functions that will become apparent. The software is divided into a Listing No. 1, a Listing No. 2 and a Listing No. 3. The Topograph Procedure Glossary includes a Word column, a Vocabulary column and a Source column. The Word column gives a particular word followed beneath by a sentence indicating the function of a portion or routine of the software, e.g., ?Hit—Detects illuminated pixels beneath lightpen. The Vocabulary column identifies the component which is associated with the word in the Word column, e.g. Video, which relates to the Operators CRT 184. The Source column gives the location, in hexadecimal, of the corresponding portion of the software in the following software listing, e.g. location 4584 corresponding to Hit.

The software is written in a language known as Forth and a Forth implemented 8086 Assembler, which is sold by Forth, Inc. The software is a modified version of Forth, Inc.'s commercially available program 86/12-202 PROM polyForth, dated Mar. 27, 1982. This software was developed specifically for the 86/12A single board microcomputer, manufactured by the Intel Corporation and an SBC202 floppy disk controller; however, as described below, modifications have been made to support a floppy disk controller model 1403D, manufactured by Shugart Associates, Sunnyvale, Calif. As the name PROM polyForth implies, the software is implemented in EPROM (i.e., four 2716's). The 86/12A single board microcomputer includes the microprocessor referenced herein as microprocessor 156.

A polyForth Target Compiler was used to change the above-mentioned EPROMs to support the Shugart 1403D floppy disk controller. The only changes were to redefine the disk support words FDC, FLOPPY, (BUFFER) and (BLOCK). This is indicated in Listing No. 1 of the software, which listing contains the code for these words.

Listing No. 2 of the software contains the object code for the 86/12A single board microcomputer. This software can be stored in precompiled form on a disk, read into RAM and then started using FORTH commands.

The various motors, mirrors, lamps and pupil alignment camera 110 previously described are controlled directly by the peripheral microprocessor 210, which can be the 8088 manufactured by the Intel Corporation. The software for the 8088 can be target compiled by the 86/12A as a closed headless FORTH system. The 86/12A and the 8088 can communicate using a shared memory region which they can jointly access. This region also can be used to exchange messages and hold common variables. Listing No. 3 contains the object code for the 8088 peripheral processor.

Other aspects, objects and advantages of the invention can be obtained from a study of the drawings, the disclosure and the appended claims.

```
                    Topograph Procedure Glossary
WORD......... VOCABULARY... SOURCE. .........,,,,,..........

?HIT            VIDEO           4584
    Detects illuminated pixels beneath lightpen.

?REQ            8088            7AE
    Tests whether the 8086 is requesting 8088 action.

?TIP            VIDEO           4564
    Tests for lightpen tip depression.

AC@             8088            811
    Using an address stored in an 86/88 communication area,
    fetches a byte and leaves in the comm area.

AC@             86->88          518F
    Request the alignment processor to fetch a byte of its memory.

ACKREQ          8088            7C5
    Acknowledges an 8086 request.

AGCPROF         VIDEO           4C0C
    Real time frame grabbing with automatic gain control of the
    SIT camera ADC.

AUTOREF         8088            A15
    Computes the ADC reference value that gives the sharpest
    pupil edge.

AUTOREF         86->88          5181
    Requests the alignment processor to compute an optimal
    alignment camera ADC reference value for digitizing a 1 bit
    image of the pupil.

AVID            VIDEO           464A
    Selects alignment video signal as RGB DAC reference.

CENTER          8088            D8A
    Computes the center of the 1 bit pupil in grab RAM.

CPRO            CORRELATE       5FEF
    Computes the depth profile for a given pair of vertical lines.

DAVE            OPERATOR        5809
    Displays 1 bit digitized alignment video so that operator
    can center the pupil prior to requesting eyetracking.

DAVID           VIDEO           4660
    Select digitized alignment video as RGB DAC reference.

DEPTH           CORRELATE       5C09
    Computes the peak variance and depth of the fundus for a
    single raster line.
```

EXAM          OPERATOR           5899
    Enters the standard patient examination routine for acquiring
    and storing fundus data.

EYETRACK      8088               DED
    Tracks the pupil at 30 Hz, servoing if enabled, and monitoring
    requests from the 8086.

WORD......... VOCABULARY... SOURCE. .............................

EYETRACK      86->88             51A9
    Requests the alignment processor to begin tracking the pupil.

EYETRACK/     8088               E18
    Stops tracking.

EYETRACK/     86->88             51C3
    Requests the alignment processor to stop tracking the pupil.

FILTER        CORRELATE          5BCF
    A nonrecursive variable low pass digital filter routine used
    to smooth the crosscorrelation function prior to computing
    its peak.

FINDSLITS     CORRELATE          5F1B
    Locates the vertical lines projected on the fundus in VRAM.

FROMDISK      VIDEO              48A2
    Reads a frame from disk to VRAM.

GRAB          VIDEO              45E8
    Writes the next frame from the SIT camera to video RAM.

HIST          8088               998
    Computes a histogram of light pixel tallies as a function of
    alignment camera ADC reference value.

HOME          OPERATOR           530F
    Initializes video switch, CRAM, cameras, motors & bistables.

HSCROLL       VIDEO              45F9
    Updates the horizontal scroll register.

INIT88        8088               80
    Initializes the 8088, target FORTH system pointers and the
    8255 I/O port.

IOREQ         86->88             4F39
    Interprocessor communication primitive used to select
    alignment processor functions.

LIVE          VIDEO              46A4
    Select either SIT camera ADC or VRAM with which to enter the
    color RAM lookup tables.

MAN           OPERATOR           5794
    Displays live alignment video so that operator can center
    the pupil manually before requesting automatic eyetracking.

MONITOR       8088               A37
    Monitors 8086 requests & performs them by vectored execution.

MONKEYS          OPERATOR           5764
    Monitors the operator input and executes primary control
    routines by vectored execution.

PALLOR           ANALYSIS           64F4
    Computes the pallor of two registered pixels and stores the
    value in VRAM.

WORD......... VOCABULARY... SOURCE. ...............................

PALLORKEYS       ANALYSIS           68EA
    Displays the pseudocolored contents of VRAM and enables
    interactive control of the assignment of colors to the values
    in VRAM. Used primarily for enhancing small differences in
    ratio pictures.

PEAK             CORRELATE          5AF7
    Finds the peak of the crosscorrelation function.

RATIO            ANALYSIS           652E
    Computes in place the ratio of two registered frames.

REALREG          VIDEO              4708
    Select the display mode for registering a stored frame with
    a live frame.

REG              VIDEO              46A4
    Select the display mode for registering two stored frames.

REGISTER         ANALYSIS           6440
    Displays a positive fundus frame overlaid by a negative fundus
    for manual registration by horizontal & vertical scrolling of
    one image with respect to the other.

START88          8088               E23
    Initializes interrupt service and monitors 8086 requests.

TALLYHI          8088               96E
    Counts the number of light pixels in pupil grab RAM.

TODISK           VIDEO              48AE
    Writes a frame from VRAM to disk.

VBLANK           VIDEO              4634
    Selects ground as the RGB reference.

VRAM             VIDEO              4676
    Selects video RAM as RGB reference.

VSCROLL          VIDEO              460E
    Updates the vertical scroll register.

WIPE             VIDEO              4623
    Clears video RAM to FF.

XCORRELATE       CORRELATE          5A9C
    Computes the crosscorrelation function of two vertical lines
    illuminated on the fundus.

[BLOCK]     +DISK          2D3F
   Error trapping version of BLOCK.
   The system variable 'BLOCK vectors to this routine.

[BUFFER]    +DISK          2CED
   Version of BUFFER which tests for disk errors and retries
   10 times issuing an error message if necessary.
   The system variable 'BUFFER vectors to this routine.

LISTING NO. 1

```
1A33   58 BF 76 20 AA   59 81 F9 67  2 7E  5 B8   20  0 EB
1A43    2 2B C0 AA D1   E1 D1 E1 86 CD 8B C1 AB   B8  4  0
1A53   AB B8 76 20 E6   F4 8A C4 E6 F5 2B C0 E6   F7 A2 60
1A63   20 58 50 E6 F2   8A C4 E6 F3 2B C0 E6 F6   B0  1 E6
1A73   F0 E9  E EB 50   1E 8C C8 8E D8 E4 F0 8A   E0 E4 F1
1A83   A3 60 20 57 8B   3E 5E 20 C7  5 FF D7 5F   1F 58 CF
1A93    8 28 42 55 89   19 3A  0 3D  5  D 19 17    A 17  0
1AA3    A 31 1A 3D  5   19 19 4D  0  7 28 42 4C   93 1A 3A
1AB3    0 B1  4 B7  1   88  2 7F  5 DF  9 8F  A   3D  5 2E
1AC3   19 56  2 17  0    8 31 1A 46  2 7B  A 3D    5 19 19
1AD3   4D  0  5 44 52   49 B8 18 3A  0  F  0 68    2 F8  2
1AE3   B1  4 C6  1 4D    0
```

Code for the Redefinition of:

FDC
   FLOPPY
   (BUFFER)
   (BLOCK)

to support Shugart 1403D disk controller for the
main computer (86/12A)

Code in EPROM 0-1FFF is otherwise identical to
FORTH, Inc.'s software product called
86/12-202 PROM polyFORTH.

LISTING NO. 2

Sheet 1

```
2000   C8 20  0 FE CE 19  0 FE   CE 19  0 FE CE 19  0 FE
2010   CE 19  0 FE CE 19  0 FE   CE 19  0 FE CE 19  0 FE
2020   CE 19  0 FE  1 4A  0 FE   FF 27  0 FE FB 69 FA F8
2030   37 6A FA F8 A0 2D  0 FE   28 4A  0 FE 1C DD C1 F2
2040   51  0 7F 36 5D 36 6E 36   E8 35 DE 35 82 26 B5 36
2050   DA 34 51  0 C8 2F AB 2F    0  0 9F 25 87 36  0  0
2060    0 C1  4  0  4  0 A8  1   A4  1 64  0 A9  1  0  0
2070    0  0  0  0  0  0  8  0    5 4C  4  0  0  0  0  0
2080   33 2E 6D  2 2A 7B  0  0    3 4B 45 59 CF 19 3A  0
2090   BA  4 B7  1 8B  3 C0  3   95  3 C7  5 46  2 BA  4
20A0   C6  1 4D  0  4 45 4D 49    E 18 3A  0 C0  3 95  3
20B0   AB  5 38  2 4D  0 F6  7    7 54 52 41 50 50 45 44
20C0   BE B6 20 FB AD 97 FF 25   2B C0 99 CF  9 49 4D 4D
20D0   7A 18 3A  0  F  0 80  0   F0  4 B7  1 B7  1 D5  1
20E0   4D  0  B 44 45 46 D5 1A   3A  0 DE  4 B7  1 E7  4
20F0   C6  1 4D  0  6 46 4F 52   A4 20 3A  0 7F  9 17  0
```

| | | | | | | | | | | | | |
|---|---|---|---|---|---|---|---|---|---|---|---|---|
| 2100 | 8 | 99 | 2 | 28 | 2 | A8 | 4 | C6 | 1 | B9 | 2 | E7 | 4 | DE | 4 | C8 |
| 2110 | 2 | E2 | 0 | 79 | 2 | B7 | 1 | 35 | 4 | 9B | 1 | D6 | 0 | 9 | C8 | 2 |
| 2120 | C8 | 2 | B7 | 1 | CC | 0 | F0 | 79 | 2 | C6 | 1 | 17 | 0 | 2 | 20 | 1 |
| 2130 | E2 | 38 | 2 | 4D | 0 | 6 | 41 | 54 | 54 | 37 | 19 | 3A | 0 | DE | 4 | C8 |
| 2140 | 2 | 17 | 0 | 10 | 1D | 3 | 4D | 0 | 7 | 44 | 49 | 53 | E2 | 20 | 66 | 0 |
| 2150 | 27 | 0 | 8 | 50 | 52 | 49 | E5 | 18 | 66 | 0 | 2A | 0 | 8 | 43 | 4F | 4D |
| 2160 | 48 | 21 | 66 | 0 | 5A | 0 | 6 | 2B | 46 | 4F | 88 | 20 | 66 | 0 | 15 | 0 |
| 2170 | 5 | 54 | 41 | 53 | 5C | 21 | 66 | 0 | 1C | 0 | 9 | 32 | 43 | 4F | 35 | 21 |
| 2180 | 3A | 0 | 5E | 0 | 24 | B | D6 | B | FF | 75 | 4 | FF | 75 | 2 | AD | 97 |
| 2190 | FF | 25 | 2 | 30 | 2E | 20 | 52 | 21 | 88 | 21 | 0 | 0 | 0 | 0 | 5 | 32 |
| 21A0 | 53 | 57 | 7A | 21 | A6 | 21 | 5A | 5F | 58 | 59 | 57 | 52 | 51 | 50 | AD | 97 |
| 21B0 | FF | 25 | 5 | 32 | 4F | 56 | 9E | 21 | BA | 21 | 8B | FC | FF | 75 | 6 | FF |
| 21C0 | 75 | 4 | AD | 97 | FF | 25 | 2 | 44 | 2B | 20 | 70 | 21 | CE | 21 | 5A | 58 |
| 21D0 | 8B | FC | 1 | 45 | 2 | 11 | 15 | AD | 97 | FF | 25 | 6 | 44 | 4D | 49 | C6 |
| 21E0 | 21 | E3 | 21 | 5A | 58 | F7 | D8 | 83 | D2 | 0 | F7 | DA | 50 | 52 | AD | 97 |
| 21F0 | FF | 25 | 2 | 44 | 2D | 20 | DB | 21 | 3A | 0 | E1 | 21 | CC | 21 | 4D | 0 |
| 2200 | 3 | 44 | 30 | 3D | F2 | 21 | 3A | 0 | 61 | 1 | 46 | 2 | 61 | 1 | 2E | 1 |
| 2210 | 4D | 0 | 2 | 44 | 3C | 20 | 0 | 22 | 3A | 0 | F8 | 21 | 85 | 1 | 46 | 2 |
| 2220 | 38 | 2 | 4D | 0 | 4 | 44 | 41 | 42 | 12 | 22 | 3A | 0 | 28 | 2 | 85 | 1 |
| 2230 | D6 | 0 | 2 | E1 | 21 | 4D | 0 | 4 | 44 | 4D | 49 | 24 | 22 | 3A | 0 | B8 |
| 2240 | 21 | F8 | 21 | 28 | 2 | 85 | 1 | D6 | 0 | 5 | CC | 21 | CC | 0 | 2 | 48 |
| 2250 | 4 | 4D | 0 | 4 | 44 | 4D | 41 | 37 | 22 | 3A | 0 | B8 | 21 | B8 | 21 | 3D |
| 2260 | 22 | F8 | 21 | CC | 21 | 4D | 0 | 3 | 4D | 4F | 44 | 50 | 18 | 6F | 22 | 5F |
| 2270 | 2B | D2 | 58 | F7 | F7 | 52 | AD | 97 | FF | 25 | 5 | 2A | 2F | 4D | CC | 20 |
| 2280 | 82 | 22 | 5F | 5A | 58 | F7 | E2 | F7 | F7 | 52 | 50 | AD | 97 | FF | 25 | 2 |
| 2290 | 2A | 2F | 20 | 7A | 22 | 97 | 22 | 5F | 5A | 58 | F7 | EA | F7 | FF | 50 | AD |
| 22A0 | 97 | FF | 25 | 1 | 2F | 20 | 20 | 92 | 21 | AB | 22 | 5F | 58 | 99 | F7 | FF |
| 22B0 | 50 | AD | 97 | FF | 25 | 2 | 4D | 2A | 20 | 67 | 22 | BD | 22 | 58 | 5A | F7 |
| 22C0 | EA | 50 | 52 | AD | 97 | FF | 25 | 2 | 4D | 2F | 20 | B5 | 22 | CF | 22 | 5F |
| 22D0 | 5A | 58 | F7 | FF | 50 | AD | 97 | FF | 25 | 2 | 55 | 2A | 20 | F4 | 20 | E1 |
| 22E0 | 22 | 58 | 5A | F7 | E2 | 50 | 52 | AD | 97 | FF | 25 | 5 | 4D | 2F | 4D | C7 |
| 22F0 | 22 | F3 | 22 | 5F | 5A | 58 | F7 | F7 | 52 | 50 | AD | 97 | FF | 25 | 2 | 4D |
| 2300 | 2B | 20 | EB | 22 | 6 | 23 | 58 | 99 | E9 | C5 | FE | 2 | 54 | 2A | 20 | 53 |
| 2310 | 22 | 13 | 23 | 89 | 76 | FE | 89 | 5E | FC | 5B | 5E | 5F | 8B | C7 | F7 | E3 |
| 2320 | 50 | 8B | CA | 8B | C6 | F7 | E3 | 3 | C8 | 83 | D2 | 0 | B | F6 | 79 | 2 |
| 2330 | 2B | D3 | B | DB | 79 | 4 | 2B | CF | 1B | D6 | 51 | 52 | 8B | 5E | FC | 8B |
| 2340 | 76 | FE | AD | 97 | FF | 25 | 2 | 54 | 2F | 20 | B | 23 | 4E | 23 | 5F | 5A |
| 2350 | 58 | 59 | B | FF | 9C | 79 | 2 | F7 | DF | B | D2 | 79 | 2 | 3 | D7 | F7 |
| 2360 | F7 | 91 | F7 | F7 | 9D | 79 | 7 | F7 | D8 | 83 | D1 | 0 | F7 | D9 | 50 | 51 |
| 2370 | AD | 97 | FF | 25 | 3 | 4D | 2A | 2F | FE | 22 | 3A | 0 | 6 | 2 | 11 | 23 |
| 2380 | 17 | 2 | 4C | 23 | 4D | 0 | A | 42 | 41 | 43 | B2 | 21 | 3A | 0 | FF | B |
| 2390 | 6 | 2 | 56 | 2 | 88 | 2 | 28 | 2 | 4 | 6 | AA | 2 | 88 | 2 | 17 | 0 |
| 23A0 | F | 2E | 1 | 17 | 0 | F | 50 | 1 | 28 | 2 | CC | 21 | 28 | 2 | 4 | 6 |
| 23B0 | C8 | 2 | 88 | 2 | 24 | B | 46 | 2 | 4 | 6 | 88 | 2 | 24 | B | 79 | 2 |
| 23C0 | 12 | B | 17 | 2 | 88 | 2 | 17 | 0 | 3 | 99 | 2 | F6 | A | 4D | 0 | 5 |
| 23D0 | 42 | 55 | 49 | 86 | 23 | 3A | 0 | EB | 18 | B7 | 1 | 56 | 2 | 28 | 2 | B7 |
| 23E0 | 1 | 46 | 2 | C8 | 2 | C8 | 2 | E5 | 1 | 1D | 3 | 12 | 4 | 28 | 2 | EB |
| 23F0 | 18 | B7 | 1 | C8 | 2 | C6 | 1 | 17 | 0 | 8 | 88 | 2 | C6 | 1 | 4D | 0 |

LISTING NO. 2

Sheet 2

| | | | | | | | | | | | | | | | | |
|---|---|---|---|---|---|---|---|---|---|---|---|---|---|---|---|---|
| 2400 | 8 | 54 | 45 | 52 | 46 | 23 | 3A | 0 | FF | B | 17 | 0 | 19 | 2 | E | 4D |
| 2410 | 0 | 9 | 43 | 4F | 4E | 0 | 24 | 3A | 0 | 28 | 2 | D5 | 23 | 28 | 2 | 17 |
| 2420 | 0 | 5 | 88 | 2 | 46 | 2 | B7 | 1 | F | 0 | E | 0 | 88 | 2 | 17 | 0 |
| 2430 | 10 | 1D | 3 | 4D | 0 | 6 | 50 | 52 | 4F | A3 | 22 | 3A | 0 | 3D | 19 | 94 |
| 2440 | D | F4 | 5 | 15 | 8 | 2 | 75 | 70 | E4 | 5 | 8B | 3 | C6 | 9 | 4 | 53 |
| 2450 | 45 | 4E | 11 | 24 | 3A | 0 | 28 | 2 | B7 | 1 | 60 | 4 | B7 | 1 | 56 | 2 |
| 2460 | F | 0 | 8 | 0 | 88 | 2 | B7 | 1 | 17 | 0 | 50 | 1D | 3 | B1 | 4 | 46 |
| 2470 | 2 | F | 0 | 1E | 0 | 88 | 2 | 17 | 0 | 42 | 1D | 3 | CC | 4 | B7 | 1 |
| 2480 | BA | 4 | C6 | 1 | 3D | 19 | 8B | 3 | 8F | 9 | C6 | 9 | 9 | 28 | 41 | 53 |
| 2490 | AC | 1A | 3A | 0 | 17 | 2 | C8 | 2 | 46 | 2 | C6 | 1 | 4D | 0 | 86 | 41 |

```
24A0   53 53 CF 23 3A  0 37  B    92 24 37  B 3A  0 4D  0
24B0    5 49 4E 50 8F 22 B8 24    5A 2B C0 EC 50 AD 97 FF
24C0   25  6 4F 55 54 35 24 C9    24 5A 58 EE AD 97 FF 25
24D0    6 2F 44 49 C1 24 D8 24    58 59 2B D2 F7 77 22 91
24E0   F7 77 22 50 51 52 AD 97    FF 25  1 23 20 20 4E 24
24F0   3A  0 D6 24 A2  6 8E  6    4D  0  2 23 53 20 EA 24
2500   3A  0 F0 24 35  4  6 22    D6  0 F7 4D  0  4 28 44
2510   2E 8C 24 3A  0 46  2 56     2 2A 22 B8  6  0 25 DE
2520    6 C8  6 4D  0  2 44 2E    20 FA 24 3A  0 13 25 AB
2530    5 80  6 4D  0  3 44 2E    52 25 25 3A  0  6  2 13
2540   25 17  2 56  2 99  2 6C     6 AB  5 4D  0  6 2A 44
2550   49 B0 24 55 25 5F 5A 58    59 52 F7 67 22 91 F7 67
2560   22  3 C7 13 CA 5A 50 51    52 AD 97 FF 25  6 57 49
2570   54  D 25 75 25 5A 59 58    2B FF 3B C2 79  5 3B C1
2580   78  1 47 57 AD 97 FF 25     3 2B 49 27 66 21 90 25
2590   FF 46  2 AD 97 FF 25  8    28 4E 55 6D 25 3A  0 8B
25A0    3  6  2 28  2 AA  2 E5     1 17  0 2D 77  1 28  2
25B0    6  2 88  2 98 21 67  2    F5  8 D6  0  5 53 25 CC
25C0    0 F6 28  2 E5  1 28  2    17  0 3A 77  1 46  2 17
25D0    0 2C 17  0 30 73 25 88     2 D6  0  5 8E 25 CC  0
25E0   D7 E5  1 17  0 20 99  2    F6  7  1 3F 17  2 D6  0
25F0    2 E1 21 17  2 61  1 D6     0  2 38  2 4D  0  3 44
2600   2F 59 35 25 66  0 B5  5     4 4A 41 4E 4D 25 99  0
2610   A7 2D  4 4C 45 41 88 25    99  0  0  0  3 4D 54 48
2620   74 23 3A  0 5E  0 D6  B    E8 75 DA B7  1 17  0 3A
2630   56  2 9B  1 18 26 B7  1    F8  2 88  2  E 26 B7  1
2640   88  2 88  2 4D  0  3 4A    41 4E  8 26 28 26  0  0
2650    3 46 45 42 D9 22 28 26    1F  0  3 4D 41 52 1C 26
2660   28 26 3B  0  3 41 50 52    9E 24 28 26 5A  0  3 4D
2670   41 59 5A 26 28 26 78  0     3 4A 55 4E 46 26 28 26
2680   97  0  3 4A 55 4C 78 26    28 26 B5  0  3 41 55 47
2690   64 26 28 26 D4  0  3 53    45 50 FE 25 28 26 F3  0
26A0    3 4F 43 54 D0 24 28 26    11  1  3 4E 4F 56 6E 26
26B0   28 26 30  1  3 44 45 43    96 26 28 26 4E  1  2 41
26C0   44 20 8C 26 3A  0  F  0    9D  7 99  2  4 26 17  0
26D0    4 80 22  F  0 6E  1 99     2  E 26 C6  1 17  0  3
26E0   77  1 18 26 C6  1 4D  0     3 2E 59 52 AA 26 3A  0
26F0    F  0 DB  2 88  2 17  0     4  4 26 80 22  F  0 9C
2700    7 88  2 46  2 17  0  4     9  3 AA  2 28  2 67  2
2710   61  1 D6  0 14 28  2 17     0 3C A9  1 99  2 46  2
2720   28  2 17  0 3B A9  1 99     2 67  2 4D  0  4 2E 4D
2730   54 E8 26 3A  0  F  0 4E    26 17  0  B 8B  3 E2  0
2740   35  4 17  0  A 88  2 B7     1 A9  1 D6  0  A 17  0
2750    A 88  2 95  3 CC  0  3    17  0  B 20  1 E2 46  2
2760   38  2 28  2 17  0  8 99     2  6  2 B7  1 99  2 17
2770    2 4D  0  2 27 27 20 97    25 3A  0 17  0 20 8E  6
2780   4D  0  6 28 44 41 73 27    3A  0 B8  6 EE 26 8B  3
2790   F0 24 F0 24 F0 24 F0 24    48  4 79 27 33 27 17  0
27A0   FD 72  4 D5  1 25  6 72     4 B7  1 46  2 1D  3 79
27B0   27 8B  3  0 25 C8  6 4D     0  5 2E 44 41 2D 27 3A
27C0    0 CF  3 D6  0  9 88 27    AB  5 80  6 CC  0  E 15
27D0    8  B 44 59 20 4D 54 48    20 4E 4F 57 20 4D  0  5
27E0   54 4F 44 B4 26 66  0 80    20  5 54 49 43 DF 27 66
27F0    0 82 20  4 31 44 41 BE    26 88 21 1E  4  0 B0 9C
```

LISTING NO. 2

Sheet 3

```
2800   50 1E B8  0 FE 8E D8 FF     6 84 20 75  4 FF  6 82
2810   20 1F 58 9D CF  5 43 4C    4F E9 27 1D 28 E4 C2 24
2820   FB E6 C2 AD 97 FF 25  6    2D 43 4C E9 27 2F 28 E4
2830   C2  C  4 E6 C2 AD 97 FF    25  7 43 4F 55 15 28 41
```

```
2840    28 FF 36 84 20 AD 97 FF    25  5 54 49 4D 39 28 3A
2850     0 3F 28 46  2 99  2 17     0  A 17  0  8 95 22 35
2860     7 4D  0  2 4D 53 20 27    28 3A  0 3F 28 46  2 17
2870     0  8 17  0  A 95 22 88     2 7F  5 28  2 3F 28 9B
2880     1 D6  0 F5 38  2 4D  0     3 50 53 54 A0 26 3A  0
2890    2D 28 17  0 64 F1 22 17     0 3C F8  2 88  2  F  0
28A0    80 BB DF 22 EF 27 24  4    1B 28 4D  0  5 40 54 49
28B0    88 28 3A  0 2D 28 F9 27    EF 27 12  4 B8 21 F8 21
28C0    28  2 85  1 61  3 D6  0     9 95  3 E5 27 D5  1 CC
28D0     0 EA CC 21 35  4 EF 27    24  4 1B 28 4D  0  5 2E
28E0    54 49 63 28 3A  0 8B  3    B8  6 F0 24 17  0  6 C3
28F0     4 C6  1 F0 24 E0  D 17     0 3A 8E  6 F0 24 F0 24
2900    C8  6 4D  0  4 54 49 4D    49 28 3A  0 B2 28  F  0
2910    80 BB F1 22 E4 28 AB  5    80  6 38  2 4D  0  3 4E
2920    4F 57 DE 28 3A  0 E5 27    C6  1 4D  0 9C 50 53 1E
2930    B8  0 FE 8E D8 8C CB D1    E3 D1 E3 D1 E3 D1 E3 8B
2940    47  A 48 78 23 89 47  A    75  6 C7  7 FF D7 EB 18
2950    52 87 77  C 8B 57 14 AC    87 77  C EE 82 C2  4 B8
2960     2  0 EE 90 90 40 EE 5A    1F 5B 58 9D CF  7 28 50
2970    52 82 27 75 29 8B 57 14    FF 47  A CD  F E9  5 DC
2980     7 50 52 49 AC 28 99  0    10 2C  2 54 54 20 20 20
2990    20 20 19 CA  0 C8  0 7E    19 8A 29 8A 29  5 41 4C
29A0    4C 4F 54 20 20 20  8 32    39 33 33 6E 27 74 20 75
29B0    6E 69 71 75 65 20 38  2    CC  4 C6  1 73  0 4D  0
29C0     7 2E 43 52 1E 29 3A  0    E4  5 15  8  5 20 20 20
29D0    20 20 CC  4 B7  1 17  0    20 75  8 25  6 AB  5 C3
29E0     4 B7  1 F1  D  4  6 80     6 53  7 C3  4 C6  1 CC
29F0     4 C6  1 73  0 4D  0  4    4C 4F 41 12 26 3A  0 E4
2A00     5 15  8  4 20 20 20 20    28  2 35  7  2  E 4D  0
2A10     4 46 49 4C 50 26 18 2A    58 8A F0 F9 85 D9  5 4E
2A20    46 49 C0 29 3A  0 67  2    67  2 D8  2 56  2 88  2
2A30    46  2 E2  0 28  2 79  2    C6  1 17  0  2  7  1 F4
2A40    38  2 4D  0  4 50 55 4D    8A 29 3A  0 56  2 88  2
2A50    46  2 E2  0 79  2 F7  1    F1  0 F9 4D  0  5 4E 50
2A60    55 1E 2A 3A  0 D8  2 56     2 88  2 46  2 E2  0 79
2A70     2 C6  1 17  0  2  7  1    F6 4D  0 85 4C 41 42 F7
2A80    29 3A  0 FF  B 36  D 4D     0  2 43 3B 20  4 29 3A
2A90     0 E7  4 B7  1 DE  4 C6     1 4D  0  2 3E 3C 20 5D
2AA0    2A A3 2A 59 86 CD 51 AD    97 FF 25  3 2B 43 40 7B
2AB0    2A B3 2A 5F 8B  D 8A CD    2A ED 51 AD 97 FF 25  3
2AC0    2B 43 21 AB 2A C7 2A 5F    58 47 AA AD 97 FF 25  3
2AD0    44 54 43 89 2A 66  0 F0     0  2 52 44 20 F3 27 66
2AE0     0  8  0  2 57 52 20 6D    29 66  0  A  0  6 54 4F
2AF0    50 CF 2A 99  0  0  0  5    57 49 4E E3 2A 99  0  0
2B00     0  3 43 44 42 ED 2A 99     0  8  0  0 58  4  0 4F
2B10    54 20 20  A 53 45 4E  1    2B 99  0 4F 43  5 41 9C
2B20    50 1E B8  0 FE 8E D8 E4    F0 8A E0 E4 F1 A3 60 20
2B30    57 8B 3E 5E 20 C7  5 FF    D7 5F 1F 58 9D CF  8 44
2B40    54 43 13 2B 46 2B B8  9    2B E6 F4 8A C4 E6 F5 2B
2B50    C0 E6 F7 A2 60 20 58 50    E6 F2 8A C4 E6 F3 8B  6
2B60    F5 2A E6 F6 B0  1 E6 F0    E9 1A DA  3 57 44 43 F7
2B70    2A 3A  0  7 CA  0  0 FE    CA 2C CA  0  0 FE 10 2C
2B80     6  0  2 F0 A0 2C  1  0    75  0 40  6 8C 2B  0  0
2B90    50 52 49 4E 54 20 37 30    30 30 20 32 30 30 30 20
2BA0    54 54 20 50 20 20 43 52    20 43 52 20 20 34 30 30
2BB0    20 2B 4C 4F 4F 50 20 3B    20 43 52 20 43 32 35 36
2BC0    20 20 53 4D 4F 56 45 4C    4F 41 44 20 43 52 50 54
2BD0    59 2D 42 55 46 46 45 52    53 FF FF FF D2  6 86  6
2BE0     8 16 20 20 20 44 49 53    4B 20 45 52 52 4F 52 3A
2BF0    20 20 20 54 59 50 45 20    D2  6 7D  7 B8  7 FE 2B
```

LISTING NO. 2

Sheet 4

| Addr | | | | | | | | | | | | | | | | |
|------|----|----|----|----|----|----|----|----|----|----|----|----|----|----|----|----|
| 2C00 | 10 | 2C | 0 | 2C | 0 | 30 | 5F | 6C | 0 | 2C | 0 | 70 | 9D | 9 | 8A | 24 |
| 2C10 | 2E | EA | A0 | 8F | 0 | FE | 8A | 2B | 90 | 2B | 0 | 0 | 40 | 6 | 86 | 19 |
| 2C20 | 86 | 19 | 75 | 29 | CA | 0 | C8 | 0 | 7E | 19 | 8A | 29 | 8A | 29 | 0 | 0 |
| 2C30 | 12 | 0 | 10 | 0 | 12 | 0 | 0 | 0 | 51 | 0 | B0 | 6B | 37 | 6C | 4D | 6C |
| 2C40 | 1C | 66 | A9 | 68 | 53 | 66 | A0 | 6B | 8F | 6B | 51 | 0 | CE | 8F | 15 | 0 |
| 2C50 | 0 | 0 | 0 | 0 | 0 | 0 | 0 | 0 | 0 | 0 | 0 | 0 | 0 | 0 | 0 | 0 |
| 2C60 | 0 | 0 | 0 | 0 | 0 | 0 | 0 | 0 | 0 | 0 | 0 | 0 | 0 | 0 | 0 | 0 |
| 2C70 | 0 | 6 | 3F | 45 | 52 | 44 | 2A | 3A | 0 | 3D | 5 | C8 | 2 | E5 | 1 | 17 |
| 2C80 | 0 | 3 | 2E | 5 | 50 | 52 | 49 | 80 | 29 | 3A | 0 | 86 | 29 | 54 | 24 | 4D |
| 2C90 | 0 | 4 | 46 | 49 | 4C | 50 | 26 | 99 | 2C | 58 | 8A | E0 | E9 | 4 | D7 | 5 |
| 2CA0 | 4E | 46 | 49 | 1E | 29 | 3A | 0 | 67 | 2 | 67 | 2 | D8 | 2 | 56 | 2 | 88 |
| 2CB0 | 2 | 46 | 2 | E2 | 0 | 28 | 2 | 79 | 2 | C6 | 1 | 17 | 0 | 2 | 7 | 1 |
| 2CC0 | F4 | 38 | 2 | 4D | 0 | 4 | 50 | 55 | 4D | 83 | 2C | 3A | 0 | 56 | 2 | 88 |
| 2CD0 | 2 | 46 | 2 | E2 | 0 | 79 | 2 | F7 | 1 | F1 | 0 | F9 | 4D | 0 | 5 | 4E |
| 2CE0 | 50 | 55 | 9F | 2C | 3A | 0 | D8 | 2 | 56 | 2 | 88 | 2 | 46 | 2 | E2 | 0 |
| 2CF0 | 79 | 2 | C6 | 1 | 17 | 0 | 2 | 7 | 1 | F6 | 4D | 0 | 85 | 4C | 41 | 42 |
| 2D00 | 12 | 26 | 3A | 0 | FF | B | 36 | D | 4D | 0 | 2 | 43 | 3B | 20 | 4 | 29 |
| 2D10 | 3A | 0 | E7 | 4 | B7 | 1 | DE | 4 | C6 | 1 | 4D | 0 | 2 | 3E | 3C | 20 |
| 2D20 | DE | 2C | 24 | 2D | 59 | 86 | CD | 51 | AD | 97 | FF | 25 | 3 | 2B | 43 | 40 |
| 2D30 | FC | 2C | 34 | 2D | 5F | 8B | D | 8A | CD | 2A | ED | 51 | AD | 97 | FF | 25 |
| 2D40 | 3 | 2B | 43 | 21 | 2C | 2D | 48 | 2D | 5F | 58 | 47 | AA | AD | 97 | FF | 25 |
| 2D50 | 3 | 44 | 54 | 43 | A | 2D | 66 | 0 | F0 | 0 | 2 | 52 | 44 | 20 | F3 | 27 |
| 2D60 | 66 | 0 | 8 | 0 | 2 | 57 | 52 | 20 | 6D | 29 | 66 | 0 | A | 0 | 6 | 54 |
| 2D70 | 4F | 50 | 50 | 2D | 99 | 0 | 0 | 0 | 5 | 57 | 49 | 4E | 64 | 2D | 99 | 0 |
| 2D80 | 0 | 0 | 3 | 43 | 44 | 42 | 6E | 2D | 99 | 0 | 8 | 0 | 1 | 90 | 4 | 0 |
| 2D90 | 4F | 54 | 20 | 20 | A | 53 | 45 | 4E | 82 | 2D | 99 | 0 | 4F | 43 | 5 | 41 |
| 2DA0 | 9C | 50 | 1E | B8 | 0 | FE | 8E | D8 | E4 | F0 | 8A | E0 | E4 | F1 | A3 | 60 |
| 2DB0 | 20 | 57 | 8B | 3E | 5E | 20 | C7 | 5 | FF | D7 | 5F | 1F | 58 | 9D | CF | 8 |
| 2DC0 | 44 | 54 | 43 | 94 | 2D | C7 | 2D | B8 | 8A | 2D | E6 | F4 | 8A | C4 | E6 | F5 |
| 2DD0 | 2B | C0 | E6 | F7 | A2 | 60 | 20 | 58 | 50 | E6 | F2 | 8A | C4 | E6 | F3 | 8B |
| 2DE0 | 6 | 76 | 2D | E6 | F6 | B0 | 1 | E6 | F0 | E9 | 99 | D7 | 3 | 57 | 44 | 43 |
| 2DF0 | 78 | 2D | 3A | 0 | 88 | 2D | 56 | 2 | 17 | 0 | 20 | 77 | 1 | D6 | 0 | 6 |
| 2E00 | 17 | 0 | A | CC | 0 | 3 | 17 | 0 | 6 | CB | 2C | C5 | 2D | 4D | 0 | 5 |
| 2E10 | 53 | 45 | 4E | BF | 2D | 3A | 0 | 3D | 5 | C8 | 2 | E5 | 1 | 6 | 2 | 9A |
| 2E20 | 2D | 8B | 3 | 28 | 2 | 35 | 4 | 79 | 2 | 17 | 0 | 3 | F2 | 2D | 17 | 2 |
| 2E30 | 48 | 4 | 4D | 0 | B | 52 | 45 | 43 | 5A | 2D | 3A | 0 | 3D | 5 | C8 | 2 |
| 2E40 | E5 | 1 | 6 | 2 | 9A | 2D | 8B | 3 | 28 | 2 | 35 | 4 | 79 | 2 | 95 | 3 |
| 2E50 | F2 | 2D | 17 | 2 | 48 | 4 | 4D | 0 | 6 | 2E | 53 | 45 | 1C | 2D | 3A | 0 |
| 2E60 | 15 | 8 | 16 | 20 | 20 | 20 | 44 | 49 | 53 | 4B | 20 | 45 | 52 | 52 | 4F | 52 |
| 2E70 | 3A | 20 | 20 | 20 | 54 | 59 | 50 | 45 | 20 | 9A | 2D | 28 | 2 | E5 | 1 | 46 |
| 2E80 | 2 | 56 | 2 | 28 | 2 | 17 | 0 | 30 | 2E | 1 | 17 | 0 | 10 | A9 | 22 | 35 |
| 2E90 | 7 | 15 | 8 | 8 | 20 | 20 | 20 | 43 | 4F | 44 | 45 | 20 | 17 | 0 | F | 2E |
| 2EA0 | 1 | 35 | 7 | 15 | 8 | 7 | 20 | 20 | 20 | 4C | 55 | 4E | 20 | AA | 2 | 28 |
| 2EB0 | 2 | E5 | 1 | 17 | 0 | 60 | 2E | 1 | 17 | 0 | 20 | A9 | 22 | 35 | 7 | 46 |
| 2EC0 | 2 | F | 0 | 80 | 0 | 2E | 1 | 61 | 1 | D6 | 0 | 5 | 38 | 2 | CC | 0 |
| 2ED0 | 1A | 15 | 8 | A | 20 | 20 | 20 | 53 | 45 | 43 | 54 | 4F | 52 | 20 | AA | 2 |
| 2EE0 | B7 | 1 | 22 | 2D | 53 | 7 | 17 | 0 | 3 | 6C | 6 | 17 | 0 | 3 | 6C | 6 |
| 2EF0 | 4D | 0 | 6 | 3F | 45 | 52 | C5 | 2C | 3A | 0 | 3D | 5 | C8 | 2 | E5 | 1 |
| 2F00 | 17 | 0 | 3 | 2E | 1 | 61 | 1 | 61 | 3 | 4D | 0 | 5 | 45 | 52 | 52 | 91 |
| 2F10 | 2C | 3A | 0 | F8 | 2E | D6 | 0 | 54 | 17 | 0 | A | 8B | 3 | E2 | 0 | 88 |
| 2F20 | 2D | 88 | 2D | 17 | 0 | 5 | 88 | 2 | E2 | 0 | 79 | 2 | E5 | 1 | 17 | 0 |
| 2F30 | FF | 7 | 1 | F6 | F2 | 2D | F8 | 2E | 61 | 3 | D6 | 0 | 2 | 0 | 4 | F1 |
| 2F40 | 0 | DD | F8 | 2E | D6 | 0 | 25 | 17 | 0 | 7 | AA | 20 | C3 | 4 | B7 | 1 |
| 2F50 | F1 | D | 74 | 2D | B7 | 1 | 8B | 3 | 74 | 2D | C6 | 1 | 15 | 2E | E4 | 5 |
| 2F60 | 5E | 2E | 3A | 2E | 74 | 2D | C6 | 1 | C3 | 4 | C6 | 1 | 4D | 0 | 7 | 43 |
| 2F70 | 44 | 42 | F | 2E | 3A | 0 | 8B | 3 | 17 | 0 | 4 | 67 | 2 | 28 | 2 | 17 |
| 2F80 | 0 | 4 | F8 | 2 | 28 | 2 | 22 | 2D | 67 | 2 | F | 0 | 67 | 2 | A9 | 1 |
| 2F90 | D6 | 0 | 6 | 17 | 0 | 20 | CC | 0 | 2 | 8B | 3 | 7E | 2D | B7 | 1 | 3F |
| 2FA0 | 1 | 4D | 0 | 8 | 5B | 42 | 55 | 40 | 2D | 3A | 0 | 3D | 5 | D | 19 | 17 |

| | | | | | | | | | | | | | |
|---|---|---|---|---|---|---|---|---|---|---|---|---|---|
| 2FB0 | A | 74 | 2F | 17 | 0 | A | F2 | 2D | 11 | 2F | 3D | 5 | 19 | 19 | 4D | 0 |
| 2FC0 | 7 | 5B | 42 | 4C | A3 | 2F | 3A | 0 | E1 | 4 | B7 | 1 | 88 | 2 | 7F | 5 |
| 2FD0 | DF | 9 | 8F | A | 3D | 5 | 2E | 19 | 56 | 2 | 74 | 2F | 17 | 0 | 8 | F2 |
| 2FE0 | 2D | 11 | 2F | 46 | 2 | 7B | A | 3D | 5 | 19 | 19 | 4D | 0 | 2 | 46 | 3A |
| 2FF0 | 20 | B | 2F | 3A | 0 | 8B | 3 | 7E | 2D | C6 | 1 | 4D | 0 | 2 | 57 | 3A |

LISTING NO. 2

Sheet 5

| | | | | | | | | | | | | | |
|---|---|---|---|---|---|---|---|---|---|---|---|---|---|
| 3000 | 20 | EC | 2D | 3A | 0 | 17 | 0 | 20 | 7E | 2D | C6 | 1 | 4D | 0 | 3 | 53 |
| 3010 | 43 | 40 | 6E | 2F | 16 | 30 | 8C | DA | 5F | 1F | 2B | C0 | 8A | 5 | 50 | 8E |
| 3020 | DA | AD | 97 | FF | 25 | 2 | 53 | 40 | 20 | E | 30 | 2D | 30 | 8C | DA | 5F |
| 3030 | 1F | 8A | 5 | 47 | 8A | 25 | 50 | 8E | DA | AD | 97 | FF | 25 | 3 | 53 | 43 |
| 3040 | 21 | 25 | 30 | 45 | 30 | 8C | C2 | 5F | 7 | 58 | AA | 8E | C2 | AD | 97 | FF |
| 3050 | 25 | 2 | 53 | 21 | 20 | 3D | 30 | 59 | 30 | 8C | C2 | 5F | 7 | 58 | AA | 8A |
| 3060 | C4 | AA | 8E | C2 | AD | 97 | FF | 25 | 5 | 53 | 4D | 4F | 51 | 30 | 70 | 30 |
| 3070 | 59 | 5F | 8C | D8 | 8C | C2 | 89 | 76 | FE | 7 | 5E | 1F | 50 | F3 | A4 | 1F |
| 3080 | 8E | C2 | 8B | 76 | FE | AD | 97 | FF | 25 | 4 | 50 | 49 | 43 | F2 | 2E | 91 |
| 3090 | 30 | 8B | FC | 58 | D1 | E0 | 3 | F8 | FF | 35 | AD | 97 | FF | 25 | 4 | 52 |
| 30A0 | 4F | 4C | 34 | 2E | 3A | 0 | 28 | 2 | D8 | 2 | 6 | 2 | 8F | 30 | C0 | 3 |
| 30B0 | 28 | 2 | C8 | 2 | 17 | 2 | 74 | E | 38 | 2 | 4D | 0 | 5 | 35 | 55 | 53 |
| 30C0 | ED | 2F | C4 | 30 | 59 | 87 | C8 | 87 | C8 | 87 | C8 | 87 | C8 | E2 | F6 | AD |
| 30D0 | 97 | FF | 25 | 4 | 4D | 53 | 45 | 58 | 2E | 3A | 0 | F | 0 | C8 | 0 | F8 |
| 30E0 | 2 | C2 | 30 | 4D | 0 | 4 | 42 | 45 | 4C | 9E | 30 | 3A | 0 | 17 | 0 | 7 |
| 30F0 | AA | 20 | 4D | 0 | 5 | 51 | 55 | 45 | E5 | 30 | 3A | 0 | 60 | 4 | B7 | 1 |
| 3100 | 17 | 0 | 50 | C7 | 5 | 4D | 0 | 2 | 4E | 3F | 20 | D3 | 30 | 3A | 0 | FA |
| 3110 | 30 | 8B | 3 | CC | 4 | C6 | 1 | 17 | 0 | 20 | 75 | 8 | 5C | 9 | 4D | 0 |
| 3120 | 4 | 3C | 4E | 3C | C0 | 2F | 3A | 0 | 15 | 8 | 4 | 20 | 20 | 5B | 20 | 95 |
| 3130 | 3 | 8F | 30 | 53 | 7 | 15 | 8 | 6 | 3C | 20 | 4E | 20 | 3C | 20 | 17 | 0 |
| 3140 | 2 | 8F | 30 | 53 | 7 | 15 | 8 | 3 | 5D | 20 | 20 | D | 31 | 17 | 0 | 2 |
| 3150 | 8F | 30 | 56 | 2 | 9B | 1 | 61 | 1 | 17 | 0 | 4 | 8F | 30 | 17 | 0 | 3 |
| 3160 | 8F | 30 | 9B | 1 | 3F | 1 | 28 | 2 | D6 | 0 | 8 | 46 | 2 | 38 | 2 | EB |
| 3170 | 30 | E4 | 5 | 61 | 1 | D6 | 0 | B0 | 67 | 2 | 67 | 2 | 48 | 4 | 4D | 0 |
| 3180 | 4 | 42 | 49 | 54 | F4 | 30 | 88 | 31 | 58 | B9 | 8 | 0 | D0 | C0 | BA | 1 |
| 3190 | 0 | 23 | D0 | 52 | E2 | F6 | AD | 97 | FF | 25 | 4 | 53 | 54 | 49 | 68 | 30 |
| 31A0 | A2 | 31 | 58 | B9 | 8 | 0 | BA | 1 | 0 | 23 | D0 | 52 | D0 | C8 | E2 | F6 |
| 31B0 | AD | 97 | FF | 25 | 8 | 4D | 4F | 56 | 7 | 31 | 3A | 0 | 28 | 2 | 6 | 2 |
| 31C0 | 3F | 3 | B9 | 2 | 2E | 1 | 46 | 2 | 17 | 2 | 2E | 1 | 3F | 1 | 4D | 0 |
| 31D0 | 5 | 21 | 42 | 49 | 80 | 31 | 3A | 0 | 28 | 2 | 6 | 2 | B7 | 1 | 46 | 2 |
| 31E0 | BA | 31 | 17 | 2 | C6 | 1 | 4D | 0 | 7 | 53 | 43 | 21 | 9A | 31 | 3A | 0 |
| 31F0 | 35 | 4 | 6 | 2 | 6 | 2 | 14 | 30 | 46 | 2 | BA | 31 | 17 | 2 | 17 | 2 |
| 3200 | 43 | 30 | 4D | 0 | 4 | 4D | 41 | 53 | B4 | 31 | C | 32 | FA | 59 | E4 | C2 |
| 3210 | B | C1 | E6 | C2 | FB | AD | 97 | FF | 25 | 6 | 55 | 4E | 4D | BC | 30 | 21 |
| 3220 | 32 | FA | 59 | F6 | D1 | 48 | E4 | C2 | 23 | C1 | E6 | C2 | FB | AD | 97 | FF |
| 3230 | 25 | 4 | 48 | 41 | 4C | FD | 2F | 39 | 32 | F4 | AD | 97 | FF | 25 | 5 | 56 |
| 3240 | 53 | 59 | 19 | 32 | 3A | 0 | 17 | 0 | 40 | 1F | 32 | 37 | 32 | 17 | 0 | 40 |
| 3250 | A | 32 | 4D | 0 | 6 | 56 | 53 | 59 | 3E | 32 | 3A | 0 | 8B | 3 | E2 | 0 |
| 3260 | 44 | 32 | F1 | 0 | FB | 4D | 0 | 4 | 3F | 4B | 45 | 89 | 30 | 6F | 32 | B8 |
| 3270 | A | 0 | E6 | C0 | E4 | C0 | 25 | 10 | 0 | 50 | AD | 97 | FF | 25 | 7 | 4B |
| 3280 | 45 | 59 | 20 | 31 | 3A | 0 | 8E | 20 | 38 | 2 | 4D | 0 | 5 | 44 | 32 | 35 |
| 3290 | E8 | 31 | 94 | 32 | 58 | 5A | D1 | F8 | D1 | DA | D1 | F8 | D1 | DA | D1 | F8 |
| 32A0 | D1 | DA | D1 | F8 | D1 | DA | D1 | F8 | D1 | DA | D1 | F8 | D1 | DA | D1 | F8 |
| 32B0 | D1 | DA | D1 | F8 | D1 | DA | 52 | 50 | AD | 97 | FF | 25 | 3 | 44 | 32 | 2F |
| 32C0 | 8C | 32 | C4 | 32 | 58 | 5A | D1 | F8 | D1 | DA | 52 | 50 | AD | 97 | FF | 25 |
| 32D0 | 4 | 53 | 2D | 3E | BC | 32 | D8 | 32 | 58 | 99 | 50 | 52 | AD | 97 | FF | 25 |
| 32E0 | 2 | 2B | 2D | 20 | 7E | 32 | E8 | 32 | 5A | 59 | B | D2 | 79 | 2 | F7 | D9 |
| 32F0 | 51 | AD | 97 | FF | 25 | 2 | 44 | 2F | 20 | D0 | 32 | FD | 32 | 59 | 5A | 58 |
| 3300 | F7 | F1 | 50 | AD | 97 | FF | 25 | 2 | 44 | 2A | 20 | F5 | 32 | F | 33 | 58 |
| 3310 | 59 | F7 | E1 | 50 | 52 | AD | 97 | FF | 25 | 2 | 54 | 2B | 20 | 7 | 33 | 21 |
| 3320 | 33 | 5A | 59 | 58 | 8B | FC | 1 | 45 | 4 | 11 | 4D | 2 | 11 | 15 | AD | 97 |
| 3330 | FF | 25 | 6 | 54 | 4D | 49 | 19 | 33 | 3A | 33 | 5A | 59 | 58 | F7 | D8 | 83 |
| 3340 | D1 | 0 | F7 | D9 | 83 | D2 | 0 | F7 | DA | 50 | 51 | 52 | AD | 97 | FF | 25 |
| 3350 | 2 | 54 | 2D | 20 | 32 | 33 | 3A | 0 | 38 | 33 | 1F | 33 | 4D | 0 | 2 | 54 |

| | | | | | | | | | | | | | |
|---|---|---|---|---|---|---|---|---|---|---|---|---|---|
| 3360 | 3C | 20 | 50 | 33 | 3A | 0 | 56 | 33 | 85 | 1 | 46 | 2 | 38 | 2 | 46 | 2 |
| 3370 | 38 | 2 | 4D | 0 | 5 | 43 | 4C | 45 | 5E | 33 | 3A | 0 | F9 | 4 | B7 | 1 |
| 3380 | 9E | A | 28 | 2 | 8B | 3 | 46 | 2 | C6 | 1 | C8 | 2 | F | 0 | FE | 3 |
| 3390 | 38 | 6 | 66 | A | 4D | 0 | 6 | 43 | 4C | 45 | 74 | 33 | 3A | 0 | E2 | 0 |
| 33A0 | 79 | 2 | F9 | 4 | C6 | 1 | 7A | 33 | F1 | 0 | F5 | 4D | 0 | 2 | 2E | 52 |
| 33B0 | 20 | 4 | 32 | 3A | 0 | 6 | 2 | D6 | 32 | 17 | 2 | 3B | 25 | 4D | 0 | 5 |
| 33C0 | 4E | 44 | 55 | AD | 33 | 3A | 0 | 8B | 3 | E2 | 0 | E4 | 5 | 28 | 2 | 17 |
| 33D0 | 0 | 8 | B3 | 33 | 17 | 0 | 8 | 8B | 3 | E2 | 0 | 28 | 2 | B7 | 1 | 17 |
| 33E0 | 0 | 8 | B3 | 33 | 17 | 0 | 2 | 88 | 2 | F1 | 0 | EF | 17 | 0 | 8 | 7 |
| 33F0 | 1 | D9 | 38 | 2 | 4D | 0 | 5 | 44 | 45 | 50 | 96 | 33 | 3A | 0 | 60 | 4 |

LISTING NO. 2

Sheet 6

| | | | | | | | | | | | | | |
|---|---|---|---|---|---|---|---|---|---|---|---|---|---|
| 3400 | B7 | 1 | C0 | 3 | 99 | 2 | E8 | 2 | 17 | 0 | 2 | 99 | 2 | 4D | 0 | 2 |
| 3410 | 2E | 53 | 20 | BF | 33 | 3A | 0 | E4 | 5 | FC | 33 | D6 | 0 | 1C | C0 | 3 |
| 3420 | 60 | 4 | B7 | 1 | 17 | 0 | 4 | 99 | 2 | E2 | 0 | 79 | 2 | B7 | 1 | 35 |
| 3430 | 7 | 17 | 0 | FE | 7 | 1 | F4 | CC | 0 | 9 | 15 | 8 | 6 | 65 | 6D | 70 |
| 3440 | 74 | 79 | 20 | 4D | 0 | 3 | 43 | 56 | 44 | F6 | 33 | 3A | 0 | C3 | 4 | B7 |
| 3450 | 1 | 46 | 2 | 56 | 2 | 9 | 3 | 67 | 2 | 9 | 3 | 17 | 0 | A | F8 | 2 |
| 3460 | 88 | 2 | 17 | 0 | A | F8 | 2 | 88 | 2 | 4D | 0 | 4 | 4C | 49 | 53 | E0 |
| 3470 | 32 | 3A | 0 | 4B | 34 | 65 | 10 | 4D | 0 | 6 | 43 | 41 | 52 | 45 | 34 | 3A |
| 3480 | 0 | FF | B | F6 | A | D6 | B | 58 | 3 | F8 | 83 | C7 | 2 | 57 | AD | 97 |
| 3490 | FF | 25 | 5 | 41 | 52 | 52 | D0 | 31 | 3A | 0 | FF | B | D8 | 2 | F6 | A |
| 34A0 | D6 | B | 58 | D1 | E0 | 3 | F8 | 83 | C7 | 2 | 57 | AD | 97 | FF | 25 | 7 |
| 34B0 | 43 | 4D | 41 | 79 | 34 | 3A | 0 | FF | B | 28 | 2 | 24 | B | F8 | 2 | F6 |
| 34C0 | A | D6 | B | E8 | DA | CB | 28 | 2 | B7 | 1 | A4 | 21 | 67 | 2 | 67 | 2 |
| 34D0 | F8 | 2 | 88 | 2 | 88 | 2 | C8 | 2 | 4D | 0 | 6 | 4D | 41 | 54 | F | 34 |
| 34E0 | 3A | 0 | FF | B | 28 | 2 | 24 | B | F8 | 2 | D8 | 2 | F6 | A | D6 | B |
| 34F0 | E8 | AD | CB | 28 | 2 | B7 | 1 | A4 | 21 | 67 | 2 | 67 | 2 | F8 | 2 | D8 |
| 3500 | 2 | 46 | 2 | D8 | 2 | 88 | 2 | 88 | 2 | C8 | 2 | 4D | 0 | 5 | 54 | 41 |
| 3510 | 42 | AF | 34 | 3A | 0 | FF | B | 8B | 3 | E2 | 0 | 24 | B | F1 | 0 | FB |
| 3520 | D6 | B | 58 | D1 | E0 | 3 | F8 | FF | 75 | 2 | AD | 97 | FF | 25 | 6 | 43 |
| 3530 | 54 | 41 | D | 35 | 3A | 0 | FF | B | 8B | 3 | E2 | 0 | 12 | B | F1 | 0 |
| 3540 | FB | D6 | B | 58 | 3 | F8 | 8A | 45 | 2 | 50 | AD | 97 | FF | 25 | 5 | 43 |
| 3550 | 4D | 45 | 2E | 35 | 3A | 0 | 35 | 4 | 88 | 2 | 67 | 2 | 8B | 3 | 8B | 3 |
| 3560 | A4 | 21 | E2 | 0 | 79 | 2 | E5 | 1 | 8B | 3 | CC | 21 | F1 | 0 | F5 | 67 |
| 3570 | 2 | CD | 22 | 4D | 0 | 5 | 53 | 46 | 49 | 4E | 35 | 7D | 35 | 58 | 59 | 5F |
| 3580 | 8C | C2 | 7 | F3 | AA | 8E | C2 | AD | 97 | FF | 25 | 5 | 53 | 44 | 55 | 75 |
| 3590 | 35 | 3A | 0 | 56 | 2 | 88 | 2 | 46 | 2 | E2 | 0 | E4 | 5 | 79 | 2 | 17 |
| 35A0 | 0 | 5 | 69 | 7 | 80 | 6 | 79 | 2 | 17 | 0 | 10 | 88 | 2 | E2 | 3 | 69 |
| 35B0 | 3 | 79 | 2 | E2 | 0 | 79 | 2 | 17 | 0 | 7 | 2E | 1 | 61 | 1 | D8 | 2 |
| 35C0 | 6C | 6 | 95 | 3 | 8F | 30 | 79 | 2 | 14 | 30 | 17 | 0 | 3 | 69 | 7 | F1 |
| 35D0 | 0 | E3 | 17 | 0 | 10 | 20 | 1 | C3 | 38 | 2 | E4 | 5 | 4D | 0 | 8 | 57 |
| 35E0 | 4F | 52 | 31 | 32 | 99 | 0 | 41 | 20 | 7 | 46 | 4F | 52 | 54 | 32 | 3A | 0 |
| 35F0 | 7F | 9 | E4 | 35 | C6 | 1 | 17 | 0 | 10 | A | 32 | E4 | 35 | B7 | 1 | 9E |
| 3600 | 5 | 6D | 32 | D6 | 0 | F5 | 17 | 0 | 10 | 1F | 32 | 4D | 0 | 4 | 41 | 4D |
| 3610 | 49 | 92 | 34 | 3A | 0 | F | 0 | FF | 7F | 67 | 2 | 67 | 2 | D8 | 2 | 56 |
| 3620 | 2 | 88 | 2 | 46 | 2 | E2 | 0 | 79 | 2 | B7 | 1 | 69 | 3 | 17 | 0 | 2 |
| 3630 | 7 | 1 | F4 | 4D | 0 | 4 | 41 | 4D | 41 | D | 36 | 3A | 0 | F | 0 | 0 |
| 3640 | 80 | 67 | 2 | 67 | 2 | D8 | 2 | 56 | 2 | 88 | 2 | 46 | 2 | E2 | 0 | 79 |
| 3650 | 2 | B7 | 1 | 7D | 3 | 17 | 0 | 2 | 7 | 1 | F4 | 4D | 0 | 6 | 42 | 49 |
| 3660 | 4E | 35 | 36 | 3A | 0 | 17 | 0 | 2 | C3 | 4 | C6 | 1 | 4D | 0 | A | 43 |
| 3670 | 4F | 4D | 8B | 35 | 76 | 36 | 58 | F7 | D8 | 48 | 50 | AD | 97 | FF | 25 | 7 |
| 3680 | 3F | 43 | 52 | 67 | 32 | 3A | 0 | CC | 4 | B7 | 1 | E0 | 8 | 61 | 3 | D6 |
| 3690 | 0 | 19 | E4 | 5 | 4 | 6 | 25 | 6 | AB | 5 | 15 | 8 | E | 20 | 69 | 73 |
| 36A0 | 6E | 27 | 74 | 20 | 75 | 6E | 69 | 71 | 75 | 65 | 20 | 38 | 2 | CC | 4 | C6 |
| 36B0 | 1 | 73 | 0 | 4D | 0 | 4 | 4C | 4F | 41 | 6B | 34 | 3A | 0 | 28 | 2 | 35 |
| 36C0 | 7 | 2 | E | 4D | 0 | 3 | 50 | 2F | 52 | 7F | 36 | 66 | 0 | 0 | 1 | 3 |
| 36D0 | 50 | 2F | 43 | C5 | 36 | 66 | 0 | 0 | 1 | 5 | 58 | 43 | 4D | DE | 35 | 66 |

```
36E0    0 20   0   5 23 50 4D 6E    36 66   0   1   0   6 50 45
36F0   4E CF 36 66   0 F8 F9   7    41 31 54 5D 36 66   0   0
3700    1  A 46 49 52 E8 35 66     0 11   0   9 4C 41 53 B5
3710   36 66   0 60   0   9 55 50    50   1 37 66   0 16 14  A
3720   4C 4F 57  B 37 66   0 F0    F8   2 4F 4E 20 ED 36 66
3730    0 FF FF   2 49 4E 20 82    26 66   0 FF FF   5 52 49
3740   47 F7 36 66   0 FF FF   3    4F 46 46 29 37 66   0   0
3750    0   3 4F 55 54 47 37 66     0   0   0   4 4C 45 46 1F
3760   37 66   0   0   0   5 23 4B    45 E3 36 66   0 80   0   8
3770   4B 45 59 5B 37 A2 34 22    56 6D 59 22 56 22 56 7B
3780   59 22 56 22 56 22 56 33    59 22 56 22 56 25 59 41
3790   59 B1 56 22 56 22 56 22    56 22 56 22 56 22 56 22
37A0   56 22 56 16 59 5E 59 22    56 22 56 50 59 22 56 22
37B0   56 22 56 22 56 22 56 A5    56 22 56 22 56 22 56 22
37C0   56 22 56 22 56 22 56 22    56 22 56 DB 57 22 56 C4
37D0   59 22 56 D3 59 C9 57 22    56 A7 59 DC 58 B6 59 EA
37E0   58 22 56 F8 58 8A 59   7    59 99 59 22 56 B7 57 E1
37F0   59 22 56 F0 59 22 56 22    56 73 57 22 56 5F 57 1A
```

LISTING NO. 2

Sheet 7

```
3800   5A 22 56 26 5A 22 56 22    56 FE 59 22 56 22 56 22
3810   56 22 56 22 56  C 5A 22    56 22 56 22 56 89 57 22
3820   56 22 56 22 56 22 56 22    56 22 56 22 56 22 56 22
3830   56 22 56 22 56 22 56 22    56 22 56 22 56 22 56 22
3840   56 22 56 22 56 22 56 22    56 22 56 22 56 22 56 22
3850   56 22 56 22 56 22 56 22    56 22 56 22 56 22 56 22
3860   56 22 56 22 56 22 56 22    56 22 56 22 56 22 56 22
3870   56 22 56 22 56 22 56  A    4B 45 59 6F 37 66   0   3
3880    0  A 43 59 43 65 37 A2    34 FD 37 F9 37 1D 38  B
3890   27 43 59 D9 36 99   0 41    42   7 56 52 41 15 37 66
38A0    0   0 20   7 4F 4C 41 51    37 66   0   0 30   7 43 52
38B0   41 81 38 66   0   0 60   7    46 52 41 99 38 66   0   0
38C0   70   7 43 54 52 AD 38 66     0   0 80   7 41 52 41 3D
38D0   37 66   0   0 90   7 53 52    41 C1 38 66   0   0   0   7
38E0   47 52 41 8F 38 66   0   0    10   8 45 50 52 B7 38 66
38F0    0   0 FF   2 56 30 20 E9    38 99   0 45 20   4 48 53
3900   43 DF 38 99   0 3C   0   3    53 45 47 D5 38 99   0   0
3910   20   4 56 41 44 F3 38 99     0 45 20   4 46 48 49 11
3920   39 99   0 45 20   5 58 59    50 FD 38 99   0 20 20   7
3930   58 59 50 25 39 99   0 20    20   6 4F 52 47 A3 38 99
3940    0 20 20   3 56 53 57 1B    39 99   0   0   0   2 56 52
3950   20 43 39 99   0 FF   0   2    48 53 20 2F 39 99   0   0
3960    0   2 56 53 20 4D 39 99     0   0   0   4 58 4D 49 57
3970   39 99   0 45 20   4 58 4D    41 6B 39 99   0 45 20   6
3980   58 52 41 75 39 99   0 20    20   4 59 4D 49 33 37 99
3990    0 45 20   4 59 4D 41 89    39 99   0 45 20   6 59 52
39A0   41 93 39 99   0 20 20   3    50 49 58 39 39 99   0 FF
39B0    0   4 58 4F 46 7F 39 99     0   0   0   4 59 4F 46 9D
39C0   39 99   0   0   0   5 46 52    41 61 39 99   0 11   0   5
39D0   43 59 43   7 39 99   0 20    20   6 54 41 52 CF 39 99
39E0    0 D0   0   5 54 42 41 D9    39 99   0 20   0   3 46 46
39F0   53 C5 39 99   0 45 20   7    46 46 53 ED 39 99   0   8
3A00    0   4 46 4F 4F F7 39 99     0 45 20   2 4C 43 20 77
3A10   38 99   0 40   0   2 52 43    20 CB 38 99   0 C0   0   5
3A20   57 49 44 B1 39 99   0 80     0   9 46 49 52   1 3A 99
3A30    0 14   0   8 4C 41 53  B    3A 99   0 B2   0   6 57 49
3A40   4E 1F 3A 99   0 20   0   5    53 4C 49 E3 39 99   0 20
```

```
3A50    0   3  57  53  51  3D  3A  99     0  45  20   3  57  47  54  51
3A60   3A  99   0  45  20   4  58  57    47  5B  3A  99   0   1   0   4
3A70   58  4E  2D  65  3A  99   0  45    20   2  58  4E  20  6F  3A  99
3A80    0  45  20   4  59  57  47  BB    39  99   0   1   0   4  59  4E
3A90   2D  83  3A  99   0  45  20   2    59  4E  20  8D  3A  99   0  45
3AA0   20   5  58  4C  45  79  3A  99     0  20  20   6  58  52  49  A1
3AB0   3A  99   0  20  20   5  49  50    45  97  3A  99   0  20  20   5
3AC0   56  50  45  29  3A  99   0  20    20   4  58  53  55  AB  3A  99
3AD0    0  45  20   4  59  53  55  B5    3A  99   0  45  20   6  58  53
3AE0   51  C9  3A  99   0  20  20   5    41   6  59  53  51  D3  3A  99
3AF0    0  20  20   5  41   5  58  59    53  DD  3A  99   0  20  20   5
3B00   41   6  52  53  43  15  3A  99     0  E8   3   6  46  57  49  BF
3B10   3A  99   0  11   0   9  45  56    45   B  3B  99   0  54  48   6
3B20   57  47  54  F5  3A  99   0  20    20   3  58  50  46  1F  3B  99
3B30    0  10   0   5  53  4C  2D  47    3A  99   0  20  20   2  50  23
3B40   20  A7  39  99   0  45  20   3    49  50  49  E9  3A  99   0  18
3B50    0   5  54  48  45  33  3B  99     0  23   0   3  50  48  49  3D
3B60   3B  99   0  2D   0   6  53  54    48  51  3B  99   0  20  20   6
3B70   43  54  48  65  3B  99   0  20    20   4  53  50  48  6F  3B  99
3B80    0  45  20   4  43  50  48  79    3B  99   0  45  20   4  53  50
3B90   53  83  3B  99   0  45  20   5    43  50  53  8D  3B  99   0  20
3BA0   20   2  58  43  20  29  3B  99     0  45  20   2  59  43  20  47
3BB0   3B  99   0  45  20   4  41  5B    4D   1  3B  99   0  45  20   4
3BC0   41  5B  4E  B5  3B  99   0  45    20   7  23  43  4F  97  3B  99
3BD0    0   8   0   A  43  4F  4C  C9    3B  99   0  42  4C   7  49  58
3BE0   43  AB  3B  99   0  20  20   3    52  45  44  BF  3B  99   0  FF
3BF0    0   5  47  52  45  A1  3B  99     0  FF   0   4  42  4C  55  E7

3C00   3B  99   0  FF   0   5  4C  4F    4C  33  3A  99   0   1   0   5
3C10   55  50  4C  15  3B  99   0  FF     0   6  50  52  41  5B  3B  99
3C20    0  20  20   4  4C  42  55   5    3C  87  34  20  20  20  20  32
3C30   30  20  4D  41  59  20  38  32    20  20  20  20   0   0   0   0
3C40    0  33  31  31   0   0   0   0     0   0   0   0   0   0   0   0
3C50    0   0   0   0   0   0   0   0     0   0   0   0   0   0   0   0
3C60    0   0   0   0   0   0   0   0     0   0   4  4B  45  59  5A  3A
3C70    4  4B  45  59  60   4  4B  45    59  65  3A  21  32  20   0   0
3C80    0   0   0   0   0   0   0  33    43  36  41   0   0  33  43  37
3C90   30   0  33  43  37  35   0   0     0   0   0   0   0   0   0   0
3CA0    0   0   0   0   0   0   0   0     0   0   0   0   0   0   0   0
3CB0    0   0   0   0   0   0   0   0     0   0   0   0   0   0   0   0
3CC0    0   0   0   0   0   0   0   0     0   0   0   0   0   0   0   0
3CD0    0   0   0   0   0   0   0   0     0   0   0   0   0   0   0   0
3CE0    7  58  43  4F  8C  38  3D  31    20  20  20   0   0   0   0   0
3CF0    0   0   0   0   0   0   0   0     0   0   0   0   0   0   0   0
3D00    0   0   0   0   0   0   0   0     0   0   0   0   0   0   0   0
3D10    0   0   0   0   7  58  43  4F    C0  38  B6  31   7  58  43  4F
3D20   C8  38  BE  31  20  20  20   0     5  46  57   8  4C  50  52  23
3D30   3C  87  34  45  20  20  20   0     0  33  44  31  43   0   0   0
3D40    0   0   0   0   0   0   0   0     0   0   0   0   0   0   0   0
3D50    0   0   5  41  54  45  96  38    3D  31  20   0   5  46  57  47
3D60   DE  38  B6  31   5  46  57  47    E6  38  BE  31  20   0   0   0
3D70    0   0   0   0   7  58  43  4F    20  39   7  58  43  4F  26   7
3D80   58  43  4F  2B  39  21  32  20    20  20  CA  38  B6  31   5  41
3D90   54  45  D2  38  BE  31  20  33    44  37  41   0  33  44  37  46
3DA0    0   0   0  33  44  38  36   0     0   0   0  33  44  38  45   0
3DB0    0   0   0   0   0   0   0   0     0   0   0   0   5  46  57  47
3DC0   3E  39   5  46  57  47  44   5    46  57  47  49  39  21  32  20
3DD0    0   0   0   0   0   0   0   0     0  33  44  42  43   0   0  33
```

| | 43 | | | | | | | | 44 | | | | | | |
|---|---|---|---|---|---|---|---|---|---|---|---|---|---|---|---|
| 3DE0 | 44 | 43 | 32 | 0 | 33 | 44 | 43 | 37 | 54 | 45 | 2A | 39 | 5 | 41 | 54 | 45 |
| 3DF0 | 30 | 5 | 41 | 54 | 45 | 35 | 39 | 21 | 32 | 20 | 0 | 0 | 0 | 0 | 0 | 0 |
| 3E00 | 0 | 0 | 0 | 33 | 44 | 45 | 36 | 0 | 0 | 33 | 44 | 45 | 43 | 0 | 33 | 44 |
| 3E10 | 46 | 31 | 0 | 0 | 0 | 0 | 0 | 0 | 0 | 0 | 0 | 0 | 0 | 0 | 0 | 0 |
| 3E20 | 0 | 0 | 0 | 0 | 0 | 0 | 0 | 0 | 0 | 0 | 0 | 0 | 0 | 0 | 0 | 0 |
| 3E30 | 0 | 0 | 0 | 6 | 43 | 41 | 4C | D3 | 3B | 87 | 34 | 20 | 20 | 0 | 0 | 0 |
| 3E40 | 0 | 0 | 0 | 0 | 0 | 0 | 0 | 0 | 0 | 0 | 0 | 0 | 0 | 0 | 0 | 0 |
| 3E50 | 0 | 0 | 0 | 0 | 0 | 0 | 0 | 0 | 0 | 0 | 0 | 0 | 0 | 0 | 0 | 0 |
| 3E60 | 0 | 0 | 0 | 0 | 0 | 0 | 0 | 0 | 0 | 0 | 0 | 0 | 0 | 0 | 0 | 0 |
| 3E70 | 0 | 0 | 0 | 0 | 0 | 0 | 0 | 0 | 0 | 0 | 0 | 0 | 0 | 0 | 0 | 0 |
| 3E80 | 0 | 0 | 0 | 0 | 0 | 0 | 0 | 0 | 0 | 0 | 0 | 0 | 0 | 0 | 0 | 0 |
| 3E90 | 0 | 0 | 0 | 0 | 0 | 0 | 0 | 0 | 0 | 0 | 0 | 0 | 0 | 0 | 0 | 0 |
| 3EA0 | 0 | 0 | 0 | 0 | 0 | 0 | 0 | 0 | 0 | 0 | 0 | 0 | 0 | 0 | 0 | 0 |
| 3EB0 | 0 | 0 | 0 | 0 | 0 | 0 | 0 | 0 | 0 | 0 | 0 | 0 | 0 | 0 | 0 | 0 |
| 3EC0 | 0 | 0 | 0 | 0 | 0 | 0 | 0 | 0 | 0 | 0 | 0 | 0 | 0 | 0 | 0 | 0 |
| 3ED0 | 0 | 0 | 0 | 0 | 0 | 0 | 0 | 0 | 0 | 0 | 0 | 0 | 0 | 0 | 0 | 0 |
| 3EE0 | 0 | 0 | 0 | 0 | 0 | 0 | 0 | 0 | 0 | 0 | 0 | 0 | 0 | 0 | 0 | 0 |
| 3EF0 | 0 | 0 | 0 | 0 | 0 | 0 | 0 | 0 | 0 | 0 | 0 | 0 | 0 | 0 | 0 | 0 |
| 3F00 | 0 | 0 | 0 | 0 | 0 | 0 | 0 | 0 | 0 | 0 | 0 | 0 | 0 | 0 | 0 | 0 |
| 3F10 | 0 | 0 | 0 | 0 | 0 | 0 | 0 | 0 | 0 | 0 | 0 | 0 | 0 | 0 | 0 | 0 |
| 3F20 | 0 | 0 | 0 | 0 | 0 | 0 | 0 | 0 | 0 | 0 | 0 | 0 | 0 | 0 | 0 | 0 |
| 3F30 | 0 | 0 | 0 | 0 | 0 | 0 | 0 | 0 | 0 | 0 | 0 | 4 | 4B | 45 | 59 | 2B |
| 3F40 | 3D | A2 | 34 | 20 | 0 | 0 | 0 | 0 | 0 | 0 | 0 | 0 | 0 | 0 | 0 | 0 |
| 3F50 | 0 | 0 | 0 | 0 | 0 | 0 | 0 | 0 | 0 | 0 | 7 | 50 | 52 | 4F | B4 | 38 |
| 3F60 | 8B | 31 | 0 | 1 | 20 | 0 | 0 | 0 | 0 | 0 | 0 | 0 | 0 | 0 | 0 | 0 |
| 3F70 | 0 | 0 | 0 | 0 | 0 | 0 | 0 | 0 | 0 | 0 | 0 | 0 | 0 | 0 | 0 | 0 |
| 3F80 | 0 | 0 | 0 | 0 | 0 | 0 | 0 | 0 | 0 | 0 | 0 | 0 | 0 | 0 | 4 | 54 |
| 3F90 | 42 | 4C | 2 | 3B | 66 | 0 | 7 | 50 | 52 | 4F | F0 | 38 | C | 32 | 0 | 1 |
| 3FA0 | 20 | 0 | D6 | B | E8 | F9 | C0 | A0 | 35 | 46 | 2 | B7 | 1 | 4D | 0 | 7 |
| 3FB0 | 52 | 45 | 51 | 33 | 46 | 39 | 36 | 40 | 0 | 8 | 27 | 52 | 45 | 14 | 3D | A4 |
| 3FC0 | 3F | 40 | 0 | 8 | 27 | 43 | 4F | B9 | 3F | A4 | 3F | 42 | 0 | 6 | 27 | 54 |
| 3FD0 | 52 | C3 | 3F | A4 | 3F | 43 | 0 | 5 | 27 | 50 | 4F | CD | 3F | A4 | 3F | 44 |
| 3FE0 | 0 | 5 | 27 | 44 | 41 | D7 | 3F | A4 | 3F | 46 | 0 | 4 | 27 | 41 | 4 | 54 |
| 3FF0 | 42 | 4C | 62 | 3B | 7 | 50 | 52 | 4F | 4E | 7 | 50 | 52 | 4F | 53 | 39 | 6F |

LISTING NO. 2

Sheet 9

| | | | | | | | | | | | | | | | | |
|---|---|---|---|---|---|---|---|---|---|---|---|---|---|---|---|---|
| 4000 | 32 | 0 | 1 | 20 | E8 | 99 | C0 | 0 | 36 | 46 | 2 | B7 | 1 | 4D | 0 | 7 |
| 4010 | 52 | 33 | 46 | 46 | 34 | 66 | 33 | 46 | 46 | 39 | 27 | 52 | 45 | 74 | 3D | 4 |
| 4020 | 40 | 40 | 0 | 8 | 27 | 43 | 4F | 19 | 40 | 4 | 40 | 42 | 0 | 6 | 27 | 54 |
| 4030 | 52 | 23 | 40 | 4 | 40 | 43 | 0 | 5 | 27 | 50 | 4F | 2D | 40 | 4 | 40 | 44 |
| 4040 | 0 | 5 | 27 | 44 | 41 | 7 | 58 | 43 | 4F | F1 | 3B | A2 | 34 | 20 | 20 | 20 |
| 4050 | 40 | 4 | 40 | 48 | 0 | 4 | 27 | 53 | 45 | 4B | 40 | 4 | 40 | 4A | 0 | 6 |
| 4060 | 27 | 48 | 42 | 55 | 40 | 4 | 40 | 4C | 0 | 6 | 27 | 56 | 42 | 5F | 40 | 4 |
| 4070 | 40 | 4D | 0 | 4 | 27 | 45 | 59 | 69 | 40 | 4 | 40 | 4E | 0 | 3 | 27 | 4F |
| 4080 | 45 | 73 | 40 | 4 | 40 | 4F | 0 | 6 | 27 | 41 | 56 | 7D | 40 | 5 | 46 | 57 |
| 4090 | 47 | F | 3C | A2 | 34 | 20 | 40 | 4 | 40 | 54 | 0 | 6 | 27 | 4C | 4F | 91 |
| 40A0 | 40 | 4 | 40 | 55 | 0 | 4 | 27 | 5A | 45 | 9B | 40 | 4 | 40 | 56 | 0 | 7 |
| 40B0 | 27 | 48 | 4D | A5 | 40 | 4 | 40 | 5 | 41 | 54 | 45 | FB | 3B | A2 | 34 | 20 |
| 40C0 | 40 | 58 | 0 | 4 | 27 | 41 | 4D | B9 | 40 | 4 | 40 | 59 | 0 | 5 | 27 | 48 |
| 40D0 | 4D | C3 | 40 | 4 | 40 | 5A | 0 | 6 | 27 | 55 | 50 | CD | 40 | 4 | 40 | 5D |
| 40E0 | 0 | B | 27 | 43 | 4F | D7 | 40 | 4 | 40 | 5E | 0 | C | 27 | 42 | 49 | E1 |
| 40F0 | 40 | 4 | 40 | 5F | 0 | 5 | 45 | 58 | 56 | BC | 3D | 99 | 0 | 4A | 4B | 34 |
| 4100 | 4B | 6A | 4D | 78 | 4D | 92 | 4D | AC | 4D | 5 | 23 | 41 | 4F | EE | 3F | 66 |
| 4110 | 0 | 0 | 0 | 4 | 23 | 41 | 49 | 9 | 41 | 66 | 0 | 1 | 0 | 8 | 23 | 41 |
| 4120 | 55 | 13 | 41 | 66 | 0 | 2 | 0 | 4 | 23 | 41 | 43 | 1D | 41 | 66 | 0 | 3 |
| 4130 | 0 | 9 | 23 | 45 | 59 | 27 | 41 | 66 | 0 | 4 | 0 | A | 23 | 45 | 59 | 31 |

```
4140   41 66  0  5  0  4 3F 54        49 48 39 3A  0 17  0  2
4150   93 2F B8 2F  F  0 C2  0        B6 24 17  0  2 2E  1 61
4160    1 61  3 4D  8 54 50 52        CE 3A 8B 31  0  1 20 20
4170   93 2F 5A 36 B7  1 64 36        B7  1 77  1 D6  0  5 8B
4180    3 CC  0  A 95  3 5A 36        B7  1 64 36 C6  1 4D  0
4190    6 56 49 44 F5 40 3A  0        F6 35 46  2 B8 2F B7 2D
41A0    8 54 50 52  A 3B  C 32         0  1 20 20 B7  1 95  3
41B0   96 41 4D  0  4 56 52 45        90 41 3A  0 28 34 31 41
41C0   30  1 17  0  2 96 41 4D         0  4 53 4E 41 3B 41 3A
41D0    0 8B  3 17  0  3 96 41        4D  0  7 48 53 43 EB 40
41E0   3A  0 28  2 8C 36 C6  1        17  0  4 96 41 4D  0  7
41F0   56 53 43 B4 41 3A  0 28         2 96 36 C6  1 17  8 54
4200   50 52 68  8 54 50 52 6D        3B 6F 32  0  1 20 20  0
4210    6 96 41 4D  0  6 56 42        4C EF 41 34 31 46 45  0
4220   34 32 30 33 36 4A 2F A8        41 4D  0  4 41 56 49  F
4230   40 3A  0 17  0  1 17  0         3 78 36 4A 2F A8 41 4D
4240    0  5 44 41 56 C9 41 3A         0 17  0  2 17  0  3 78
4250   36 4A 2F A8 41 4D  0  4        56 52 41 15 42 3A  0 17
4260    0  3 17  0  3 78 36 4A        2F A8 41 4D  0  4 21 56
4270   53 2B 42 3A  0 28  2 67         2 2E  1 46  2 78 36 4A
4280   2F A8 41 4D  0  4 4C 49        56 6A 3C 3A  0 17  0  4
4290   73 42 A8 41 4D  0  3 52        45 47 6D 42 3A  0 17  0
42A0    8 73 42 A8 41 4D  0  6        42 38 43 96 42 3A  0 17
42B0    0 10 73 42 A8 41 4D  0         6 42 39 43 A7 42 3A  7
42C0   50 52 4F 19 3C F0 34  0         1 20 43 52 41 41 42 3A
42D0    0 28  2 17  0  2 6D 22        3F  3 AD 42 17  0  4 6D
42E0   22 E8  2 3F  3 BE 42 4D         0  7 52 45 41 B8 42 3A
42F0    0 17  0 40 73 42 A8 41        4D  0  7 43 4F 4C C9 42
4300   3A  0  F  0 80  0 73 42        A8 41 4D  0  8 3F 4C 45
4310   65 41 3A  0 79 40 88 2D        61  1 4D  0 9C 50 51 1E
4320   E4 C2  D  2  0 E6 C2 B9         0 80 8E D9 2B C0 A0  6
4330    0 8A E0 A0  7  0 1F  3         6 24 34 89  6 5C 36 59
4340   58 9D CF CF  4 54 52 2F        FA 42 3A  0  6  2 17  0
4350    0 17  0 20 67  2 17  0        20 F8  2 28  2 96 2A 56
4360    2  F  0 80  9 A9  1 D6         0  6 17  0 20 CC  4 54
4370   42 4C 64 41 66  0  0  0         9 41 43 4F 52 3D 3A  0
4380   5E  0 D6  B E8 19 BD 6C        35 46  2 B7  1 4D  0  7
4390   52 45 51 78 43 66  0 40         0  8 27 52 45 E0 3C 84
43A0   43 40  0  8 27 43 4F 99        43 84  4 54 42 4C A0 41
43B0   66  0  0  0  9 41 43 4F        8E 3D 3A  0 5E  0 D6  B
43C0   E8 DD BC A8 35 46  2 B7         1 4D  0  7 52 45 51 B4
43D0   43 66  0 40  0  8 27 52        45 1C 3D C0 43 40  0  8
43E0   27 43 4F D5 43 C0 43 42         0  6 27 54 52 DF 43 C0
43F0   43 43  0  5 27 50 4F E9        43 C0 43 44  0  5 27 44
```

LISTING NO.
Sheet 10

```
4400   41 F3 43 C0 43 46  0  4         4 54 42 4C FE  4 54 42
4410   4C  3 42 66  0  0  0  9        41 43 4F F1 3D 3A  0 5E
4420    0 D6  B E8 7A BC  B 36        46  2 B7  1 4D  0  7 52
4430   45 51 17 44 66  0 40  0         8 27 52 45 7F 3D 23 44
4440   40  0  8 27 43 4F 38 44        23 44 42  0  6 27 54 52
4450   42 44 23 44 43  0  5 27        50 4F 4C 44 23 44 44  0
4460    5 27 44 41 56 44 23 44        46  0  4 27 41 44 60 44
4470   23 44 48  0  4 27 53 45        6A 44 23 44 4A  0  6 27
4480   48 42 74 44 23 44 4C  0         6 27 56 42 7E 44 23 44
```

| | | | | | | | | | | | | | | |
|---|---|---|---|---|---|---|---|---|---|---|---|---|---|---|
| 4490 | 4D | 0 | 4 | 27 | 45 | 59 | 88 | 44 | 23 | 44 | 4E | 0 | 3 | 27 | 4F | 45 |
| 44A0 | 92 | 44 | 23 | 44 | 4F | 0 | 6 | 27 | 41 | 56 | 9C | 44 | 23 | 44 | 52 | 0 |
| 44B0 | 6 | 27 | 57 | 48 | A6 | 44 | 23 | 44 | 54 | 0 | 6 | 27 | 4C | 4F | B0 | 44 |
| 44C0 | 23 | 44 | 55 | 0 | 4 | 27 | 5A | 45 | BA | 8 | 54 | 50 | 52 | 33 | 3E | F0 |
| 44D0 | 34 | 0 | 1 | 20 | 20 | 44 | 57 | 0 | 5 | 27 | 56 | 45 | CE | 44 | 23 | 44 |
| 44E0 | 58 | 0 | 4 | 27 | 41 | 4D | D8 | 44 | 23 | 44 | 59 | 0 | 5 | 27 | 48 | 4D |
| 44F0 | E2 | 44 | 23 | 44 | 5A | 0 | 6 | 27 | 55 | 50 | EC | 44 | 23 | 44 | 5D | 0 |
| 4500 | B | 27 | 43 | 4F | F6 | 44 | 23 | 44 | 5E | 0 | C | 27 | 42 | 49 | 0 | 45 |
| 4510 | 23 | 44 | 5F | 0 | 5 | 45 | 58 | 56 | C7 | 3D | 99 | 0 | 69 | 4F | 53 | 4F |
| 4520 | 89 | 51 | 97 | 51 | B1 | 51 | CB | 51 | 5 | 23 | 41 | 4F | D | 44 | 66 | 0 |
| 4530 | 0 | 0 | 4 | 23 | 41 | 49 | 28 | 45 | 66 | 0 | 1 | 0 | 8 | 23 | 41 | 55 |
| 4540 | 32 | 45 | 66 | 0 | 2 | 0 | 4 | 23 | 41 | 43 | 3C | 45 | 66 | 0 | 3 | 0 |
| 4550 | 9 | 23 | 45 | 59 | 46 | 45 | 66 | 0 | 4 | 0 | A | 23 | 45 | 59 | 50 | 45 |
| 4560 | 66 | 0 | 5 | 0 | 4 | 3F | 54 | 49 | F9 | 3F | 3A | 0 | 17 | 0 | 2 | 9E |
| 4570 | 2F | C3 | 2F | F | 0 | C2 | 0 | B6 | 24 | 17 | 0 | 2 | 2E | 1 | 61 | 1 |
| 4580 | 61 | 3 | 4D | 0 | 4 | 3F | 48 | 49 | 64 | 45 | 3A | 0 | 17 | 0 | 2 | 9E |
| 4590 | 2F | 65 | 36 | B7 | 1 | 6F | 36 | B7 | 1 | 77 | 1 | D6 | 0 | 5 | 8B | 3 |
| 45A0 | CC | 0 | A | 95 | 3 | 65 | 36 | B7 | 1 | 6F | 36 | C6 | 1 | 4D | 0 | 6 |
| 45B0 | 56 | 49 | 44 | 14 | 45 | 3A | 0 | 1 | 36 | 46 | 2 | C3 | 2F | C2 | 2D | 4D |
| 45C0 | 0 | 4 | 4D | 4F | 44 | 59 | 32 | 3A | 0 | 83 | 36 | B7 | 1 | 95 | 3 | B5 |
| 45D0 | 45 | 4D | 0 | 4 | 56 | 52 | 45 | AF | 45 | 3A | 0 | 28 | 2 | 8D | 36 | C6 |
| 45E0 | 1 | 17 | 0 | 2 | B5 | 45 | 4D | 0 | 4 | 53 | 4E | 41 | 5A | 45 | 3A | 0 |
| 45F0 | 8B | 3 | 17 | 0 | 3 | B5 | 45 | 4D | 0 | 7 | 48 | 53 | 43 | A | 45 | 3A |
| 4600 | 0 | 28 | 2 | 97 | 36 | C6 | 1 | 17 | 0 | 4 | B5 | 45 | 4D | 0 | 7 | 56 |
| 4610 | 53 | 43 | D3 | 45 | 3A | 0 | 28 | 2 | A1 | 36 | C6 | 1 | 17 | 0 | 5 | B5 |
| 4620 | 45 | 4D | 0 | 4 | 57 | 49 | 50 | F9 | 45 | 3A | 0 | 8B | 3 | 17 | 0 | 6 |
| 4630 | B5 | 45 | 4D | 0 | 6 | 56 | 42 | 4C | E | 46 | 3A | 0 | 17 | 0 | 0 | 17 |
| 4640 | 0 | 3 | 83 | 36 | 55 | 2F | C7 | 45 | 4D | 0 | 4 | 41 | 56 | 49 | 2E | 44 |
| 4650 | 3A | 0 | 17 | 0 | 1 | 17 | 0 | 3 | 83 | 36 | 55 | 2F | C7 | 45 | 4D | 0 |
| 4660 | 5 | 44 | 41 | 56 | E8 | 45 | 3A | 0 | 17 | 0 | 2 | 17 | 0 | 3 | 83 | 36 |
| 4670 | 55 | 2F | C7 | 45 | 4D | 0 | 4 | 56 | 52 | 41 | 34 | 46 | 3A | 0 | 17 | 0 |
| 4680 | 3 | 17 | 0 | 3 | 83 | 36 | 55 | 2F | C7 | 45 | 4D | 0 | 4 | 21 | 56 | 53 |
| 4690 | 4A | 46 | 3A | 0 | 28 | 2 | 67 | 2 | 2E | 1 | 46 | 2 | 83 | 36 | 55 | 2F |
| 46A0 | C7 | 45 | 4D | 0 | 4 | 4C | 49 | 56 | 75 | 3C | 3A | 0 | 17 | 0 | 4 | 92 |
| 46B0 | 46 | C7 | 45 | 4D | 0 | 3 | 52 | 45 | 47 | 8C | 46 | 3A | 0 | 17 | 0 | 8 |
| 46C0 | 92 | 46 | C7 | 45 | 4D | 0 | 6 | 42 | 38 | 43 | B5 | 46 | 3A | 0 | 17 | 0 |
| 46D0 | 10 | 92 | 46 | 4 | 54 | 42 | 4C | C9 | 44 | 66 | 0 | 0 | 0 | 9 | 41 | 43 |
| 46E0 | 4F | B7 | 40 | 3A | 0 | 5E | 0 | D6 | B | E8 | B4 | B9 | D1 | 38 | 46 | 2 |
| 46F0 | B7 | 1 | 4D | 0 | 7 | 52 | 45 | 51 | DD | 46 | 66 | 0 | 40 | 0 | 8 | 27 |
| 4700 | 52 | 45 | 45 | 40 | E9 | 46 | 40 | 0 | 8 | 27 | 43 | 4F | FE | 46 | E9 | 46 |
| 4710 | 42 | 0 | 6 | 27 | 54 | 52 | 8 | 47 | E9 | 46 | 43 | 0 | 5 | 27 | 50 | 4F |
| 4720 | 12 | 47 | E9 | 46 | 44 | 0 | 5 | 27 | 44 | 41 | 1C | 47 | E9 | 46 | 46 | 0 |
| 4730 | 4 | 27 | 41 | 44 | 26 | 47 | E9 | 46 | 48 | 0 | 4 | 27 | 53 | 45 | 30 | 47 |
| 4740 | E9 | 46 | 4A | 0 | 6 | 27 | 48 | 42 | 3A | 47 | E9 | 46 | 4C | 0 | 6 | 27 |
| 4750 | 56 | 42 | 44 | 47 | E9 | 46 | 4D | 0 | 4 | 27 | 45 | 59 | 4E | 47 | E9 | 46 |
| 4760 | 4E | 0 | 3 | 27 | 4F | 45 | 58 | 47 | E9 | 46 | 4F | 0 | 6 | 27 | 41 | 56 |
| 4770 | 62 | 47 | E9 | 46 | 52 | 0 | 6 | 27 | 57 | 48 | 6C | 47 | E9 | 46 | 54 | 0 |
| 4780 | 6 | 27 | 4C | 4F | 76 | 47 | E9 | 46 | 55 | 0 | 4 | 27 | 5A | 45 | 80 | 47 |
| 4790 | E9 | 46 | 56 | 0 | 7 | 27 | 48 | 4D | 8A | 47 | E9 | 46 | 57 | 0 | 5 | 27 |
| 47A0 | 56 | 45 | 94 | 47 | E9 | 46 | 58 | 0 | 4 | 27 | 41 | 4D | 9E | 47 | E9 | 46 |
| 47B0 | 59 | 0 | 5 | 27 | 48 | 4D | A8 | 47 | E9 | 46 | 5A | 0 | 6 | 27 | 55 | 50 |
| 47C0 | B2 | 47 | E9 | 46 | 5D | 0 | B | 27 | 43 | 4F | BC | 47 | E9 | 46 | 5E | 0 |
| 47D0 | C | 27 | 42 | 49 | C6 | 47 | E9 | 46 | 5F | 0 | 5 | 45 | 58 | 56 | 8D | 40 |
| 47E0 | 99 | 0 | 2F | 52 | 19 | 52 | 4F | 54 | 5D | 54 | 77 | 54 | 91 | 54 | 5 | 23 |
| 47F0 | 41 | 4F | D3 | 46 | 66 | 0 | 0 | 0 | 4 | 23 | 41 | 49 | EE | 47 | 66 | 0 |

LISTING NO. 2

Sheet 11

```
4800    1    0    8   23   41   55   F8   47   66    0    2    0    4   23   41   43
4810    2   48   66    0    3    0    9   23   45   59    C   48   66    0    4    0
4820    A   23   45   59   16   48   66    0    5    0    4   3F   54   49   BF   42
4830   3A    0   17    0    2   1F   32   44   32    F    0   C2    0   B6   24   17
4840    0    2   2E    1   61    1   61    3   4D    0    4   3F   48   49   2A   48
4850   3A    0   17    0    2   1F   32   2B   39   B7    1   35   39   B7    1   77
4860    1   D6    0    5   8B    3   CC    0    A   95    3   2B   39   B7    1   35
4870   39   C6    1   4D    0    6   56   49   44   DA   47   3A    0   C7   38   46
4880    2   44   32   43   30   4D    0    4   4D   4F   44   DA   34   3A    0   49
4890   39   B7    1   95    3   7B   48   4D    0    4   56   52   45   75   48   3A
48A0    0   28    2   53   39   C6    1   17    0    2   7B   48   4D    0    4   53
48B0   4E   41   20   48   3A    0   8B    3   17    0    3   7B   48   4D    0    7
48C0   48   53   43   D0   47   3A    0   28    2   5D   39   C6    1   17    0    4
48D0   7B   48   4D    0    7   56   53   43   99   48   3A    0   28    2   67   39
48E0   C6    1   17    0    5   7B   48   4D    0    4   57   49   50   BF   48   3A
48F0    0   8B    3   17    0    6   7B   48   4D    0    6   56   42   4C   D4   48
4900   3A    0   17    0    0   17    0    3   49   39   D6   31   8D   48   4D    0
4910    4   41   56   49   F4   46   3A    0   17    0    1   17    0    3   49   39
4920   D6   31   8D   48   4D    0    5   44   41   56   AE   48   3A    0   17    0
4930    2   17    0    3   49   39   D6   31   8D   48   4D    0    4   56   52   41
4940   FA   48   3A    0   17    0    3   17    0    3   49   39   D6   31   8D   48
4950   4D    0    4   21   56   53   10   49   3A    0   28    2   67    2   2E    1
4960   46    2   49   39   D6   31   8D   48   4D    0    4   4C   49   56   3B   3F
4970   3A    0   17    0    4   58   49   8D   48   4D    0    3   52   45   47   52
4980   49   3A    0   17    0    8   58   49   8D   48   4D    0    6   42   38   43
4990   7B   49   3A    0   17    0   10   58   49   8D   48   4D    0    6   42   39
49A0   43   8C   49   3A    0   17    0   20   58   49   8D   48   4D    0    9   43
49B0   52   41   26   49   3A    0   28    2   17    0    2   6D   22   3F    3   92
49C0   49   17    0    4   6D   22   E8    2   3F    3   A3   49   4D    0    7   52
49D0   45   41   9D   49   3A    0   17    0   40   58   49   8D   48   4D    0    7
49E0   43   4F   4C   AE   49   3A    0    F    0   80    0   58   49   8D   48   4D
49F0    0    8   3F   4C   45   4A   48   3A    0   5E   47   14   30   61    1   4D
4A00    0   9C   50   51   1E   E4   C2    D    2    0   E6   C2   B9    0   80   8E
4A10   D9   2B   C0   A0    6    0   8A   E0   A0    7    0   1F    3    6   F5   36
4A20   89    6   2D   39   59   58   9D   CF   CF    4   54   52   2F   DF   49   3A
4A30    0    6    2   17    0    0   17    0   20   67    2   17    0   20   F8    2
4A40   28    2   22   2D   56    2    F    0   80    9   A9    1   D6    0    6   17
4A50    0   20   CC    0    2   8B    3   7E   2D   B7    1   3F    1   3D    5    D
4A60   19   17    2   F2   2D   11   2F   3D    5   19   19   4D    0    5   54   52
4A70   41   29   4A   3A    0    4    6   67    2   67    2   2F   4A   38    2   4D
4A80    0    3   49   46   44   DD   3B   3A    0   8B    3   C5   48   8B    3   DA
4A90   48   8B    3   17   39   C6    1   4D    0    7   46   3E   54   3C   49   3A
4AA0    0   7E   2D   B7    1   D6    0    E   B9    2   17    0    8   F8    2   FD
4AB0   36   88    2   CC    0   22   28    2   17    0    9   A9    1   D6    0   11
4AC0   17    0    A   99    2   17    0    8   F8    2   FD   36   88    2   CC    0
4AD0    7   B9    2   17    0    8   F8    2   4D    0    3   46   3C   44   99   4A
4AE0   3A    0   74   2D   B7    1   46    2   9F   38    F    0    0   10   A9   22
4AF0   74   2D   C6    1   9F   4A   8B    3   17    0    8   8B    3   E2    0   56
4B00    2   17    0    8   2F   4A    F    0    0   20   88    2   46    2   AA    2
4B10   46    2   3D    5   2E   19   F1    0   E6   48    4   74   2D   C6    1   4D
4B20    0    3   46   3E   44   DA   4A   3A    0   74   2D   B7    1   46    2   9F
4B30   38    F    0    0   10   A9   22   74   2D   C6    1   9F   4A   8B    3   17
4B40    0    8   8B    3   E2    0   56    2   17    0    A   2F   4A    F    0    0
4B50   20   88    2   46    2   AA    2   46    2   3D    5   2E   19   F1    0   E6
4B60   48    4   74   2D   C6    1   4D    0    8   46   52   4F   21   4B   3A    0
```

| | | | | | | | | | | | | | |
|---|---|---|---|---|---|---|---|---|---|---|---|---|---|
| 4B70 | E0 | 4A | 4D | 0 | 6 | 54 | 4F | 44 | 6D | 4A | 3A | 0 | 27 | 4B | 4D | 0 |
| 4B80 | 4 | 48 | 46 | 3C | E9 | 48 | 3A | 0 | 87 | 4A | 9F | 4A | 17 | 0 | 8 | F8 |
| 4B90 | 2 | 46 | 2 | 61 | 3 | 61 | 3 | F | 0 | 80 | 0 | F8 | 2 | 17 | 39 | D5 |
| 4BA0 | 1 | 28 | 2 | 17 | 0 | 40 | 88 | 2 | 46 | 2 | E2 | 0 | F | 0 | 0 | 4 |
| 4BB0 | 8B | 3 | E2 | 0 | 8A | 18 | F1 | 3 | 9E | A | 79 | 2 | 88 | 2 | F | 0 |
| 4BC0 | 80 | 0 | 88 | 2 | 9F | 38 | 17 | 39 | B7 | 1 | F | 0 | 80 | 0 | 6E | 30 |
| 4BD0 | F | 0 | 0 | 1 | 17 | 39 | D5 | 1 | F | 0 | 0 | 1 | 7 | 1 | 05 | F1 |
| 4BE0 | 0 | CA | 4D | 0 | 3 | 49 | 4E | 5A | 81 | 4A | 3A | 0 | 28 | 2 | 61 | 1 |
| 4BF0 | D6 | 0 | 2 | AA | 2 | 4D | 0 | 3 | 44 | 43 | 5A | 74 | 4B | 3A | 0 | 28 |

LISTING NO. 2

Sheet 12

| | | | | | | | | | | | | | | | | |
|---|---|---|---|---|---|---|---|---|---|---|---|---|---|---|---|---|
| 4C00 | 2 | 61 | 1 | D6 | 0 | 2 | B9 | 2 | 4D | 0 | 8 | 44 | 4F | 47 | F7 | 4B |
| 4C10 | 3A | 0 | 7E | 2D | B7 | 1 | 3 | 30 | 95 | 3 | 8E | 20 | 17 | 0 | 8 | 56 |
| 4C20 | 2 | 77 | 1 | D6 | 0 | 15 | 46 | 2 | B9 | 2 | FD | 4B | 7 | 37 | 6D | 22 |
| 4C30 | 28 | 2 | E0 | 4A | 46 | 2 | 8B | 3 | CC | 0 | 21 | 17 | 0 | C | 56 | 2 |
| 4C40 | 77 | 1 | D6 | 0 | 15 | 46 | 2 | AA | 2 | 7 | 37 | 6D | 22 | EA | 4B | 28 |
| 4C50 | 2 | E0 | 4A | 46 | 2 | 8B | 3 | CC | 0 | 2 | 95 | 3 | 46 | 2 | 38 | 2 |
| 4C60 | D6 | 0 | B7 | 38 | 2 | 7E | 2D | C6 | 1 | 4D | 0 | 5 | 53 | 48 | 41 | A |
| 4C70 | 4C | 3A | 0 | 9F | 38 | 8B | 3 | F | 0 | 0 | 80 | 17 | 0 | 4 | 8F | 30 |
| 4C80 | 7B | 35 | 9F | 38 | F | 0 | 0 | 80 | F | 0 | 0 | 80 | 17 | 0 | 4 | 8F |
| 4C90 | 30 | 7B | 35 | 4D | 0 | 2 | 58 | 40 | 20 | 80 | 4B | 9D | 4C | 2B | C0 | 8A |
| 4CA0 | 6 | 19 | 39 | 50 | AD | 97 | FF | 25 | 2 | 59 | 40 | 20 | E4 | 4B | B0 | 4C |
| 4CB0 | 2B | C0 | 8A | 6 | 1A | 39 | 50 | AD | 97 | FF | 25 | 2 | 58 | 21 | 20 | 95 |
| 4CC0 | 4C | C3 | 4C | 58 | 88 | 6 | 19 | 39 | AD | 97 | FF | 25 | 2 | 59 | 21 | 20 |
| 4CD0 | A8 | 4C | D4 | 4C | 58 | 88 | 6 | 1A | 39 | AD | 97 | FF | 25 | 2 | 56 | 40 |
| 4CE0 | 20 | 68 | 4B | 3A | 0 | D | 39 | B7 | 1 | 17 | 39 | B7 | 1 | 14 | 30 | 4D |
| 4CF0 | 0 | 2 | 56 | 21 | 20 | DD | 4C | 3A | 0 | D | 39 | B7 | 1 | 17 | 39 | B7 |
| 4D00 | 1 | 43 | 30 | 4D | 0 | 5 | 48 | 4C | 49 | BB | 4C | 3A | 0 | D2 | 4C | E2 |
| 4D10 | 0 | 28 | 2 | 79 | 2 | C1 | 4C | F7 | 4C | F1 | 0 | F5 | 38 | 2 | 4D | 0 |
| 4D20 | 5 | 56 | 4C | 49 | F1 | 4C | 3A | 0 | C1 | 4C | E2 | 0 | 28 | 2 | 79 | 2 |
| 4D30 | D2 | 4C | F7 | 4C | F1 | 0 | F5 | 38 | 2 | 4D | 0 | 4 | 52 | 47 | 42 | CE |
| 4D40 | 49 | 3A | 0 | F | 0 | 0 | 1 | F8 | 2 | 88 | 2 | 28 | 2 | F | 0 | 0 |
| 4D50 | 10 | 88 | 2 | E2 | 0 | B3 | 38 | 79 | 2 | 43 | 30 | F | 0 | 0 | F8 | 7 |
| 4D60 | 1 | F3 | 4D | 0 | 5 | 43 | 52 | 41 | 6B | 4C | 3A | 0 | F | 0 | 0 | 1 |
| 4D70 | 8B | 3 | E2 | 0 | 79 | 2 | 28 | 2 | 35 | 4 | 17 | 0 | 5 | 8F | 30 | 41 |
| 4D80 | 4D | F1 | 0 | F0 | 38 | 2 | 4D | 0 | 8 | 43 | 52 | 41 | 64 | 4D | 90 | 4D |
| 4D90 | 59 | 5F | 5A | 6 | 53 | 8B | D9 | 8E | 6 | B5 | 38 | 86 | F2 | 3 | D7 | 8B |
| 4DA0 | FA | 8A | 6 | EF | 3B | F3 | AA | 8A | 6 | F9 | 3B | 81 | C2 | 0 | 8 | 8B |
| 4DB0 | FA | 8B | CB | F3 | AA | 8A | 6 | 3 | 3C | 81 | C2 | 0 | 8 | 8B | FA | 8B |
| 4DC0 | CB | F3 | AA | 5B | 7 | AD | 97 | FF | 25 | 3 | 50 | 4D | 58 | F1 | 49 | 99 |
| 4DD0 | 0 | 8B | 16 | 27 | 3A | D1 | EA | 2B | DA | D1 | E2 | 3 | D3 | 8A | FA | 8A |
| 4DE0 | F3 | 8A | 16 | 31 | 3A | 8B | CF | 8B | F2 | 26 | AC | 3C | FF | 75 | 6 | FF |
| 4DF0 | 6 | F5 | 39 | EB | 6 | 3A | E0 | 73 | 2 | 8A | E0 | E2 | EC | 80 | C6 | 1 |
| 4E00 | 3A | FE | 75 | E1 | C3 | 4 | 50 | 4D | 41 | C9 | 4D | D | 4E | 6 | 8E | 6 |
| 4E10 | A1 | 38 | 56 | 53 | 2B | C0 | 89 | 6 | F5 | 39 | 8B | 16 | 31 | 3A | 8B | E |
| 4E20 | 3B | 3A | 2B | CA | 8B | F9 | 8B | 1E | 13 | 3A | E8 | A4 | FF | 8B | 1E | 1D |
| 4E30 | 3A | E8 | 9D | FF | 5B | 5E | 7 | 2B | D2 | 8A | D4 | 52 | AD | 97 | FF | 25 |
| 4E40 | 7 | 49 | 4E | 52 | CC | 4C | 3A | 0 | 28 | 2 | F | 0 | FE | 0 | 9B | 1 |
| 4E50 | 46 | 2 | DF | 39 | B7 | 1 | E9 | 39 | B7 | 1 | 99 | 2 | A9 | 1 | 2E | 1 |
| 4E60 | 4D | 0 | 7 | 41 | 44 | 4A | 3B | 4D | 3A | 0 | 44 | 32 | F | 0 | FE | 0 |
| 4E70 | 9F | 48 | B4 | 48 | 44 | 32 | B | 4E | 28 | 2 | F | 0 | FF | 0 | DF | 39 |
| 4E80 | B7 | 1 | 95 | 22 | 28 | 2 | 67 | 2 | F | 0 | FF | 0 | 67 | 2 | 95 | 22 |
| 4E90 | DF | 39 | B7 | 1 | E9 | 39 | B7 | 1 | 88 | 2 | A9 | 1 | D6 | 0 | 2 | AA |
| 4EA0 | 2 | 28 | 2 | F | 0 | FE | 0 | A9 | 1 | D6 | 0 | 6 | 38 | 2 | F | 0 |
| 4EB0 | FE | 0 | 9F | 48 | 4D | 0 | 8 | 46 | 4F | 4F | 20 | 4D | 3A | 0 | B | 4E |
| 4EC0 | 46 | 4E | 61 | 3 | F3 | 39 | B7 | 1 | FD | 39 | B7 | 1 | A9 | 1 | 3F | 1 |
| 4ED0 | 4D | 0 | 7 | 41 | 47 | 43 | 62 | 4E | 3A | 0 | 17 | 0 | 10 | A | 32 | B4 |

| | | | | | | | | | | | | | |
|---|---|---|---|---|---|---|---|---|---|---|---|---|---|
| 4EE0 | 48 | 44 | 32 | 44 | 32 | BC | 4E | D6 | 0 | 2 | 68 | 4E | 6D | 32 | D6 | 0 |
| 4EF0 | EE | 17 | 0 | 10 | 1F | 32 | BC | 4E | 28 | 2 | 7 | 3A | C6 | 1 | D6 | 0 |
| 4F00 | 4B | F | 0 | 80 | 0 | 8B | 3 | E2 | 0 | EB | 30 | F1 | 0 | FB | E4 | 5 |
| 4F10 | 15 | 8 | 16 | 4F | 75 | 74 | 20 | 6F | 66 | 20 | 72 | 61 | 6E | 67 | 65 | 2E |
| 4F20 | 20 | 20 | 50 | 4D | 41 | 58 | 20 | 3D | 20 | B | 4E | 35 | 7 | 17 | 0 | 3 |
| 4F30 | 6C | 6 | F3 | 39 | 45 | 7 | 15 | 8 | 11 | 70 | 69 | 78 | 65 | 6C | 73 | 20 |
| 4F40 | 73 | 61 | 74 | 75 | 72 | 61 | 74 | 65 | 64 | 20 | E4 | 5 | 4D | 0 | 4 | 4F |
| 4F50 | 41 | 44 | 5 | 4E | 99 | 0 | 45 | 20 | 3 | 4F | 43 | 58 | 4E | 4F | 99 | 0 |
| 4F60 | 40 | 0 | 3 | 4F | 43 | 59 | 58 | 4F | 99 | 0 | 40 | 0 | 3 | 4F | 58 | 40 |
| 4F70 | 62 | 4F | 74 | 4F | 2B | C0 | 8A | 6 | 56 | 4F | 50 | AD | 97 | FF | 25 | 3 |
| 4F80 | 4F | 59 | 40 | 6C | 4F | 87 | 4F | 2B | C0 | 8A | 6 | 57 | 4F | 50 | AD | 97 |
| 4F90 | FF | 25 | 3 | 4F | 58 | 21 | 7F | 4F | 9A | 4F | 58 | 88 | 6 | 56 | 4F | AD |
| 4FA0 | 97 | FF | 25 | 3 | 4F | 59 | 21 | 92 | 4F | AB | 4F | 58 | 88 | 6 | 57 | 4F |
| 4FB0 | AD | 97 | FF | 25 | 2 | 4F | 21 | 20 | A3 | 4F | 3A | 0 | A9 | 38 | 54 | 4F |
| 4FC0 | B7 | 1 | 43 | 30 | 4D | 0 | 2 | 2B | 3E | 20 | 6A | 49 | 3A | 0 | 9F | 38 |
| 4FD0 | 68 | 4F | B7 | 1 | F | 0 | 0 | 1 | F8 | 2 | 9F | 38 | 17 | 0 | 0 | F |
| 4FE0 | 0 | 80 | 0 | 6E | 30 | 5E | 4F | B7 | 1 | C1 | 4C | F | 0 | E0 | 0 | 8B |
| 4FF0 | 3 | E2 | 0 | 79 | 2 | D2 | 4C | E3 | 4C | 9F | 38 | F | 0 | 0 | 1 | 79 |

LISTING NO. 2

Sheet 13

| | | | | | | | | | | | | | |
|---|---|---|---|---|---|---|---|---|---|---|---|---|---|
| 5000 | 2 | 88 | 2 | 43 | 30 | F1 | 0 | EB | 4D | 0 | 2 | 3E | 2B | 20 | 87 | 48 |
| 5010 | 3A | 0 | 9F | 38 | 17 | 0 | 0 | 9F | 38 | 68 | 4F | B7 | 1 | F | 0 | 0 |
| 5020 | 1 | F8 | 2 | F | 0 | 80 | 0 | 6E | 30 | 5E | 4F | B7 | 1 | C1 | 4C | F |
| 5030 | 0 | E0 | 0 | 8B | 3 | E2 | 0 | 9F | 38 | F | 0 | 0 | 1 | 79 | 2 | 88 |
| 5040 | 2 | 14 | 30 | 79 | 2 | D2 | 4C | F7 | 4C | F1 | 0 | EB | 4D | 0 | 3 | 2B |
| 5050 | 3E | 2B | C6 | 4F | 3A | 0 | 9F | 38 | 68 | 4F | B7 | 1 | F | 0 | 0 | 1 |
| 5060 | F8 | 2 | 28 | 2 | F | 0 | 80 | 0 | 88 | 2 | 46 | 2 | 9F | 38 | 46 | 2 |
| 5070 | F | 0 | 80 | 0 | 6E | 30 | F | 0 | E0 | 0 | 8B | 3 | E2 | 0 | 5E | 4F |
| 5080 | B7 | 1 | F | 0 | 80 | 0 | 88 | 2 | C1 | 4C | 79 | 2 | D2 | 4C | E3 | 4C |
| 5090 | 5E | 4F | B7 | 1 | C1 | 4C | F7 | 4C | F1 | 0 | E3 | 4D | 0 | 6 | 4F | 48 |
| 50A0 | 4C | B4 | 4F | 3A | 0 | A9 | 4F | E2 | 0 | 28 | 2 | 79 | 2 | 98 | 4F | BA |
| 50B0 | 4F | F1 | 0 | F5 | 38 | 2 | 4D | 0 | 6 | 4F | 56 | 4C | 9D | 50 | 3A | 0 |
| 50C0 | 98 | 4F | E2 | 0 | 28 | 2 | 79 | 2 | A9 | 4F | BA | 4F | F1 | 0 | F5 | 38 |
| 50D0 | 2 | 4D | 0 | 7 | 2B | 4F | 48 | 4E | 50 | 3A | 0 | 95 | 3 | F | 0 | 80 |
| 50E0 | 0 | 17 | 0 | 0 | 68 | 4F | B7 | 1 | A3 | 50 | 10 | 50 | 8B | 3 | F | 0 |
| 50F0 | 0 | 1 | F | 0 | 80 | 0 | 68 | 4F | B7 | 1 | A3 | 50 | 68 | 4F | D5 | 1 |
| 5100 | 8B | 3 | F | 0 | 80 | 0 | 17 | 0 | 0 | 68 | 4F | B7 | 1 | A3 | 50 | 8B |
| 5110 | 3 | F | 0 | E0 | 0 | 17 | 0 | 0 | 5E | 4F | B7 | 1 | F | 0 | 80 | 0 |
| 5120 | 6D | 22 | BE | 50 | 95 | 3 | F | 0 | FF | 0 | F | 0 | 80 | 0 | 68 | 4F |
| 5130 | B7 | 1 | A3 | 50 | 95 | 3 | F | 0 | E0 | 0 | 17 | 0 | 0 | 5E | 4F | B7 |
| 5140 | 1 | F | 0 | 80 | 0 | 88 | 2 | BE | 50 | CC | 4F | 54 | 50 | 8B | 3 | 4D |
| 5150 | 0 | 7 | 2B | 4F | 56 | D3 | 50 | 3A | 0 | 95 | 3 | F | 0 | E0 | 0 | 8B |
| 5160 | 3 | 5E | 4F | B7 | 1 | BE | 50 | 10 | 50 | 8B | 3 | F | 0 | E0 | 0 | 8B |
| 5170 | 3 | 5E | 4F | B7 | 1 | F | 0 | 80 | 0 | 88 | 2 | BE | 50 | 5E | 4F | D5 |
| 5180 | 1 | 8B | 3 | F | 0 | E0 | 0 | 8B | 3 | 5E | 4F | B7 | 1 | BE | 50 | 8B |
| 5190 | 3 | F | 0 | 80 | 0 | 8B | 3 | 68 | 4F | B7 | 1 | A3 | 50 | 95 | 3 | F |
| 51A0 | 0 | FF | 0 | F | 0 | 80 | 0 | 68 | 4F | B7 | 1 | A3 | 50 | 95 | 3 | F |
| 51B0 | 0 | E0 | 0 | 17 | 0 | 0 | 5E | 4F | B7 | 1 | F | 0 | 80 | 0 | 88 | 2 |
| 51C0 | BE | 50 | CC | 4F | 54 | 50 | 8B | 3 | 4D | 0 | 8 | 21 | 52 | 45 | D2 | 4E |
| 51D0 | 3A | 0 | F | 0 | 5A | A5 | 4 | 47 | 57 | 30 | 4D | 0 | 8 | 40 | 52 | 45 |
| 51E0 | B8 | 50 | 3A | 0 | 4 | 47 | 2B | 30 | 4D | 0 | 7 | 54 | 49 | 4C | 88 | 4D |
| 51F0 | 3A | 0 | E2 | 51 | F | 0 | A5 | 5A | 77 | 1 | D6 | 0 | F5 | 4D | 0 | 5 |
| 5200 | 49 | 4F | 52 | 40 | 4E | 3A | 0 | E | 47 | 43 | 30 | D0 | 51 | F0 | 51 | 4D |
| 5210 | 0 | 3 | 41 | 49 | 4E | CA | 51 | 3A | 0 | 22 | 47 | 43 | 30 | FE | 47 | 5 |
| 5220 | 52 | 2C | 47 | 14 | 30 | 4D | 0 | 4 | 41 | 4F | 55 | 11 | 52 | 3A | 0 | 22 |
| 5230 | 47 | 43 | 30 | 2C | 47 | 43 | 30 | F4 | 47 | 5 | 52 | 4D | 0 | 5 | 50 | 42 |
| 5240 | 4F | DC | 51 | 3A | 0 | 44 | 32 | 17 | 0 | 2 | 2D | 52 | 4D | 0 | 5 | 50 |
| 5250 | 43 | 4F | 3D | 52 | 3A | 0 | 17 | 0 | 4 | 2D | 52 | 4D | 0 | 5 | 41 | 57 |

| | | | | | | | | | | | | | | |
|---|---|---|---|---|---|---|---|---|---|---|---|---|---|---|
| 5260 | 49 | 27 | 52 | 3A | 0 | 8B | 3 | 54 | 52 | 4D | 0 | 5 | 41 | 53 | 4E | 5D |
| 5270 | 52 | 3A | 0 | 95 | 3 | 54 | 52 | 4D | 0 | 5 | 41 | 56 | 52 | 6B | 52 | 3A |
| 5280 | 0 | 28 | 2 | 72 | 47 | 43 | 30 | 43 | 52 | 17 | 0 | 2 | 54 | 52 | 4D | 0 |
| 5290 | 5 | 57 | 48 | 45 | 5 | 4D | 3A | 0 | 28 | 2 | 7C | 47 | 43 | 30 | 43 | 52 |
| 52A0 | 17 | 0 | 8 | 54 | 52 | 4D | 0 | 3 | 5A | 45 | 45 | FF | 51 | 3A | 0 | 28 |
| 52B0 | 2 | 90 | 47 | 43 | 30 | 43 | 52 | 17 | 0 | A | 54 | 52 | 4D | 0 | 4 | 48 |
| 52C0 | 4D | 49 | 90 | 52 | 3A | 0 | 28 | 2 | 9A | 47 | 43 | 30 | 43 | 52 | 17 | 0 |
| 52D0 | B | 54 | 52 | 4D | 0 | 4 | 56 | 45 | 52 | B6 | 4E | 3A | 0 | 28 | 2 | A4 |
| 52E0 | 47 | 43 | 30 | 43 | 52 | 17 | 0 | 20 | 54 | 52 | 4D | 0 | 3 | 41 | 4D | 41 |
| 52F0 | 79 | 52 | 3A | 0 | 28 | 2 | AE | 47 | 43 | 30 | 43 | 52 | 17 | 0 | 21 | 54 |
| 5300 | 52 | 4D | 0 | 4 | 48 | 4D | 41 | BE | 52 | 3A | 0 | 28 | 2 | B8 | 47 | 43 |
| 5310 | 30 | 43 | 52 | 17 | 0 | 22 | 54 | 52 | 4D | 0 | 5 | 4C | 4F | 57 | 51 | 51 |
| 5320 | 3A | 0 | 28 | 2 | 86 | 47 | 43 | 30 | 43 | 52 | 17 | 0 | 9 | 54 | 52 | 4D |
| 5330 | 0 | 5 | 55 | 50 | 50 | D5 | 52 | 3A | 0 | 28 | 2 | C2 | 47 | 43 | 30 | 43 |
| 5340 | 52 | 17 | 0 | 29 | 54 | 52 | 4D | 0 | 9 | 57 | 52 | 49 | 3 | 53 | 3A | 0 |
| 5350 | CC | 47 | EE | 31 | CC | 47 | 14 | 30 | 43 | 52 | 17 | 0 | 2A | 54 | 52 | 4D |
| 5360 | 0 | 7 | 43 | 41 | 4C | EA | 51 | 3A | 0 | 95 | 3 | 4E | 53 | 4D | 0 | 6 |
| 5370 | 4D | 4F | 54 | A | 50 | 3A | 0 | 17 | 0 | 2 | 4E | 53 | 4D | 0 | 8 | 4D |
| 5380 | 41 | 49 | 6F | 53 | 3A | 0 | 17 | 0 | 4 | 4E | 53 | 4D | 0 | 8 | 46 | 41 |
| 5390 | 43 | 31 | 53 | 3A | 0 | 17 | 0 | 8 | 4E | 53 | 4D | 0 | 7 | 41 | 43 | 41 |
| 53A0 | EC | 52 | 3A | 0 | 17 | 0 | 20 | 4E | 53 | 4D | 0 | 9 | 53 | 49 | 54 | 61 |
| 53B0 | 53 | 3A | 0 | 17 | 0 | 40 | 4E | 53 | 4D | 0 | 7 | 53 | 54 | 41 | AB | 53 |
| 53C0 | 3A | 0 | F | 0 | FF | 0 | 50 | 1 | F | 0 | 80 | 0 | 4E | 53 | 4D | 0 |
| 53D0 | 7 | 57 | 52 | 49 | 48 | 53 | 3A | 0 | D6 | 47 | EE | 31 | D6 | 47 | 14 | 30 |
| 53E0 | 43 | 52 | 17 | 0 | 2B | 54 | 52 | 4D | 0 | 6 | 4D | 49 | 52 | 7E | 53 | 3A |
| 53F0 | 0 | F | 0 | FF | 0 | 50 | 1 | 17 | 0 | 4 | D6 | 53 | 4D | 0 | 7 | 43 |

LISTING NO. 2

Sheet 14

| | | | | | | | | | | | | | | | |
|---|---|---|---|---|---|---|---|---|---|---|---|---|---|---|---|
| 5400 | 48 | 4F | BA | 53 | 3A | 0 | F | 0 | FF | 0 | 50 | 1 | 17 | 0 | 4 | D6 |
| 5410 | 53 | 4D | 0 | 7 | 53 | 54 | 52 | FE | 53 | 3A | 0 | 17 | 0 | 8 | D6 | 53 |
| 5420 | 4D | 0 | A | 43 | 41 | 4C | 13 | 54 | 3A | 0 | 17 | 0 | 10 | D6 | 53 | 4D |
| 5430 | 0 | 6 | 4D | 41 | 4E | E9 | 53 | 3A | 0 | F | 0 | FF | 0 | 50 | 1 | F |
| 5440 | 0 | 80 | 0 | D6 | 53 | 4D | 0 | 7 | 41 | 55 | 54 | 9C | 53 | 3A | 0 | 8 |
| 5450 | 48 | 5 | 52 | 4D | 0 | 3 | 41 | 43 | 40 | 47 | 54 | 3A | 0 | 36 | 47 | 57 |
| 5460 | 30 | 40 | 47 | 57 | 30 | 12 | 48 | 5 | 52 | 2C | 47 | 14 | 30 | 4D | 0 | 8 |
| 5470 | 45 | 59 | 45 | 8D | 53 | 3A | 0 | 8B | 3 | 4A | 47 | 43 | 30 | 8B | 3 | 54 |
| 5480 | 47 | 43 | 30 | 1C | 48 | 5 | 52 | 4D | 0 | 9 | 45 | 59 | 45 | 6F | 54 | 3A |
| 5490 | 0 | 26 | 48 | 5 | 52 | 4D | 0 | 6 | 4F | 43 | 52 | 4E | 52 | 3A | 0 | 35 |
| 54A0 | 4 | 6 | 2 | 6 | 2 | 67 | 2 | 28 | 2 | A4 | 21 | 46 | 2 | 17 | 0 | 8 |
| 54B0 | 88 | 2 | 28 | 2 | 17 | 0 | 10 | 99 | 2 | 67 | 2 | A3 | 50 | 17 | 2 | 17 |
| 54C0 | 2 | 17 | 0 | 8 | 88 | 2 | 28 | 2 | 17 | 0 | 10 | 99 | 2 | 67 | 2 | BE |
| 54D0 | 50 | 4D | 0 | 5 | 58 | 59 | 45 | D0 | 53 | 3A | 0 | 4 | 47 | 17 | 0 | 20 |
| 54E0 | 88 | 2 | 14 | 30 | 17 | 0 | 40 | 88 | 2 | B7 | 39 | B7 | 1 | 88 | 2 | 4 |
| 54F0 | 47 | 17 | 0 | 22 | 88 | 2 | 14 | 30 | 17 | 0 | 40 | 88 | 2 | C1 | 39 | B7 |
| 5500 | 1 | 88 | 2 | 4D | 0 | 3 | 41 | 49 | 4D | 55 | 54 | 3A | 0 | D9 | 54 | 35 |
| 5510 | 4 | 93 | 3A | B7 | 1 | 77 | 1 | 46 | 2 | 75 | 3A | B7 | 1 | 77 | 1 | 2E |
| 5520 | 1 | 61 | 1 | D6 | 0 | 25 | 44 | 32 | 8B | 3 | 75 | 3A | B7 | 1 | 93 | 3A |
| 5530 | B7 | 1 | 9D | 54 | 35 | 4 | 93 | 3A | C6 | 1 | 75 | 3A | C6 | 1 | 95 | 3 |
| 5540 | 67 | 2 | 67 | 2 | 44 | 32 | 9D | 54 | CC | 0 | 2 | 48 | 4 | 4D | 0 | 2 |
| 5550 | 4E | 4D | 20 | 31 | 54 | 3A | 0 | 17 | 0 | 9 | 17 | 0 | 17 | 95 | 22 | 17 |
| 5560 | 0 | 1F | 99 | 2 | 4D | 0 | 4 | 41 | 46 | 49 | 5 | 55 | 3A | 0 | 17 | 0 |
| 5570 | 14 | 37 | 53 | 8B | 3 | 20 | 53 | 4D | 0 | 4 | 44 | 46 | 49 | 22 | 54 | 3A |
| 5580 | 0 | F7 | 49 | D6 | 0 | A | 17 | 0 | 78 | F | 0 | D6 | 0 | CC | 0 | 8 |
| 5590 | F | 0 | 84 | 0 | F | 0 | B8 | 0 | 37 | 53 | 20 | 53 | 4D | 0 | 9 | 4D |
| 55A0 | 4F | 54 | 4F | 55 | 3A | 0 | 6C | 55 | F | 0 | 30 | 2 | 55 | 55 | 96 | 52 |
| 55B0 | F | 0 | 9A | 0 | AD | 52 | F | 0 | 80 | 0 | C4 | 52 | F | 0 | 80 | 0 |

| | | | | | | | | | | | | | | | |
|---|---|---|---|---|---|---|---|---|---|---|---|---|---|---|---|
| 55C0 | DB | 52 | F | 0 | C0 | 0 | F2 | 52 | 17 | 0 | 32 | 9 | 53 | F | 0 | 9B |
| 55D0 | 0 | 7F | 52 | 4D | 0 | 4 | 48 | 4F | 4D | D3 | 54 | 3A | 0 | 2F | 37 | 37 |
| 55E0 | 54 | A4 | 55 | 2F | 37 | 75 | 53 | 2F | 37 | C0 | 53 | 2F | 37 | B1 | 53 | 2F |
| 55F0 | 37 | A2 | 53 | 2F | 37 | 4 | 54 | EF | 48 | 16 | 49 | 17 | 0 | 4 | 6A | 4D |
| 5600 | F | 0 | FF | 0 | F | 0 | FF | 0 | F | 0 | FF | 0 | 17 | 0 | 0 | 17 |
| 5610 | 0 | 0 | 41 | 4D | 4D | 37 | 84 | 53 | 4D | 0 | 3 | 4E | 4F | 50 | 9E | 55 |
| 5620 | 3A | 0 | 4D | 0 | 2 | 3A | 4B | 20 | A7 | 52 | 3A | 0 | 4 | 6 | 17 | 0 |
| 5630 | 8 | 88 | 2 | 46 | 2 | 75 | 37 | C6 | 1 | 26 | 0 | 4D | 0 | 3 | 3A | 4B |
| 5640 | 43 | 24 | 56 | 3A | 0 | 4 | 6 | 17 | 0 | 8 | 88 | 2 | 46 | 2 | 75 | 37 |
| 5650 | 28 | 2 | 6 | 2 | C6 | 1 | 17 | 2 | 46 | 2 | 87 | 38 | C6 | 1 | 26 | 0 |
| 5660 | 4D | 0 | 6 | 2B | 43 | 59 | 1A | 53 | 3A | 0 | 95 | 38 | B7 | 1 | AA | 2 |
| 5670 | 7D | 38 | 6D | 22 | 28 | 2 | 95 | 38 | C6 | 1 | 87 | 38 | B7 | 1 | B7 | 1 |
| 5680 | 9E | 5 | 4D | 0 | A | 4D | 4F | 4E | 1A | 56 | 3A | 0 | 15 | 8 | 3 | 20 |
| 5690 | 4F | 4B | E4 | 5 | 17 | 0 | 10 | 1F | 32 | 61 | 1 | 4D | 0 | 6 | 24 | 53 |
| 56A0 | 50 | 79 | 55 | 3A | 0 | 68 | 56 | 4D | 0 | 3 | 24 | 43 | 52 | 9D | 56 | 3A |
| 56B0 | 0 | 8A | 56 | 4D | 0 | 4 | 53 | 41 | 56 | A9 | 56 | 3A | 0 | CB | 39 | B7 |
| 56C0 | 1 | 28 | 2 | 7 | 37 | B9 | 2 | A9 | 1 | 46 | 2 | 11 | 37 | AA | 2 | 9B |
| 56D0 | 1 | 2E | 1 | D6 | 0 | 45 | E4 | 5 | CB | 39 | B7 | 1 | 28 | 2 | 15 | 8 |
| 56E0 | 10 | 53 | 61 | 76 | 69 | 6E | 67 | 20 | 64 | 61 | 74 | 61 | 20 | 73 | 65 | 74 |
| 56F0 | 20 | 35 | 7 | 15 | 8 | 4 | 2D | 2D | 2D | 20 | 27 | 4B | 17 | 0 | 28 | 8B |
| 5700 | 3 | E2 | 0 | EB | 30 | F1 | 0 | FB | 15 | 8 | 7 | 20 | 64 | 6F | 6E | 65 |
| 5710 | 2E | 20 | 95 | 3 | CB | 39 | D5 | 1 | CC | 0 | 3A | E4 | 5 | EB | 30 | 15 |
| 5720 | 8 | 2D | 44 | 69 | 73 | 6B | 20 | 66 | 75 | 6C | 6C | 2E | 20 | 20 | 49 | 6E |
| 5730 | 73 | 65 | 72 | 74 | 20 | 61 | 6E | 6F | 74 | 68 | 65 | 72 | 20 | 64 | 69 | 73 |
| 5740 | 6B | 20 | 74 | 6F | 20 | 63 | 6F | 6E | 74 | 69 | 6E | 75 | 65 | 2E | 20 | 7 |
| 5750 | 37 | CB | 39 | C6 | 1 | 4D | 0 | 2 | 24 | 43 | 20 | B5 | 56 | 3A | 0 | 2F |
| 5760 | 37 | 70 | 49 | 8B | 3 | 95 | 38 | C6 | 1 | 4D | 0 | 2 | 24 | 41 | 20 | 57 |
| 5770 | 57 | 3A | 0 | 4D | 37 | 70 | 49 | D8 | 4E | 95 | 3 | 95 | 38 | C6 | 1 | 4D |
| 5780 | 0 | 2 | 24 | 53 | 20 | 6B | 57 | 3A | 0 | 7 | 3A | B7 | 1 | 61 | 3 | D6 |
| 5790 | 0 | 2 | BB | 56 | 17 | 0 | 2 | 95 | 38 | C6 | 1 | 4D | 0 | 2 | 24 | 52 |
| 57A0 | 20 | 81 | 57 | 3A | 0 | F | 0 | 80 | 2 | 55 | 55 | 96 | 52 | 4D | 0 | 2 |
| 57B0 | 24 | 59 | 20 | 9D | 57 | 3A | 0 | F | 0 | 44 | 2 | 55 | 55 | 96 | 52 | 4D |
| 57C0 | 0 | 2 | 24 | 47 | 20 | AF | 57 | 3A | 0 | F | 0 | 30 | 2 | 55 | 55 | 96 |
| 57D0 | 52 | 4D | 0 | 2 | 24 | 42 | 20 | C1 | 57 | 3A | 0 | F | 0 | AE | 1 | 55 |
| 57E0 | 55 | 96 | 52 | 4D | 0 | 2 | 4F | 50 | 20 | 97 | 54 | 99 | 0 | 45 | 20 | 6 |
| 57F0 | 3F | 52 | 41 | E5 | 57 | 3A | 0 | 6 | 2 | 56 | 2 | 9B | 1 | 17 | 2 | 67 |

LISTING NO. 2

Sheet 15

| | | | | | | | | | | | | | | | |
|---|---|---|---|---|---|---|---|---|---|---|---|---|---|---|---|
| 5800 | 2 | A9 | 1 | 3F | 1 | 61 | 3 | 4D | 0 | 6 | 43 | 48 | 41 | D3 | 57 | 3A |
| 5810 | 0 | 14 | 30 | 28 | 2 | 67 | 2 | 88 | 2 | 28 | 2 | F | 0 | FF | 0 | 8B |
| 5820 | 3 | F5 | 57 | D6 | 0 | 2 | 46 | 2 | 38 | 2 | 4D | 0 | 6 | 2B | 41 | 56 |
| 5830 | 62 | 56 | 3A | 0 | 72 | 47 | F | 58 | 7F | 52 | 4D | 0 | 6 | 2B | 57 | 48 |
| 5840 | 2C | 58 | 3A | 0 | 7C | 47 | F | 58 | 96 | 52 | 4D | 0 | 6 | 2B | 4C | 4F |
| 5850 | 3C | 58 | 3A | 0 | 86 | 47 | F | 58 | 20 | 53 | 4D | 0 | 4 | 2B | 5A | 45 |
| 5860 | 4C | 58 | 3A | 0 | 90 | 47 | F | 58 | AD | 52 | 4D | 0 | 5 | 2B | 56 | 45 |
| 5870 | 5C | 58 | 3A | 0 | A4 | 47 | F | 58 | DB | 52 | 4D | 0 | 4 | 2B | 41 | 4D |
| 5880 | 6C | 58 | 3A | 0 | AE | 47 | F | 58 | F2 | 52 | 4D | 0 | 5 | 2B | 48 | 4D |
| 5890 | 7C | 58 | 3A | 0 | B8 | 47 | F | 58 | 9 | 53 | 4D | 0 | 6 | 2B | 55 | 50 |
| 58A0 | 8C | 58 | 3A | 0 | C2 | 47 | F | 58 | 37 | 53 | 4D | 0 | 6 | 2B | 48 | 42 |
| 58B0 | 9C | 58 | 3A | 0 | 4A | 47 | 14 | 30 | 88 | 2 | 4A | 47 | 43 | 30 | 4D | 0 |
| 58C0 | 6 | 2B | 56 | 42 | AC | 58 | 3A | 0 | 54 | 47 | 14 | 30 | 88 | 2 | 54 | 47 |
| 58D0 | 43 | 30 | 4D | 0 | 2 | 24 | 32 | 20 | 9 | 58 | 3A | 0 | 95 | 3 | A2 | 58 |
| 58E0 | 4D | 0 | 2 | 24 | 34 | 20 | D4 | 58 | 3A | 0 | 95 | 3 | 52 | 58 | 4D | 0 |
| 58F0 | 2 | 24 | 36 | 20 | E2 | 58 | 3A | 0 | 17 | 0 | FF | 52 | 58 | 4D | 0 | 2 |
| 5900 | 24 | 38 | 20 | F0 | 58 | 3A | 0 | 17 | 0 | FF | A2 | 58 | 4D | 0 | 5 | 24 |
| 5910 | 44 | 4F | FF | 58 | 3A | 0 | 17 | 0 | FF | 72 | 58 | 4D | 0 | 3 | 24 | 55 |
| 5920 | 50 | E | 59 | 3A | 0 | 95 | 3 | 72 | 58 | 4D | 0 | 5 | 24 | 4C | 45 | 1D |

| | | 59 | | | | | | | | 60 | | | | |
|---|---|---|---|---|---|---|---|---|---|---|---|---|---|---|
| 5930 | 59 | 3A | 0 | 95 | 3 | 92 | 58 | 4D | 0 | 6 | 24 | 52 | 49 | 2B | 59 | 3A |
| 5940 | 0 | 17 | 0 | FF | 92 | 58 | 4D | 0 | 3 | 24 | 2F | 5A | 39 | 59 | 3A | 0 |
| 5950 | 95 | 3 | C6 | 58 | 4D | 0 | 3 | 24 | 2F | 57 | 48 | 59 | 3A | 0 | 17 | 0 |
| 5960 | FF | C6 | 58 | 4D | 0 | 3 | 24 | 2F | 41 | 56 | 59 | 3A | 0 | 95 | 3 | B2 |
| 5970 | 58 | 4D | 0 | 3 | 24 | 2F | 44 | 65 | 59 | 3A | 0 | 17 | 0 | FF | B2 | 58 |
| 5980 | 4D | 0 | 2 | 24 | 37 | 20 | 73 | 59 | 3A | 0 | 17 | 0 | FF | 42 | 58 | 4D |
| 5990 | 0 | 2 | 24 | 39 | 20 | 82 | 59 | 3A | 0 | 95 | 3 | 42 | 58 | 4D | 0 | 2 |
| 59A0 | 24 | 31 | 20 | 91 | 59 | 3A | 0 | 17 | 0 | FF | 62 | 58 | 4D | 0 | 2 | 24 |
| 59B0 | 33 | 20 | 9F | 59 | 3A | 0 | 95 | 3 | 62 | 58 | 4D | 0 | 2 | 24 | 2C | 20 |
| 59C0 | AE | 59 | 3A | 0 | 17 | 0 | FF | 82 | 58 | 4D | 0 | 2 | 24 | 2E | 20 | BC |
| 59D0 | 59 | 3A | 0 | 95 | 3 | 82 | 58 | 4D | 0 | 2 | 24 | 3C | 20 | CB | 59 | 3A |
| 59E0 | 0 | 17 | 0 | FF | 32 | 58 | 4D | 0 | 2 | 24 | 3E | 20 | D9 | 59 | 3A | 0 |
| 59F0 | 95 | 3 | 32 | 58 | 4D | 0 | 2 | 24 | 49 | 20 | E8 | 59 | 3A | 0 | 39 | 37 |
| 5A00 | 19 | 54 | 4D | 0 | 2 | 24 | 4F | 20 | F6 | 59 | 3A | 0 | 57 | 37 | 19 | 54 |
| 5A10 | 4D | 0 | 2 | 24 | 44 | 20 | 4 | 5A | 3A | 0 | 2C | 49 | 4D | 0 | 2 | 24 |
| 5A20 | 46 | 20 | 12 | 5A | 3A | 0 | 16 | 49 | 4D | 0 | 7 | 4D | 4F | 4E | 84 | 56 |
| 5A30 | 3A | 0 | 8B | 3 | 28 | 2 | 17 | 0 | 10 | A | 32 | 6D | 32 | D6 | 0 | 11 |
| 5A40 | F | 0 | D8 | 0 | B6 | 24 | 17 | 0 | 10 | 1F | 32 | 75 | 37 | B7 | 1 | 9E |
| 5A50 | 5 | B | 55 | D6 | 0 | DE | 38 | 2 | 4D | 0 | 3 | 4D | 41 | 4E | 2A | 5A |
| 5A60 | 3A | 0 | 16 | 49 | 4D | 37 | 70 | 49 | 6C | 55 | 2F | 37 | 93 | 53 | 2F | 37 |
| 5A70 | 84 | 53 | 9F | 38 | 8B | 3 | 17 | 0 | FF | F | 0 | FF | 0 | 7B | 35 | F |
| 5A80 | 0 | FF | 0 | 17 | 0 | 0 | 17 | 0 | 0 | 17 | 0 | 0 | 17 | 0 | 0 | 41 |
| 5A90 | 4D | 17 | 0 | 2 | C1 | 39 | C6 | 1 | 17 | 0 | F9 | B7 | 39 | C6 | 1 | 8B |
| 5AA0 | 3 | F | 0 | FF | 0 | 8B | 3 | F | 0 | 80 | 0 | C1 | 39 | B7 | 1 | 88 |
| 5AB0 | 2 | B | 4D | 8B | 3 | F | 0 | FF | 0 | 8B | 3 | F | 0 | 80 | 0 | B7 |
| 5AC0 | 39 | B7 | 1 | 88 | 2 | 26 | 4D | 30 | 5A | 4D | 37 | 93 | 53 | 4D | 0 | 4 |
| 5AD0 | 44 | 41 | 56 | 1E | 5A | 3A | 0 | 4D | 37 | 93 | 53 | 2C | 49 | 7F | 55 | 9F |
| 5AE0 | 38 | 8B | 3 | 17 | 0 | FF | 17 | 0 | 40 | 7B | 35 | F | 0 | FF | 0 | 17 |
| 5AF0 | 0 | 0 | 17 | 0 | 0 | 17 | 0 | 0 | 17 | 0 | 0 | 41 | 4D | 17 | 0 | FE |
| 5B00 | C1 | 39 | C6 | 1 | 8B | 3 | B7 | 39 | C6 | 1 | 8B | 3 | F | 0 | FF | 0 |
| 5B10 | 8B | 3 | F | 0 | 80 | 0 | C1 | 39 | B7 | 1 | 88 | 2 | B | 4D | 8B | 3 |
| 5B20 | F | 0 | FF | 0 | 8B | 3 | F | 0 | 80 | 0 | B7 | 39 | B7 | 1 | 88 | 2 |
| 5B30 | 26 | 4D | 4D | 37 | 68 | 47 | 43 | 30 | 8B | 3 | ED | 3B | C6 | 1 | 8B | 3 |
| 5B40 | F7 | 3B | C6 | 1 | F | 0 | FF | 0 | 1 | 3C | C6 | 1 | 17 | 0 | 4 | 8B |
| 5B50 | 3 | F | 0 | 0 | 1 | 8E | 4D | 75 | 54 | 30 | 5A | 8F | 54 | 4D | 0 | 4 |
| 5B60 | 45 | 58 | 41 | 89 | 54 | 3A | 0 | 3 | 30 | E0 | D | EF | 48 | 8B | 3 | 6A |
| 5B70 | 4D | 17 | 0 | 4 | 6A | 4D | 2F | 37 | B1 | 53 | 4D | 37 | C0 | 53 | 42 | 49 |
| 5B80 | 2F | 37 | 70 | 49 | 2F | 37 | 68 | 47 | 43 | 30 | 75 | 54 | E4 | 5 | E4 | 5 |
| 5B90 | 15 | 8 | 27 | 50 | 72 | 65 | 73 | 73 | 20 | 20 | 27 | 59 | 27 | 20 | 20 | 74 |
| 5BA0 | 6F | 20 | 73 | 74 | 6F | 72 | 65 | 20 | 74 | 68 | 65 | 20 | 6E | 65 | 78 | 74 |
| 5BB0 | 20 | 66 | 72 | 61 | 6D | 65 | 20 | 69 | 6E | 20 | CB | 39 | 45 | 7 | E4 | 5 |
| 5BC0 | 15 | 8 | 17 | 20 | 20 | 20 | 20 | 20 | 20 | 20 | 27 | 4E | 27 | 20 | 20 | 6F |
| 5BD0 | 74 | 68 | 65 | 72 | 77 | 69 | 73 | 65 | 2E | 20 | 8E | 20 | 17 | 0 | 59 | 77 |
| 5BE0 | 1 | 61 | 3 | D6 | 0 | 1B | E4 | 5 | 15 | 8 | 8 | 46 | 72 | 61 | 6D | 65 |
| 5BF0 | 20 | 3D | 20 | 11 | 37 | AA | 2 | 7 | 37 | B9 | 2 | 26 | 31 | CB | 39 | C6 |

LISTING NO. 2

Sheet 16

| 5C00 | 1 | E4 | 5 | 8B | 3 | 95 | 38 | C6 | 1 | 30 | 5A | 8F | 54 | 4D | 37 | 68 |
|---|---|---|---|---|---|---|---|---|---|---|---|---|---|---|---|---|
| 5C10 | 47 | 43 | 30 | 2F | 37 | 37 | 54 | 2F | 37 | C0 | 53 | 4D | 37 | 84 | 53 | F3 |
| 5C20 | 2F | 4D | 0 | 6 | 4E | 4F | 52 | 5A | 5A | 22 | 35 | 4 | 0 | C | 0 | 1A |
| 5C30 | 0 | 34 | 0 | 5C | 0 | 90 | 0 | C5 | 0 | EF | 0 | FF | 0 | EF | 0 | C5 |
| 5C40 | 0 | 90 | 0 | 5C | 0 | 34 | 0 | 1A | 0 | C | 0 | 4 | 0 | 4 | 4C | 53 |
| 5C50 | 41 | C0 | 58 | 3A | 0 | F | 0 | 0 | 1 | F8 | 2 | 9F | 38 | 46 | 2 | 8A |
| 5C60 | 18 | 8B | 3 | 29 | 3C | F | 0 | 0 | 1 | 6E | 30 | 4D | 0 | 5 | 53 | 51 |
| 5C70 | 53 | CF | 5A | 75 | 5C | 59 | 58 | 53 | 56 | 8B | F0 | BA | 0 | 0 | 8B | DA |
| 5C80 | 8B | FA | 2B | C0 | AC | 3 | D0 | F6 | E0 | 3 | D8 | 83 | D7 | 0 | E2 | F2 |
| 5C90 | 8B | C3 | 5E | 5B | 52 | 50 | 57 | AD | 97 | FF | 25 | 6 | 50 | 52 | 44 | EF |

| | | | | | | | | | | | | | |
|---|---|---|---|---|---|---|---|---|---|---|---|---|---|
| 5CA0 | 57 | A3 | 5C | 59 | 5F | 5A | 53 | 55 | 56 | 8B | F2 | BB | 0 | 0 | 8B | EB |
| 5CB0 | 2B | C0 | 8A | 15 | 47 | AC | F6 | E2 | 3 | D8 | 83 | D5 | 0 | E2 | F1 | 8B |
| 5CC0 | C3 | 8B | CD | 5E | 5D | 5B | 50 | 51 | AD | 97 | FF | 25 | 7 | 4E | 50 | 52 |
| 5CD0 | 23 | 5C | D4 | 5C | 59 | 5F | 5A | 53 | 55 | 56 | 8B | F2 | BB | 0 | 0 | 8B |
| 5CE0 | EB | AD | F7 | 2D | 83 | C7 | 2 | 3 | D8 | 13 | EA | E2 | F4 | 8B | C3 | 8B |
| 5CF0 | CD | 5E | 5D | 5B | 50 | 51 | AD | 97 | FF | 25 | 7 | 52 | 53 | 51 | 66 | 55 |
| 5D00 | 3A | 0 | FB | 3A | 12 | 4 | 43 | 3A | B7 | 1 | CD | 22 | CF | 3A | B7 | 1 |
| 5D10 | D9 | 3A | B7 | 1 | 57 | 3A | B7 | 1 | 95 | 22 | 99 | 2 | 28 | 2 | 28 | 2 |
| 5D20 | E3 | 3A | 12 | 4 | 43 | 3A | B7 | 1 | CD | 22 | CF | 3A | B7 | 1 | 28 | 2 |
| 5D30 | BB | 22 | 57 | 3A | B7 | 1 | CD | 22 | 99 | 2 | 95 | 22 | 7 | 3B | B7 | 1 |
| 5D40 | EF | 3A | 12 | 4 | 43 | 3A | B7 | 1 | CD | 22 | D9 | 3A | B7 | 1 | 28 | 2 |
| 5D50 | BB | 22 | 57 | 3A | B7 | 1 | CD | 22 | 99 | 2 | 95 | 22 | 46 | 2 | E6 | 32 |
| 5D60 | 4D | 0 | A | 58 | 43 | 4F | D5 | 55 | 3A | 0 | A7 | 3A | B7 | 1 | 43 | 3A |
| 5D70 | B7 | 1 | 73 | 5C | E3 | 3A | 24 | 4 | CF | 3A | C6 | 1 | 4D | 3A | B7 | 1 |
| 5D80 | 8B | 3 | E2 | 0 | B1 | 3A | B7 | 1 | 79 | 2 | 88 | 2 | 43 | 3A | B7 | 1 |
| 5D90 | 73 | 5C | EF | 3A | 24 | 4 | D9 | 3A | C6 | 1 | A7 | 3A | B7 | 1 | B1 | 3A |
| 5DA0 | B7 | 1 | 79 | 2 | 88 | 2 | 43 | 3A | B7 | 1 | A1 | 5C | FB | 3A | 24 | 4 |
| 5DB0 | 0 | 5D | 79 | 2 | 4B | 40 | C6 | 1 | F1 | 0 | C9 | 4D | 0 | 4 | 50 | 45 |
| 5DC0 | 41 | 9B | 5C | 3A | 0 | F | 0 | 1 | 80 | C5 | 3A | C6 | 1 | 8B | 3 | BB |
| 5DD0 | 3A | C6 | 1 | D8 | 2 | 56 | 2 | 88 | 2 | 46 | 2 | E2 | 0 | C5 | 3A | B7 |
| 5DE0 | 1 | D6 | 32 | 79 | 2 | B7 | 1 | D6 | 32 | 18 | 22 | D6 | 0 | E | 79 | 2 |
| 5DF0 | B7 | 1 | C5 | 3A | C6 | 1 | 79 | 2 | BB | 3A | C6 | 1 | 17 | 0 | 2 | 7 |
| 5E00 | 1 | DB | BB | 3A | B7 | 1 | 4D | 0 | 9 | 49 | 4E | 54 | 3D | 56 | 3A | 0 |
| 5E10 | 28 | 2 | 17 | 0 | 2 | 99 | 2 | 56 | 2 | 17 | 0 | 2 | 88 | 2 | B7 | 1 |
| 5E20 | 67 | 2 | B7 | 1 | 67 | 2 | B7 | 1 | 56 | 2 | 46 | 2 | 99 | 2 | 28 | 2 |
| 5E30 | 6 | 2 | 67 | 2 | 67 | 2 | 46 | 2 | 99 | 2 | 88 | 2 | 17 | 2 | 46 | 2 |
| 5E40 | 4D | 0 | A | 53 | 51 | 55 | 6D | 5C | 3A | 0 | 11 | 3B | B7 | 1 | 8B | 3 |
| 5E50 | E2 | 0 | 95 | 3 | F1 | 0 | FB | F | 0 | 95 | 40 | 11 | 3B | B7 | 1 | E4 |
| 5E60 | 2C | 11 | 3B | B7 | 1 | 28 | 2 | 25 | 3B | C6 | 1 | E8 | 2 | D8 | 2 | 1B |
| 5E70 | 3B | C6 | 1 | 4D | 0 | 4 | 46 | 4C | 54 | 5F | 5B | 3A | 0 | 1B | 3B | B7 |
| 5E80 | 1 | 99 | 2 | F | 0 | 95 | 40 | 11 | 3B | B7 | 1 | D2 | 5C | 25 | 3B | B7 |
| 5E90 | 1 | CD | 22 | 4D | 0 | 6 | 46 | 49 | 4C | 75 | 5E | 3A | 0 | 11 | 3B | B7 |
| 5EA0 | 1 | E8 | 2 | D8 | 2 | 1B | 3B | C6 | 1 | 6 | 2 | 46 | 2 | 17 | 2 | D8 |
| 5EB0 | 2 | 8B | 3 | E2 | 0 | 35 | 4 | 79 | 2 | 88 | 2 | 7B | 5E | 46 | 2 | 79 |
| 5EC0 | 2 | 88 | 2 | C6 | 1 | 17 | 0 | 2 | 7 | 1 | EA | 48 | 4 | 4D | 0 | 8 |
| 5ED0 | 41 | 4C | 54 | FA | 5C | 3A | 0 | 53 | 5C | 68 | 5D | 8B | 3 | 4B | 40 | 1B |
| 5EE0 | 3B | B7 | 1 | 88 | 2 | 8B | 3 | 4B | 40 | 39 | 3B | B7 | 1 | 9B | 5E | 8B |
| 5EF0 | 3 | 4B | 40 | 39 | 3B | B7 | 1 | C3 | 5D | 28 | 2 | B7 | 1 | 46 | 2 | 28 |
| 5F00 | 2 | 8B | 3 | 4B | 40 | 99 | 2 | E8 | 2 | 8B | 3 | 56 | 2 | 9B | 1 | 56 |
| 5F10 | 2 | 39 | 3B | B7 | 1 | B9 | 2 | 9B | 1 | 2E | 1 | D6 | 0 | F | B9 | 2 |
| 5F20 | 2F | 3B | B7 | 1 | F8 | 2 | 46 | 2 | E | 5E | CC | 0 | 1D | 46 | 2 | 38 |
| 5F30 | 2 | 8B | 3 | 56 | 2 | 77 | 1 | D6 | 0 | B | 8B | 3 | 2F | 3B | B7 | 1 |
| 5F40 | D8 | 2 | CC | 0 | 5 | 95 | 3 | 17 | 0 | 2 | 2F | 3B | B7 | 1 | D8 | 2 |
| 5F50 | 46 | 2 | 95 | 22 | 88 | 2 | 4D | 0 | 8 | 46 | 49 | 4C | 95 | 5E | 3A | 0 |
| 5F60 | B9 | 2 | 43 | 3B | C6 | 1 | 43 | 3B | B7 | 1 | 8B | 3 | C5 | 42 | 2F | 3A |
| 5F70 | B7 | 1 | 43 | 3B | B7 | 1 | 2F | 3A | B7 | 1 | C5 | 42 | B7 | 1 | A5 | 2C |
| 5F80 | 43 | 3B | B7 | 1 | 39 | 3A | B7 | 1 | C5 | 42 | F | 0 | 0 | 1 | 39 | 3A |
| 5F90 | B7 | 1 | 99 | 2 | 43 | 3B | B7 | 1 | 39 | 3A | B7 | 1 | C5 | 42 | 17 | 0 |
| 5FA0 | 2 | 99 | 2 | B7 | 1 | A5 | 2C | 4D | 0 | 9 | 53 | 45 | 54 | 42 | 5E | 3A |
| 5FB0 | 0 | F | 0 | 6B | 3 | 56 | 2 | 9B | 1 | D6 | 0 | 9 | 95 | 3 | 11 | 3B |
| 5FC0 | C6 | 1 | CC | 0 | 84 | F | 0 | EE | 2 | 56 | 2 | 9B | 1 | D6 | 0 | A |
| 5FD0 | 17 | 0 | 3 | 11 | 3B | C6 | 1 | CC | 0 | 6F | F | 0 | 71 | 2 | 56 | 2 |
| 5FE0 | 9B | 1 | D6 | 0 | A | 17 | 0 | 5 | 11 | 3B | C6 | 1 | CC | 0 | 5A | F |
| 5FF0 | 0 | F4 | 1 | 56 | 2 | 9B | 1 | D6 | 0 | A | 17 | 0 | 7 | 11 | 3B | C6 |

| Addr | | | | | | | | | | | | | | |
|------|---|---|---|---|---|---|---|---|---|---|---|---|---|---|
| 6000 | 1 | CC | 0 | 45 | F | 0 | 77 | 1 | 56 | 2 | 9B | 1 | D6 | 0 | A | 17 |
| 6010 | 0 | 9 | 11 | 3B | C6 | 1 | CC | 0 | 30 | F | 0 | FA | 0 | 56 | 2 | 9B |
| 6020 | 1 | D6 | 0 | A | 17 | 0 | B | 11 | 3B | C6 | 1 | CC | 0 | 1B | 17 | 0 |
| 6030 | 7D | 56 | 2 | 9B | 1 | D6 | 0 | A | 17 | 0 | D | 11 | 3B | C6 | 1 | CC |
| 6040 | 0 | 7 | 17 | 0 | F | 11 | 3B | C6 | 1 | 38 | 2 | 48 | 5E | 4D | 0 | 8 |
| 6050 | 50 | 58 | 46 | BD | 5D | 3A | 0 | B9 | 2 | 43 | 3B | C6 | 1 | 43 | 3B | B7 |
| 6060 | 1 | AA | 2 | 5E | 5F | 43 | 3B | B7 | 1 | 8B | 3 | C5 | 42 | 43 | 3B | B7 |
| 6070 | 1 | 2F | 3A | B7 | 1 | C5 | 42 | 39 | 3A | B7 | 1 | 2F | 3A | B7 | 1 | 99 |
| 6080 | 2 | D8 | 2 | 8B | 3 | E2 | 0 | 43 | 3B | B7 | 1 | 2F | 3A | B7 | 1 | 79 |
| 6090 | 2 | E8 | 2 | 83 | 2 | CF | 44 | B7 | 1 | AF | 5F | 35 | 4 | 79 | 2 | 88 |
| 60A0 | 2 | 7B | 5E | 46 | 2 | 79 | 2 | 88 | 2 | C6 | 1 | 17 | 0 | 2 | 7 | 1 |
| 60B0 | D6 | 48 | 4 | 43 | 3B | B7 | 1 | 8B | 3 | C5 | 42 | 43 | 3B | B7 | 1 | 2F |
| 60C0 | 3A | B7 | 1 | C5 | 42 | 39 | 3A | B7 | 1 | 2F | 3A | B7 | 1 | 99 | 2 | D8 |
| 60D0 | 2 | 74 | E | 4D | 0 | 4 | 4C | 53 | 55 | 4D | 5C | 99 | 0 | 45 | 20 | 4 |
| 60E0 | 4C | 43 | 4E | D5 | 60 | 99 | 0 | 45 | 20 | 4 | 4C | 4D | 41 | DF | 60 | 99 |
| 60F0 | 0 | 45 | 20 | 5 | 54 | 52 | 55 | A9 | 5F | 99 | 0 | F0 | 0 | 7 | 41 | 56 |
| 6100 | 4D | CF | 5E | 3A | 0 | 8B | 3 | EF | 60 | C6 | 1 | 8B | 3 | DB | 60 | C6 |
| 6110 | 1 | 8B | 3 | E5 | 60 | C6 | 1 | 56 | 2 | 88 | 2 | 46 | 2 | E2 | 0 | 79 |
| 6120 | 2 | 29 | 3C | E5 | 1 | F9 | 60 | B7 | 1 | 9B | 1 | D6 | 0 | 38 | 79 | 2 |
| 6130 | 29 | 3C | E5 | 1 | EF | 60 | B7 | 1 | 35 | 4 | 77 | 1 | D6 | 0 | C | 79 |
| 6140 | 2 | DB | 60 | D5 | 1 | 95 | 3 | E5 | 60 | D5 | 1 | A9 | 1 | D6 | 0 | 16 |
| 6150 | 79 | 2 | 29 | 3C | E5 | 1 | EF | 60 | F7 | 1 | 79 | 2 | DB | 60 | C6 | 1 |
| 6160 | 95 | 3 | E5 | 60 | C6 | 1 | F1 | 0 | B6 | 4D | 0 | 5 | 4C | 43 | 41 | E9 |
| 6170 | 60 | 3A | 0 | 53 | 5C | 3 | 61 | DB | 60 | B7 | 1 | E5 | 60 | B7 | 1 | A9 |
| 6180 | 22 | 4D | 0 | 7 | 4C | 55 | 4D | 6B | 61 | 3A | 0 | 39 | 3A | B7 | 1 | 2F |
| 6190 | 3A | B7 | 1 | E2 | 0 | 35 | 4 | 79 | 2 | 71 | 61 | 79 | 2 | 31 | 3D | F7 |
| 61A0 | 1 | F1 | 0 | F1 | 48 | 4 | 4D | 0 | 5 | 50 | 50 | 4C | 4F | 60 | 3A | 0 |
| 61B0 | B9 | 2 | 43 | 3B | C6 | 1 | 39 | 3A | B7 | 1 | 2F | 3A | B7 | 1 | E2 | 0 |
| 61C0 | 43 | 3B | B7 | 1 | 79 | 2 | C5 | 42 | B7 | 1 | B7 | 39 | B7 | 1 | 88 | 2 |
| 61D0 | C1 | 4C | 79 | 2 | D2 | 4C | AD | 39 | B7 | 1 | F7 | 4C | F1 | 0 | E1 | 4D |
| 61E0 | 0 | 9 | 46 | 49 | 4E | 58 | 5F | 3A | 0 | 17 | 0 | 20 | 17 | 0 | 40 | 89 |
| 61F0 | 61 | 8B | 3 | 31 | 3D | 2F | 3A | B7 | 1 | 88 | 2 | 39 | 3A | B7 | 1 | 2F |
| 6200 | 3A | B7 | 1 | 99 | 2 | 54 | 35 | 11 | 3A | C6 | 1 | F | 0 | A0 | 0 | 17 |
| 6210 | 0 | 40 | 89 | 61 | 8B | 3 | 31 | 3D | 2F | 3A | B7 | 1 | 88 | 2 | 39 | 3A |
| 6220 | B7 | 1 | 2F | 3A | B7 | 1 | 99 | 2 | 54 | 35 | 1B | 3A | C6 | 1 | 4D | 0 |
| 6230 | 8 | 49 | 57 | 49 | 8 | 5E | 3A | 0 | 8B | 3 | 29 | 3C | 11 | 3A | B7 | 1 |
| 6240 | 88 | 2 | 43 | 3A | B7 | 1 | E8 | 2 | 99 | 2 | A7 | 3A | C6 | 1 | 8B | 3 |
| 6250 | 29 | 3C | 1B | 3A | B7 | 1 | 88 | 2 | 43 | 3A | B7 | 1 | 4D | 3A | B7 | 1 |
| 6260 | 88 | 2 | E8 | 2 | 99 | 2 | B1 | 3A | C6 | 1 | 43 | 3A | B7 | 1 | 28 | 2 |
| 6270 | F8 | 2 | 57 | 3A | C6 | 1 | 4D | 0 | A | 4E | 4F | 52 | CC | 5C | 3A | 0 |
| 6280 | 8B | 3 | 25 | 3B | C6 | 1 | 11 | 3B | B7 | 1 | E8 | 2 | D8 | 2 | 1B | 3B |
| 6290 | C6 | 1 | 8B | 3 | 25 | 3B | C6 | 1 | 11 | 3B | B7 | 1 | 8B | 3 | E2 | 0 |
| 62A0 | 79 | 2 | 29 | 5C | 28 | 2 | 25 | 3B | D5 | 1 | 79 | 2 | 93 | 40 | C6 | 1 |
| 62B0 | F1 | 0 | ED | 4D | 0 | 4 | 43 | 50 | 52 | F3 | 60 | 3A | 0 | 17 | 0 | 11 |
| 62C0 | 11 | 3B | C6 | 1 | 7E | 62 | 4D | 3A | B7 | 1 | 1B | 3B | B7 | 1 | 99 | 2 |
| 62D0 | 39 | 3B | C6 | 1 | B9 | 2 | 28 | 2 | 28 | 2 | 43 | 3B | C6 | 1 | 8B | 3 |
| 62E0 | C5 | 42 | F | 0 | 0 | 2 | 9F | 3 | 8B | 3 | CF | 44 | F | 0 | 0 | 2 |
| 62F0 | 9F | 3 | 2F | 3A | B7 | 1 | D5 | 5E | 75 | 3A | C6 | 1 | 38 | 2 | 39 | 3A |
| 6300 | B7 | 1 | 2F | 3A | B7 | 1 | E2 | 0 | 79 | 2 | D5 | 5E | 46 | 2 | 43 | 3B |
| 6310 | B7 | 1 | 79 | 2 | CF | 44 | C6 | 1 | 28 | 2 | 43 | 3B | B7 | 1 | 79 | 2 |
| 6320 | C5 | 42 | C6 | 1 | C1 | 4C | 79 | 2 | D2 | 4C | E3 | 4C | AD | 39 | B7 | 1 |
| 6330 | F7 | 4C | F1 | 0 | D3 | 2F | 3A | B7 | 1 | 39 | 3A | B7 | 1 | B9 | 2 | E2 |
| 6340 | 0 | 43 | 3B | B7 | 1 | 79 | 2 | C5 | 42 | B7 | 1 | C1 | 4C | 79 | 2 | D2 |
| 6350 | 4C | F7 | 4C | 17 | 0 | FF | 7 | 1 | E8 | 43 | 3B | B7 | 1 | 8B | 3 | C5 |
| 6360 | 42 | 8B | 3 | BD | 40 | F | 0 | 0 | 2 | 1D | 3 | 43 | 3B | B7 | 1 | AA |
| 6370 | 2 | 55 | 60 | 43 | 3B | B7 | 1 | AA | 2 | AE | 61 | 8B | 3 | BD | 40 | 43 |
| 6380 | 3B | B7 | 1 | 8B | 3 | C5 | 42 | F | 0 | 0 | 2 | 1D | 3 | 4D | 0 | 4 |
| 6390 | 58 | 52 | 45 | 62 | 5D | 66 | 0 | 99 | 0 | 4 | 59 | 52 | 45 | 30 | 62 | 66 |

| | 65 | | | | | | | 66 | | | | | | |
|---|---|---|---|---|---|---|---|---|---|---|---|---|---|---|
| 63A0 | 0 | 20 | 0 | 4 | 46 | 52 | 4F | E1 | 61 | 66 | 0 | 38 | 0 | 4 | 4C | 52 |
| 63B0 | 4F | 83 | 61 | 66 | 0 | 90 | 0 | 4 | 46 | 43 | 4F | A3 | 63 | 66 | 0 | 90 |
| 63C0 | 0 | 4 | 4C | 43 | 4F | AD | 63 | 66 | 0 | D8 | 0 | 4 | 4B | 52 | 45 | C1 |
| 63D0 | 63 | 99 | 0 | FF | 0 | 4 | 35 | 42 | 49 | B7 | 63 | 3A | 0 | 17 | 0 | FF |
| 63E0 | 8B | 3 | E2 | 0 | 79 | 2 | 17 | 39 | C6 | 1 | E3 | 4C | 28 | 2 | F | 0 |
| 63F0 | F7 | 0 | A9 | 1 | D6 | 0 | 5 | 38 | 2 | CC | 0 | 15 | 28 | 2 | 17 | 0 |

LISTING NO. 2

Sheet 18

| 6400 | 4 | 2E | 1 | D8 | 2 | 46 | 2 | F | 0 | F8 | 0 | 2E | 1 | 88 | 2 | F7 |
|---|---|---|---|---|---|---|---|---|---|---|---|---|---|---|---|---|
| 6410 | 4C | F1 | 0 | D0 | 4D | 0 | 7 | 52 | 45 | 47 | FD | 60 | 3A | 0 | F | 0 |
| 6420 | 0 | 4 | 8B | 3 | E2 | 0 | 79 | 2 | F | 0 | E0 | 3 | 2E | 1 | 79 | 2 |
| 6430 | 17 | 0 | 1F | 2E | 1 | 17 | 0 | 20 | F8 | 2 | 99 | 2 | 17 | 0 | 8 | A9 |
| 6440 | 22 | F | 0 | 80 | 0 | 88 | 2 | 28 | 2 | 28 | 2 | 79 | 2 | 8B | 3 | 41 |
| 6450 | 4D | F1 | 0 | D2 | 4D | 0 | B | 4C | 49 | 4E | CB | 63 | 3A | 0 | 71 | 39 |
| 6460 | B7 | 1 | 99 | 2 | A3 | 39 | B7 | 1 | 85 | 39 | B7 | 1 | 95 | 22 | 8F | 39 |
| 6470 | B7 | 1 | 88 | 2 | 4D | 0 | 8 | 50 | 4C | 4F | A8 | 61 | 3A | 0 | 35 | 4 |
| 6480 | 8F | 39 | C6 | 1 | 99 | 39 | C6 | 1 | 99 | 2 | A3 | 39 | C6 | 1 | 8B | 3 |
| 6490 | BD | 40 | D5 | 36 | 35 | 4 | 13 | 36 | 71 | 39 | C6 | 1 | 3B | 36 | 7B | 39 |
| 64A0 | C6 | 1 | 7B | 39 | B7 | 1 | 71 | 39 | B7 | 1 | 99 | 2 | 85 | 39 | C6 | 1 |
| 64B0 | D5 | 36 | 8B | 3 | E2 | 0 | F | 0 | FF | 0 | 79 | 2 | BD | 40 | B7 | 1 |
| 64C0 | 5C | 64 | B7 | 39 | B7 | 1 | 88 | 2 | B7 | 39 | B7 | 1 | 79 | 2 | E8 | 2 |
| 64D0 | 17 | 0 | 40 | 88 | 2 | B | 4D | 17 | 0 | 2 | 7 | 1 | D9 | 4D | 0 | 9 |
| 64E0 | 28 | 45 | 4E | 8F | 63 | 3A | 0 | 35 | 4 | 71 | 39 | C6 | 1 | 7B | 39 | C6 |
| 64F0 | 1 | 99 | 2 | 85 | 39 | C6 | 1 | 35 | 4 | 8F | 39 | C6 | 1 | 99 | 39 | C6 |
| 6500 | 1 | 99 | 2 | A3 | 39 | C6 | 1 | 17 | 0 | FF | 8B | 3 | E2 | 0 | 79 | 2 |
| 6510 | 17 | 39 | C6 | 1 | E3 | 4C | 71 | 39 | B7 | 1 | 56 | 2 | A9 | 1 | 46 | 2 |
| 6520 | 7B | 39 | B7 | 1 | 56 | 2 | 9B | 1 | 67 | 2 | 8B | 3 | A9 | 1 | D6 | 0 |
| 6530 | 9 | 48 | 4 | 8F | 39 | B7 | 1 | CC | 0 | 12 | 8B | 3 | A9 | 1 | D6 | 0 |
| 6540 | 9 | 38 | 2 | 99 | 39 | B7 | 1 | CC | 0 | 2 | 5C | 64 | F7 | 4C | 95 | 3 |
| 6550 | 20 | 1 | BB | 4D | 0 | 4 | 56 | 4D | 49 | D5 | 63 | 99 | 0 | 45 | 20 | 4 |
| 6560 | 56 | 4D | 41 | 55 | 65 | 99 | 0 | 45 | 20 | 6 | 56 | 52 | 41 | 5F | 65 | 99 |
| 6570 | 0 | 20 | 20 | 7 | 56 | 4D | 49 | 69 | 65 | 3A | 0 | F | 0 | FF | 7F | 5B |
| 6580 | 65 | C6 | 1 | 8B | 3 | 65 | 65 | C6 | 1 | B3 | 63 | A9 | 63 | E2 | 0 | C7 |
| 6590 | 63 | BD | 63 | E2 | 0 | 79 | 2 | C1 | 4C | F1 | 3 | D2 | 4C | E3 | 4C | 28 |
| 65A0 | 2 | 5B | 65 | B7 | 1 | 69 | 3 | 5B | 65 | C6 | 1 | 65 | 65 | B7 | 1 | 7D |
| 65B0 | 3 | 65 | 65 | C6 | 1 | F1 | 0 | DD | F1 | 0 | D4 | 65 | 65 | B7 | 1 | 5B |
| 65C0 | 65 | B7 | 1 | 99 | 2 | 6F | 65 | C6 | 1 | 4D | 0 | 7 | 45 | 4E | 48 | 73 |
| 65D0 | 65 | 3A | 0 | 79 | 65 | F | 0 | FF | 0 | 8B | 3 | 65 | 65 | B7 | 1 | 5B |
| 65E0 | 65 | B7 | 1 | E5 | 64 | 4D | 0 | 4 | 46 | 4C | 49 | CB | 65 | EF | 65 | 1E |
| 65F0 | 53 | 8E | 1E | B5 | 38 | B9 | 0 | 4 | BA | E0 | 3 | BB | 0 | 8 | 8B | F9 |
| 6600 | 8B | C1 | 23 | C2 | D1 | E8 | D1 | E8 | 88 | 5 | 3 | FB | 88 | 5 | 3 | FB |
| 6610 | 88 | 5 | 3 | FB | E2 | E8 | 5B | 1F | AD | 97 | FF | 25 | 4 | 46 | 4C | 4F |
| 6620 | E7 | 65 | 24 | 66 | 1E | 53 | 8E | 1E | B5 | 38 | B9 | 0 | 4 | BA | 1F | 0 |
| 6630 | BB | 0 | 8 | 8B | F9 | 8B | C1 | 23 | C2 | D1 | E0 | D1 | E0 | D1 | E0 | 88 |
| 6640 | 5 | 3 | FB | 88 | 5 | 3 | FB | 88 | 5 | 3 | FB | E2 | E6 | 5B | 1F | AD |
| 6650 | 97 | FF | 25 | 8 | 49 | 4E | 4E | 99 | 63 | 3A | 0 | EB | 18 | B7 | 1 | 17 |
| 6660 | 0 | 16 | 88 | 2 | B7 | 1 | B6 | 24 | 17 | 0 | 16 | 56 | 2 | 77 | 1 | D6 |
| 6670 | 0 | 12 | 17 | 0 | B | AA | 20 | 67 | 39 | B7 | 1 | B9 | 2 | DA | 48 | 8B |
| 6680 | 3 | CC | 0 | 56 | 17 | 0 | B | 56 | 2 | 77 | 1 | D6 | 0 | 12 | 17 | 0 |
| 6690 | 16 | AA | 20 | 67 | 39 | B7 | 1 | AA | 2 | DA | 48 | 8B | 3 | CC | 0 | 3A |
| 66A0 | 17 | 0 | 8 | 56 | 2 | 77 | 1 | D6 | 0 | 12 | 17 | 0 | C | AA | 20 | 5D |
| 66B0 | 39 | B7 | 1 | AA | 2 | C5 | 48 | 8B | 3 | CC | 0 | 1E | 17 | 0 | C | 56 |
| 66C0 | 2 | 77 | 1 | D6 | 0 | 12 | 17 | 0 | 8 | AA | 20 | 5D | 39 | B7 | 1 | B9 |
| 66D0 | 2 | C5 | 48 | 8B | 3 | CC | 0 | 2 | 95 | 3 | 46 | 2 | 38 | 2 | 4D | 0 |
| 66E0 | 6 | 50 | 52 | 45 | 76 | 64 | 3A | 0 | 95 | 3 | 46 | 2 | 86 | 4B | 8B | 3 |
| 66F0 | 46 | 2 | 86 | 4B | F | 0 | 0 | 1 | F9 | 38 | C6 | 1 | 8B | 3 | C5 | 48 |
| 6700 | 8B | 3 | DA | 48 | 4D | 0 | 8 | 52 | 45 | 47 | 16 | 64 | 3A | 0 | 3 | 30 |

| | | | | | | | | | | | | | | | |
|---|---|---|---|---|---|---|---|---|---|---|---|---|---|---|---|
| 6710 | E6 | 66 | 2F | 37 | 81 | 49 | E4 | 5 | E4 | 5 | 17 | 0 | B | AA | 20 | F |
| 6720 | 0 | 0 | 1 | F9 | 38 | C6 | 1 | 17 | 0 | 10 | A | 32 | ED | 65 | F9 | 38 |
| 6730 | B7 | 1 | D9 | 30 | 22 | 66 | F9 | 38 | B7 | 1 | D9 | 30 | 6D | 32 | D6 | 0 |
| 6740 | 5 | 59 | 66 | CC | 0 | 2 | 8B | 3 | D6 | 0 | E1 | 17 | 0 | 10 | 1F | 32 |
| 6750 | 4D | 37 | 81 | 49 | 8B | 3 | 6A | 4D | 4D | 0 | 9 | 52 | 45 | 46 | 6 | 67 |
| 6760 | 3A | 0 | 17 | 0 | 0 | 9F | 63 | 17 | 0 | 2 | 88 | 2 | 9F | 63 | B9 | 2 |
| 6770 | E2 | 0 | 95 | 63 | 17 | 0 | 2 | 88 | 2 | 95 | 63 | B9 | 2 | E2 | 0 | 79 |
| 6780 | 2 | C1 | 4C | F1 | 3 | D2 | 4C | E3 | 4C | 88 | 2 | F1 | 0 | F1 | F1 | 0 |
| 6790 | E1 | 17 | 0 | 9 | A9 | 22 | 4D | 0 | 5 | 4B | 52 | 45 | 56 | 64 | 3A | 0 |
| 67A0 | 3 | 30 | E0 | 4A | 60 | 67 | 46 | 2 | E0 | 4A | 60 | 67 | F | 0 | FF | 0 |
| 67B0 | 46 | 2 | 95 | 22 | D1 | 63 | C6 | 1 | 4D | 0 | 4 | 50 | 41 | 4C | E0 | 66 |
| 67C0 | 3A | 0 | 56 | 2 | 88 | 2 | 46 | 2 | E2 | 0 | D1 | 63 | B7 | 1 | E3 | 4C |
| 67D0 | 79 | 2 | E5 | 1 | 95 | 22 | 28 | 2 | F | 0 | FF | 0 | A9 | 1 | D6 | 0 |
| 67E0 | 6 | 38 | 2 | F | 0 | FF | 0 | F7 | 4C | 95 | 3 | 17 | 39 | D5 | 1 | F1 |
| 67F0 | 0 | D8 | 4D | 0 | 5 | 52 | 41 | 54 | 5A | 67 | 3A | 0 | 3 | 30 | 35 | 4 |

LISTING NO. 2

Sheet 19

| | | | | | | | | | | | | | | | |
|---|---|---|---|---|---|---|---|---|---|---|---|---|---|---|---|
| 6800 | 9E | 67 | 46 | 2 | E0 | 4A | 9F | 4A | 67 | 39 | B7 | 1 | 85 | 1 | D6 | 0 |
| 6810 | 1B | 67 | 39 | B7 | 1 | 3F | 3 | F | 0 | 0 | 1 | F8 | 2 | 5D | 39 | B7 |
| 6820 | 1 | 99 | 2 | 17 | 39 | C6 | 1 | 8B | 3 | CC | 0 | 18 | 8B | 3 | 17 | 39 |
| 6830 | C6 | 1 | 67 | 39 | B7 | 1 | 3F | 3 | F | 0 | 0 | 1 | F8 | 2 | 5D | 39 |
| 6840 | B7 | 1 | 88 | 2 | 46 | 2 | 67 | 39 | B7 | 1 | 17 | 0 | 20 | A9 | 22 | 28 |
| 6850 | 2 | 85 | 1 | D6 | 0 | 7 | 38 | 2 | 8B | 3 | CC | 0 | 2 | 4F | 3 | 35 |
| 6860 | 4 | 88 | 2 | 60 | 2D | 73 | 4A | 67 | 2 | 28 | 2 | 6 | 2 | 4 | 6 | 56 |
| 6870 | 2 | 88 | 2 | F | 0 | 0 | 20 | 67 | 2 | 99 | 2 | C0 | 67 | 17 | 2 | 67 |
| 6880 | 2 | 67 | 2 | 56 | 2 | 17 | 0 | 8 | 88 | 2 | 67 | 2 | 67 | 2 | 88 | 2 |
| 6890 | AA | 2 | E2 | 0 | 79 | 2 | 60 | 2D | 73 | 4A | 4 | 6 | F | 0 | 0 | 20 |
| 68A0 | C0 | 67 | F1 | 0 | EF | 38 | 2 | 4D | 0 | 6 | 48 | 52 | 41 | DF | 64 | 3A |
| 68B0 | 0 | D2 | 4C | 8B | 3 | 67 | 2 | 67 | 2 | E2 | 0 | 79 | 2 | C1 | 4C | 28 |
| 68C0 | 2 | F7 | 4C | 17 | 0 | 2 | 88 | 2 | F1 | 0 | F0 | 38 | 2 | 4D | 0 | 6 |
| 68D0 | 4C | 45 | 47 | 98 | 67 | 3A | 0 | F | 0 | FC | 0 | F | 0 | F4 | 0 | E2 |
| 68E0 | 0 | 17 | 0 | 0 | 17 | 0 | 40 | 8B | 3 | 79 | 2 | B | 4D | 17 | 0 | 0 |
| 68F0 | F | 0 | 0 | 1 | F | 0 | C0 | 0 | 79 | 2 | B | 4D | F | 0 | C0 | 0 |
| 6900 | 17 | 0 | 40 | 79 | 2 | AF | 68 | F1 | 0 | D7 | 17 | 0 | 10 | 17 | 0 | 8 |
| 6910 | E2 | 0 | 8B | 3 | F | 0 | FF | 0 | 8B | 3 | 79 | 2 | B | 4D | F1 | 0 |
| 6920 | F1 | 8B | 3 | F | 0 | 0 | 1 | 8B | 3 | F | 0 | F3 | 0 | B | 4D | 4D |
| 6930 | 0 | 7 | 52 | 41 | 49 | F4 | 67 | C3 | 34 | 3 | 0 | FF | 40 | 0 | FF | 80 |
| 6940 | 0 | FF | FF | 0 | 0 | FF | 0 | 0 | FF | FF | 0 | 80 | FF | 0 | 0 | FF |
| 6950 | FF | 0 | FF | 8 | 52 | 41 | 49 | 31 | 69 | 3A | 0 | 8B | 3 | 37 | 69 | 28 |
| 6960 | 2 | AA | 2 | 28 | 2 | AA | 2 | 67 | 2 | E5 | 1 | 67 | 2 | E5 | 1 | 67 |
| 6970 | 2 | E5 | 1 | 4D | 0 | 6 | 42 | 45 | 59 | 53 | 69 | 3A | 0 | 17 | 0 | 0 |
| 6980 | 17 | 0 | 0 | F | 0 | C0 | 0 | ED | 3B | C6 | 1 | 1 | 3C | C6 | 1 | F7 |
| 6990 | 3B | C6 | 1 | D9 | 3B | B7 | 1 | 95 | 3 | B | 3C | B7 | 1 | 8E | 4D | F |
| 69A0 | 0 | FF | 0 | 28 | 2 | 28 | 2 | ED | 3B | C6 | 1 | F7 | 3B | C6 | 1 | 1 |
| 69B0 | 3C | C6 | 1 | D9 | 3B | B7 | 1 | 15 | 3C | B7 | 1 | F | 0 | 0 | 1 | 56 |
| 69C0 | 2 | 99 | 2 | 8E | 4D | 4D | 0 | 6 | 53 | 57 | 49 | B5 | 62 | 3A | 0 | D9 |
| 69D0 | 3B | B7 | 1 | 61 | 1 | D6 | 0 | D | 8B | 3 | B4 | 49 | 95 | 3 | D9 | 3B |
| 69E0 | C6 | 1 | CC | 0 | A | 95 | 3 | B4 | 49 | 8B | 3 | D9 | 3B | C6 | 1 | 4D |
| 69F0 | 0 | A | 43 | 52 | 41 | C7 | 69 | F9 | 69 | 8B | 6 | 21 | 3C | 59 | F7 | E9 |
| 6A00 | 8B | E | D1 | 3B | F7 | F9 | 3 | 6 | D | 3C | 8B | E | E5 | 3B | 89 | 6 |
| 6A10 | E5 | 3B | 2B | C1 | FF | 36 | DB | 3B | 51 | 50 | AD | 97 | FF | 25 | 6 | 52 |
| 6A20 | 47 | 42 | 75 | 69 | 26 | 6A | 8F | 6 | 3 | 3C | 8F | 6 | F9 | 3B | 8F | 6 |
| 6A30 | EF | 3B | AD | 97 | FF | 25 | 7 | 53 | 50 | 45 | F1 | 69 | 3A | 0 | B | 3C |
| 6A40 | B7 | 1 | 15 | 3C | B7 | 1 | 56 | 2 | 99 | 2 | 1F | 3C | C6 | 1 | E3 | 3B |
| 6A50 | C6 | 1 | CF | 3B | B7 | 1 | AA | 2 | 95 | 3 | E2 | 0 | 79 | 2 | B9 | 2 |
| 6A60 | 59 | 69 | 24 | 6A | 79 | 2 | F7 | 69 | 8E | 4D | F1 | 0 | EF | 4D | 0 | 4 |
| 6A70 | 4C | 54 | 41 | CF | 68 | 3A | 0 | B | 3C | B7 | 1 | 88 | 2 | 95 | 3 | 56 |
| 6A80 | 2 | A9 | 1 | D6 | 0 | 7 | 38 | 2 | 95 | 3 | CC | 0 | 1E | 15 | 3C | B7 |
| 6A90 | 1 | 17 | 0 | 8 | 99 | 2 | 56 | 2 | 9B | 1 | D6 | 0 | E | 38 | 2 | 15 |

| | | | | | | | | | | | | | | | |
|---|---|---|---|---|---|---|---|---|---|---|---|---|---|---|---|
| 6AA0 | 3C | B7 | 1 | 17 | 0 | 8 | 99 | 2 | CC | 0 | 0 | B | 3C | C6 | 1 | 4D |
| 6AB0 | 0 | 4 | 52 | 54 | 41 | 1E | 6A | 3A | 0 | 15 | 3C | B7 | 1 | 88 | 2 | F |
| 6AC0 | 0 | FF | 0 | 56 | 2 | 9B | 1 | D6 | 0 | 9 | 38 | 2 | F | 0 | FF | 0 |
| 6AD0 | CC | 0 | 1E | B | 3C | B7 | 1 | 17 | 0 | 8 | 88 | 2 | 56 | 2 | A9 | 1 |
| 6AE0 | D6 | 0 | E | 38 | 2 | B | 3C | B7 | 1 | 17 | 0 | 8 | 88 | 2 | CC | 0 |
| 6AF0 | 0 | 15 | 3C | C6 | 1 | 4D | 0 | 4 | 54 | 41 | 42 | 36 | 6A | 3A | 0 | 28 |
| 6B00 | 2 | 15 | 3C | D5 | 1 | B | 3C | D5 | 1 | B | 3C | B7 | 1 | 95 | 3 | 9B |
| 6B10 | 1 | D6 | 0 | 13 | 95 | 3 | B | 3C | C6 | 1 | 1F | 3C | B7 | 1 | AA | 2 |
| 6B20 | 15 | 3C | C6 | 1 | CC | 0 | 24 | 15 | 3C | B7 | 1 | F | 0 | FF | 0 | A9 |
| 6B30 | 1 | D6 | 0 | 17 | F | 0 | FF | 0 | 28 | 2 | 15 | 3C | C6 | 1 | 1F | 3C |
| 6B40 | B7 | 1 | 99 | 2 | B | 3C | C6 | 1 | CC | 0 | 0 | 4D | 0 | 2 | 2D | 4C |
| 6B50 | 20 | 78 | 62 | 3A | 0 | 17 | 0 | FF | 75 | 6A | 8B | 3 | 4D | 0 | 2 | 2B |
| 6B60 | 4C | 20 | 6F | 6A | 3A | 0 | 95 | 3 | 75 | 6A | 8B | 3 | 4D | 0 | 2 | 2D |
| 6B70 | 52 | 20 | 4D | 6B | 3A | 0 | 17 | 0 | FF | B7 | 6A | 8B | 3 | 4D | 0 | 2 |
| 6B80 | 2B | 52 | 20 | 5E | 6B | 3A | 0 | 95 | 3 | B7 | 6A | 8B | 3 | 4D | 0 | 2 |
| 6B90 | 2D | 54 | 20 | 6E | 6B | 3A | 0 | 17 | 0 | FF | FD | 6A | 8B | 3 | 4D | 0 |
| 6BA0 | 2 | 2B | 54 | 20 | 7F | 6B | 3A | 0 | 95 | 3 | FD | 6A | 8B | 3 | 4D | 0 |
| 6BB0 | A | 50 | 41 | 4C | BA | 67 | 3A | 0 | 42 | 49 | 8B | 3 | 6A | 4D | 95 | 3 |
| 6BC0 | 6A | 4D | 95 | 3 | D9 | 3B | C6 | 1 | D5 | 68 | 8E | 20 | 17 | 0 | 16 | 56 |
| 6BD0 | 2 | 77 | 1 | D6 | 0 | 5 | 53 | 6B | CC | 0 | 4D | 17 | 0 | B | 56 | 2 |
| 6BE0 | 77 | 1 | D6 | 0 | 5 | 64 | 6B | CC | 0 | 3E | 17 | 0 | 8 | 56 | 2 | 77 |
| 6BF0 | 1 | D6 | 0 | 5 | 74 | 6B | CC | 0 | 2F | 17 | 0 | C | 56 | 2 | 77 | 1 |

LISTING NO. 2

Sheet 20

| | | | | | | | | | | | | | | | |
|---|---|---|---|---|---|---|---|---|---|---|---|---|---|---|---|
| 6C00 | D6 | 0 | 5 | 85 | 6B | CC | 0 | 20 | 17 | 0 | 2C | 56 | 2 | 77 | 1 | D6 |
| 6C10 | 0 | 5 | 95 | 6B | CC | 0 | 11 | 17 | 0 | 2E | 56 | 2 | 77 | 1 | D6 | 0 |
| 6C20 | 5 | A6 | 6B | CC | 0 | 2 | 95 | 3 | 46 | 2 | 38 | 2 | 7B | 69 | 3C | 6A |
| 6C30 | CD | 69 | D6 | 0 | 95 | 4D | 0 | 3 | 42 | 26 | 57 | B1 | 6A | 3A | 0 | 8B |
| 6C40 | 3 | 6A | 4D | 95 | 3 | 6A | 4D | 8B | 3 | B4 | 49 | 4D | 0 | 2 | 54 | 54 |
| 6C50 | 20 | F7 | 6A | 3A | 0 | E2 | 0 | 79 | 2 | F | 0 | 0 | 4 | 87 | 7 | E4 |
| 6C60 | 5 | E4 | 5 | F | 0 | 0 | 4 | 7 | 1 | ED | 4D | 0 | 0 | 20 | 20 | 20 |
| 6C70 | 4E | 54 | 20 | 20 | 20 | 9 | 6C | 56 | 2 | 17 | 0 | 20 | 77 | 1 | D6 | 0 |
| 6C80 | 6 | 17 | 0 | A | CC | 0 | 3 | 17 | 46 | 36 | 43 | 36 | 43 | 6C | 4D | 0 |
| 6C90 | 5 | 53 | 45 | 4E | 40 | 6C | 3A | 0 | 3D | 5 | C8 | 2 | E5 | 1 | 6 | 2 |
| 6CA0 | 1B | 6C | 8B | 3 | 28 | 2 | 35 | 4 | 79 | 2 | 17 | 0 | 3 | 73 | 6C | 17 |
| 6CB0 | 2 | 48 | 4 | 4D | 0 | B | 52 | 45 | 43 | DB | 6B | 3A | 0 | 3D | 5 | C8 |
| 6CC0 | 2 | E5 | 1 | 6 | 2 | 1B | 6C | 8B | 3 | 28 | 2 | 35 | 4 | 79 | 2 | 95 |
| 6CD0 | 3 | 73 | 6C | 17 | 2 | 48 | 4 | 4D | 0 | 6 | 2E | 53 | 45 | 9D | 6B | 3A |
| 6CE0 | 0 | 15 | 8 | 16 | 20 | 20 | 20 | 44 | 49 | 53 | 4B | 20 | 45 | 52 | 52 | 4F |
| 6CF0 | 52 | 3A | 20 | 20 | 20 | 54 | 59 | 50 | 45 | 20 | 1B | 6C | 28 | 2 | E5 | 1 |
| 6D00 | 46 | 2 | 56 | 2 | 28 | 2 | 17 | 0 | 30 | 2E | 1 | 17 | 0 | 10 | A9 | 22 |
| 6D10 | 35 | 7 | 15 | 8 | 8 | 20 | 20 | 20 | 43 | 4F | 44 | 45 | 20 | 17 | 0 | F |
| 6D20 | 2E | 1 | 35 | 7 | 15 | 8 | 7 | 20 | 20 | 20 | 4C | 55 | 4E | 20 | AA | 2 |
| 6D30 | 28 | 2 | E5 | 1 | 17 | 0 | 60 | 2E | 1 | 17 | 0 | 20 | A9 | 22 | 35 | 7 |
| 6D40 | 46 | 2 | F | 0 | 80 | 0 | 2E | 1 | 61 | 1 | D6 | 0 | 5 | 38 | 2 | CC |
| 6D50 | 0 | 1A | 15 | 8 | A | 20 | 20 | 20 | 53 | 45 | 43 | 54 | 4F | 52 | 20 | AA |
| 6D60 | 2 | B7 | 1 | A3 | 6B | 53 | 7 | 17 | 0 | 3 | 6C | 6 | 17 | 0 | 3 | 6C |
| 6D70 | 6 | 4D | 0 | 6 | 3F | 45 | 52 | 46 | 6B | 3A | 0 | 3D | 5 | C8 | 2 | E5 |
| 6D80 | 1 | 17 | 0 | 3 | 2E | 1 | 61 | 1 | 61 | 3 | 4D | 0 | 5 | 45 | 52 | 52 |
| 6D90 | 12 | 6B | 3A | 0 | 79 | 6D | D6 | 0 | 54 | 17 | 0 | A | 8B | 3 | E2 | 0 |
| 6DA0 | 9 | 6C | 9 | 6C | 17 | 0 | 5 | 88 | 2 | E2 | 0 | 79 | 2 | E5 | 1 | 17 |
| 6DB0 | 0 | FF | 7 | 1 | F6 | 73 | 6C | 79 | 6D | 61 | 3 | D6 | 0 | 2 | 0 | 4 |
| 6DC0 | F1 | 0 | DD | 79 | 6D | D6 | 0 | 25 | 17 | 0 | 7 | AA | 20 | C3 | 4 | B7 |
| 6DD0 | 1 | F1 | D | F5 | 6B | B7 | 1 | 8B | 3 | F5 | 6B | C6 | 1 | 96 | 6C | E4 |
| 6DE0 | 5 | DF | 6C | BB | 6C | F5 | 6B | C6 | 1 | C3 | 4 | C6 | 1 | 4D | 0 | 7 |
| 6DF0 | 43 | 44 | 42 | 90 | 6C | 3A | 0 | 8B | 3 | 17 | 0 | 4 | 67 | 2 | 28 | 2 |
| 6E00 | 17 | 0 | 4 | F8 | 2 | 28 | 2 | A3 | 6B | 67 | 2 | F | 0 | 67 | 2 | A9 |
| 6E10 | 1 | D6 | 0 | 6 | 17 | 0 | 20 | CC | 0 | 2 | 8B | 3 | FF | 6B | B7 | 1 |

| | | | | | | | | | | | | | | | |
|---|---|---|---|---|---|---|---|---|---|---|---|---|---|---|---|
| 6E20 | 3F | 1 | 4D | 0 | 8 | 5B | 42 | 55 | C1 | 6B | 3A | 0 | 3D | 5 | D | 19 |
| 6E30 | 17 | A | F5 | 6D | 17 | 0 | A | 73 | 6C | 92 | 6D | 3D | 5 | 19 | 19 | 4D |
| 6E40 | 0 | 7 | 5B | 42 | 4C | 24 | 6E | 3A | 0 | B1 | 4 | B7 | 1 | 88 | 2 | 7F |
| 6E50 | 5 | DF | 9 | 8F | A | 3D | 5 | 2E | 19 | 56 | 2 | F5 | 6D | 17 | 0 | 8 |
| 6E60 | 73 | 6C | 92 | 6D | 46 | 2 | 7B | A | 3D | 5 | 19 | 19 | 4D | 0 | 2 | 46 |
| 6E70 | 3A | 20 | 8C | 6D | 3A | 0 | 8B | 3 | FF | 6B | C6 | 1 | 4D | 0 | 2 | 57 |
| 6E80 | 3A | 20 | 6D | 6C | 3A | 0 | 17 | 0 | 20 | FF | 6B | C6 | 1 | 4D | 0 | 3 |
| 6E90 | 53 | 43 | 40 | EF | 6D | 97 | 6E | 8C | DA | 5F | 1F | 2B | C0 | 8A | 5 | 50 |
| 6EA0 | 8E | DA | AD | 97 | FF | 25 | 2 | 53 | 40 | 20 | 8F | 6E | AE | 6E | 8C | DA |
| 6EB0 | 5F | 1F | 8A | 5 | 47 | 8A | 25 | 50 | 8E | DA | AD | 97 | FF | 25 | 3 | 53 |
| 6EC0 | 43 | 21 | A6 | 6E | C6 | 6E | 8C | C2 | 5F | 7 | 58 | AA | 8E | C2 | AD | 97 |
| 6ED0 | FF | 25 | 2 | 53 | 21 | 20 | BE | 6E | DA | 6E | 8C | C2 | 5F | 7 | 58 | AA |
| 6EE0 | 8A | C4 | AA | 8E | C2 | AD | 97 | FF | 25 | 5 | 53 | 4D | 4F | D2 | 6E | F1 |
| 6EF0 | 6E | 59 | 5F | 8C | D8 | 8C | C2 | 89 | 76 | FE | 7 | 5E | 1F | 50 | F3 | A4 |
| 6F00 | 1F | 8E | C2 | 8B | 76 | FE | AD | 97 | FF | 25 | 4 | 50 | 49 | 43 | 73 | 6D |
| 6F10 | 12 | 6F | 8B | FC | 58 | D1 | E0 | 3 | F8 | FF | 35 | AD | 97 | FF | 25 | 4 |
| 6F20 | 52 | 4F | 4C | B5 | 6C | 3A | 0 | 28 | 2 | D8 | 2 | 6 | 2 | 10 | 6F | C0 |
| 6F30 | 3 | 28 | 2 | C8 | 2 | 17 | 2 | 74 | E | 38 | 2 | 4D | 0 | 5 | 35 | 55 |
| 6F40 | 53 | 6E | 6E | 45 | 6F | 59 | 87 | C8 | 87 | C8 | 87 | C8 | 87 | C8 | E2 | F6 |
| 6F50 | AD | 97 | FF | 25 | 4 | 4D | 53 | 45 | D9 | 6C | 3A | 0 | F | 0 | C8 | 0 |
| 6F60 | F8 | 2 | 43 | 6F | 4D | 0 | 4 | 42 | 45 | 4C | 1F | 6F | 3A | 0 | 17 | 0 |
| 6F70 | 7 | AA | 20 | 4D | 0 | 5 | 51 | 55 | 45 | 66 | 6F | 3A | 0 | 60 | 4 | B7 |
| 6F80 | 1 | 17 | 0 | 50 | C7 | 5 | 4D | 0 | 2 | 4E | 3F | 20 | 54 | 6F | 3A | 0 |
| 6F90 | 7B | 6F | 8B | 3 | CC | 4 | C6 | 1 | 17 | 0 | 20 | 75 | 8 | 5C | 9 | 4D |
| 6FA0 | 0 | 4 | 3C | 4E | 3C | 41 | 6E | 3A | 0 | 15 | 8 | 4 | 20 | 20 | 5B | 20 |
| 6FB0 | 95 | 3 | 10 | 6F | 53 | 7 | 15 | 8 | 6 | 3C | 20 | 4E | 20 | 3C | 20 | 17 |
| 6FC0 | 0 | 2 | 10 | 6F | 53 | 7 | 15 | 8 | 3 | 5D | 20 | 20 | 8E | 6F | 17 | 0 |
| 6FD0 | 2 | 10 | 6F | 56 | 2 | 9B | 1 | 61 | 1 | 17 | 0 | 4 | 10 | 6F | 17 | 0 |
| 6FE0 | 3 | 10 | 6F | 9B | 1 | 3F | 1 | 28 | 2 | D6 | 0 | 8 | 46 | 2 | 38 | 2 |
| 6FF0 | 6C | 6F | E4 | 5 | 61 | 1 | D6 | 0 | B0 | 67 | 2 | 67 | 2 | 48 | 4 | 4D |

LISTING NO. 3

Sheet 1

| | | | | | | | | | | | | | | | |
|---|---|---|---|---|---|---|---|---|---|---|---|---|---|---|---|
| 0 | 22 | E | 0 | 0 | 22 | E | 0 | 0 | 22 | E | 0 | 0 | 22 | E | 0 | 0 |
| 10 | 22 | E | 0 | 0 | 22 | E | 0 | 0 | 22 | E | 0 | 0 | 22 | E | 0 | 0 |
| 20 | 22 | E | 0 | 0 | 22 | E | 0 | 0 | 22 | E | 0 | 0 | 22 | E | 0 | 0 |
| 30 | 22 | E | 0 | 0 | 22 | E | 0 | 0 | 22 | E | 0 | 0 | 22 | E | 0 | 0 |
| 40 | A5 | 5A | FF | FF | FF | FF | FF | FF | FF | FF | FF | FF | FF | FF | FF | FF |
| 50 | FF | FF | FF | FF | FF | FF | FF | FF | FF | FF | FF | FF | FF | FF | 0 | 67 |
| 60 | FF | FF | FF | FF | FF | FF | FF | FF | FF | FF | FF | FF | FF | FF | FF | FF |
| 70 | FF | FF | FF | FF | FF | FF | FF | FF | FF | FF | FF | FF | FF | FF | FF | FF |
| 80 | A1 | 40 | 0 | F7 | D0 | A3 | 40 | 0 | B8 | 0 | 0 | 8E | C0 | 8E | D0 | 8E |
| 90 | D8 | BD | FE | F | BC | 7E | F | B8 | 90 | 0 | E6 | 6 | BE | 23 | E | FC |
| A0 | AD | 97 | FF | 25 | FF | FF | FF | FF | FF | FF | FF | FF | FF | FF | FF | FF |
| B0 | FF | FF | FF | FF | FF | FF | FF | FF | FF | FF | FF | FF | FF | FF | FF | FF |
| C0 | FF | FF | FF | FF | FF | FF | FF | FF | FF | FF | FF | FF | FF | FF | FF | FF |
| D0 | FF | FF | FF | FF | FF | FF | FF | FF | FF | FF | FF | FF | FF | FF | FF | FF |
| E0 | FF | FF | FF | FF | FF | FF | FF | FF | FF | FF | FF | FF | FF | FF | FF | FF |
| F0 | FF | FF | FF | FF | FF | FF | FF | FF | FF | FF | FF | FF | FF | FF | FF | FF |
| 100 | 2 | 1 | AD | 50 | AD | 97 | FF | 25 | A | 1 | AC | 98 | 50 | AD | 97 | FF |
| 110 | 25 | 47 | 47 | 4D | 4D | 89 | 76 | 0 | 8B | F7 | AD | 97 | FF | 25 | 20 | 1 |
| 120 | 8B | 76 | 0 | 45 | 45 | AD | 97 | FF | 25 | FF | 75 | 2 | AD | 97 | FF | 25 |
| 130 | 47 | 47 | 57 | AD | 97 | FF | 25 | 4D | 4D | 89 | 76 | 0 | 5E | 47 | 47 | 57 |
| 140 | AD | 97 | FF | 25 | 8A | 45 | 2 | 98 | 3 | C3 | 50 | AD | 97 | FF | 25 | 51 |
| 150 | 1 | AC | 98 | 3 | F0 | AD | 97 | FF | 25 | 5B | 1 | 58 | B | C0 | 74 | F1 |
| 160 | 46 | AD | 97 | FF | 25 | 67 | 1 | 83 | ED | 4 | 8F | 46 | 0 | 8F | 46 | 2 |
| 170 | AD | 97 | FF | 25 | 76 | 1 | 8B | 46 | 0 | 40 | 3B | 46 | 2 | 73 | 1C | 89 |

| | | | | | | | | | | | | | | | | |
|---|---|---|---|---|---|---|---|---|---|---|---|---|---|---|---|---|
| 180 | 46 | 0 | AC | 98 | 3 | F0 | AD | 97 | FF | 25 | 8C | 1 | 58 | 8B | D0 | 3 |
| 190 | 46 | 0 | 8B | F8 | 2B | 7E | 2 | 33 | D7 | 78 | E4 | 83 | C5 | 4 | 46 | AD |
| 1A0 | 97 | FF | 25 | A5 | 1 | 58 | 3 | 46 | 0 | EB | CF | AD | 1 | 5A | 58 | 23 |
| 1B0 | C2 | 50 | AD | 97 | FF | 25 | B8 | 1 | 5A | 58 | B | C2 | 50 | AD | 97 | FF |
| 1C0 | 25 | C3 | 1 | 5A | 58 | 33 | C2 | 50 | AD | 97 | FF | 25 | CE | 1 | 58 | B |
| 1D0 | C0 | B8 | 0 | 0 | 75 | 1 | 40 | 50 | AD | 97 | FF | 25 | DE | 1 | 5A | 58 |
| 1E0 | 3B | C2 | EB | ED | E6 | 1 | 58 | B | C0 | B8 | 0 | 0 | 79 | 1 | 40 | 50 |
| 1F0 | AD | 97 | FF | 25 | F6 | 1 | 5A | 58 | 2B | C2 | EB | ED | FE | 1 | 58 | 5A |
| 200 | 2B | C2 | EB | E5 | 6 | 2 | 5F | FF | 35 | AD | 97 | FF | 25 | F | 2 | 5F |
| 210 | 58 | AB | AD | 97 | FF | 25 | 18 | 2 | 5F | 58 | 1 | 5 | AD | 97 | FF | 25 |
| 220 | 22 | 2 | 5F | 2B | C0 | 8A | 5 | 50 | AD | 97 | FF | 25 | 2E | 2 | 5F | 58 |
| 230 | AA | AD | 97 | FF | 25 | 37 | 2 | 4D | 4D | 8F | 46 | 0 | AD | 97 | FF | 25 |
| 240 | 42 | 2 | FF | 76 | 0 | 45 | 45 | AD | 97 | FF | 25 | 4D | 2 | 8B | FC | FF |
| 250 | 35 | AD | 97 | FF | 25 | 57 | 2 | 44 | 44 | AD | 97 | FF | 25 | 5F | 2 | 5A |
| 260 | 58 | 52 | 50 | AD | 97 | FF | 25 | 69 | 2 | 8B | FC | FF | 75 | 2 | AD | 97 |
| 270 | FF | 25 | 74 | 2 | 5F | 5A | 58 | 52 | 57 | 50 | AD | 97 | FF | 25 | 80 | 2 |
| 280 | FF | 76 | 0 | AD | 97 | FF | 25 | 89 | 2 | 5A | 58 | 3 | C2 | 50 | AD | 97 |
| 290 | FF | 25 | 94 | 2 | 5A | 58 | 2B | C2 | 50 | AD | 97 | FF | 25 | 9F | 2 | 58 |
| 2A0 | 40 | 50 | AD | 97 | FF | 25 | A8 | 2 | 58 | 48 | 50 | AD | 97 | FF | 25 | B1 |
| 2B0 | 2 | 58 | 40 | 40 | 50 | AD | 97 | FF | 25 | BB | 2 | 58 | D1 | E0 | 50 | AD |
| 2C0 | 97 | FF | 25 | C5 | 2 | 58 | D1 | F8 | 50 | AD | 97 | FF | 25 | CF | 2 | 5F |
| 2D0 | 58 | F7 | E7 | 50 | AD | 97 | FF | 25 | DA | 2 | 5F | 58 | 2B | D2 | F7 | F7 |
| 2E0 | 52 | 50 | AD | 97 | FF | 25 | E8 | 2 | 59 | 5F | 58 | E3 | 11 | 96 | D1 | CF |
| 2F0 | D1 | C7 | 73 | 2 | A4 | 49 | D1 | E9 | F3 | A5 | 73 | 1 | A4 | 96 | AD | 97 |
| 300 | FF | 25 | 4 | 3 | 58 | F7 | D8 | 50 | AD | 97 | FF | 25 | E | 3 | 58 | B |
| 310 | C0 | 78 | F2 | 50 | AD | 97 | FF | 25 | 81 | 53 | 1C | 3 | 58 | 5A | 3B | C2 |
| 320 | 79 | 1 | 92 | 52 | AD | 97 | FF | 25 | 2A | 3 | 58 | 5A | 3B | D0 | EB | F0 |
| 330 | 32 | 3 | 5F | 2B | D2 | 58 | F7 | F7 | 52 | AD | 97 | FF | 25 | 3F | 3 | 5F |
| 340 | 5A | 58 | F7 | E2 | F7 | F7 | 52 | 50 | AD | 97 | FF | 25 | 4E | 3 | 5F | 5A |
| 350 | 58 | F7 | EA | F7 | FF | 50 | AD | 97 | FF | 25 | 5C | 3 | 5F | 58 | 99 | F7 |
| 360 | FF | 50 | AD | 97 | FF | 25 | 68 | 3 | 58 | 5A | F7 | EA | 50 | 52 | AD | 97 |
| 370 | FF | 25 | 74 | 3 | 5F | 5A | 58 | F7 | FF | 50 | AD | 97 | FF | 25 | 80 | 3 |
| 380 | 58 | 5A | F7 | E2 | 50 | 52 | AD | 97 | FF | 25 | 8C | 3 | 5F | 5A | 58 | F7 |
| 390 | F7 | 52 | 50 | AD | 97 | FF | 25 | 99 | 3 | 5F | FF | 75 | 2 | FF | 35 | AD |
| 3A0 | 97 | FF | 25 | A5 | 3 | 5F | 58 | AB | 58 | AB | AD | 97 | FF | 25 | B0 | 3 |
| 3B0 | 8B | FC | FF | 75 | 2 | FF | 35 | AD | 97 | FF | 25 | BD | 3 | 83 | C4 | 4 |
| 3C0 | AD | 97 | FF | 25 | 29 | 1 | 0 | 0 | 29 | 1 | 0 | 0 | 29 | 1 | 0 | 10 |
| 3D0 | 29 | 1 | 0 | FF | 29 | 1 | 10 | 0 | 29 | 1 | 10 | 0 | 29 | 1 | 6F | 0 |
| 3E0 | 29 | 1 | 6F | 0 | 29 | 1 | FF | FF | 29 | 1 | FF | FF | 29 | 1 | 0 | 0 |
| 3F0 | 29 | 1 | 0 | 0 | 30 | 1 | FF | FF | 30 | 1 | 0 | 0 | 30 | 1 | 9 | 0 |

LISTING NO. 3

Sheet 2

| | | | | | | | | | | | | | | | | |
|---|---|---|---|---|---|---|---|---|---|---|---|---|---|---|---|---|
| 400 | 30 | 1 | FF | FF | 30 | 1 | FF | FF | 30 | 1 | FF | FF | FF | FF | FF | FF |
| 410 | FF | FF | FF | FF | FF | FF | FF | FF | FF | FF | FF | FF | 30 | 1 | FF | FF |
| 420 | FF | FF | FF | FF | FF | FF | FF | FF | FF | FF | FF | FF | FF | FF | FF | FF |
| 430 | FF | FF | FF | FF | FF | FF | FF | FF | FF | FF | FF | FF | FF | FF | FF | FF |
| 440 | FF | FF | FF | FF | FF | FF | FF | FF | FF | FF | FF | FF | FF | FF | FF | FF |
| 450 | FF | FF | FF | FF | FF | FF | FF | FF | FF | FF | FF | FF | FF | FF | FF | FF |
| 460 | FF | FF | FF | FF | FF | FF | FF | FF | FF | FF | FF | FF | FF | FF | FF | FF |
| 470 | FF | FF | FF | FF | FF | FF | FF | FF | FF | FF | FF | FF | FF | FF | FF | FF |
| 480 | FF | FF | FF | FF | FF | FF | FF | FF | FF | FF | FF | FF | FF | FF | FF | FF |
| 490 | FF | FF | FF | FF | FF | FF | FF | FF | FF | FF | FF | FF | FF | FF | FF | FF |
| 4A0 | FF | FF | FF | FF | FF | FF | FF | FF | FF | FF | FF | FF | FF | FF | FF | FF |
| 4B0 | FF | FF | FF | FF | FF | FF | FF | FF | FF | FF | FF | FF | FF | FF | FF | FF |
| 4C0 | FF | FF | FF | FF | FF | FF | FF | FF | FF | FF | FF | FF | FF | FF | FF | FF |
| 4D0 | FF | FF | FF | FF | FF | FF | FF | FF | FF | FF | FF | FF | FF | FF | FF | FF |
| 4E0 | FF | FF | FF | FF | FF | FF | FF | FF | FF | FF | FF | FF | FF | FF | FF | FF |

| | | | | | | | | | | | | | | | | |
|---|---|---|---|---|---|---|---|---|---|---|---|---|---|---|---|---|
| 4F0 | FF | FF | FF | FF | FF | FF | FF | FF | FF | FF | FF | FF | FF | FF | FF | FF |
| 500 | FF | FF | FF | FF | FF | FF | FF | FF | FF | FF | FF | FF | FF | FF | FF | FF |
| 510 | FF | FF | FF | FF | FF | FF | FF | FF | FF | FF | FF | FF | FF | FF | FF | FF |
| 520 | FF | FF | FF | FF | FF | FF | FF | FF | FF | FF | FF | FF | FF | FF | FF | FF |
| 530 | FF | FF | FF | FF | FF | FF | FF | FF | FF | FF | FF | FF | FF | FF | FF | FF |
| 540 | FF | FF | FF | FF | FF | FF | FF | FF | FF | FF | FF | FF | FF | FF | FF | FF |
| 550 | FF | FF | FF | FF | FF | FF | FF | FF | FF | FF | FF | FF | FF | FF | FF | FF |
| 560 | FF | FF | FF | FF | FF | FF | FF | FF | FF | FF | FF | FF | FF | FF | FF | FF |
| 570 | FF | FF | FF | FF | FF | FF | FF | FF | FF | FF | FF | FF | FF | FF | FF | FF |
| 580 | FF | FF | FF | FF | FF | FF | FF | FF | FF | FF | FF | FF | FF | FF | FF | FF |
| 590 | FF | FF | FF | FF | FF | FF | FF | FF | FF | FF | FF | FF | FF | FF | FF | FF |
| 5A0 | FF | FF | FF | FF | FF | FF | FF | FF | FF | FF | FF | FF | FF | FF | FF | FF |
| 5B0 | FF | FF | FF | FF | FF | FF | FF | FF | FF | FF | FF | FF | FF | FF | FF | FF |
| 5C0 | FF | FF | FF | FF | FF | FF | FF | FF | FF | FF | FF | FF | FF | FF | FF | FF |
| 5D0 | FF | FF | FF | FF | FF | FF | FF | FF | FF | FF | FF | FF | FF | FF | FF | FF |
| 5E0 | FF | FF | FF | FF | FF | FF | FF | FF | FF | FF | FF | FF | FF | FF | FF | FF |
| 5F0 | FF | FF | FF | FF | FF | FF | FF | FF | FF | FF | FF | FF | FF | FF | FF | FF |
| 600 | FF | FF | FF | FF | FF | FF | FF | FF | FF | FF | FF | FF | FF | FF | FF | FF |
| 610 | FF | FF | FF | FF | FF | FF | FF | FF | FF | FF | FF | FF | FF | FF | 29 | 1 |
| 620 | 40 | 0 | 29 | 1 | 40 | 0 | 29 | 1 | 42 | 0 | 29 | 1 | 43 | 0 | 29 | 1 |
| 630 | 44 | 0 | 29 | 1 | 46 | 0 | 29 | 1 | 48 | 0 | 29 | 1 | 4A | 0 | 29 | 1 |
| 640 | 4C | 0 | 29 | 1 | 4D | 0 | 29 | 1 | 4E | 0 | 29 | 1 | 4F | 0 | 29 | 1 |
| 650 | 52 | 0 | 29 | 1 | 54 | 0 | 29 | 1 | 55 | 0 | 29 | 1 | 56 | 0 | 29 | 1 |
| 660 | 57 | 0 | 29 | 1 | 58 | 0 | 29 | 1 | 59 | 0 | 29 | 1 | 5A | 0 | 29 | 1 |
| 670 | 5D | 0 | 29 | 1 | 5E | 0 | 29 | 1 | 5F | 0 | 30 | 1 | FB | 7 | B | 8 |
| 680 | 15 | A | 11 | 8 | ED | D | 18 | E | 29 | 1 | 0 | 0 | 29 | 1 | 1 | 0 |
| 690 | 29 | 1 | 2 | 0 | 29 | 1 | 3 | 0 | 29 | 1 | 4 | 0 | 29 | 1 | 5 | 0 |
| 6A0 | A2 | 6 | 8C | DA | 5F | 1F | 2B | C0 | 8A | 5 | 50 | 8E | DA | AD | 97 | FF |
| 6B0 | 25 | B3 | 6 | 8C | DA | 5F | 1F | 8A | 5 | 47 | 8A | 25 | 50 | 8E | DA | AD |
| 6C0 | 97 | FF | 25 | C5 | 6 | 8C | C2 | 5F | 7 | 58 | AA | 8E | C2 | AD | 97 | FF |
| 6D0 | 25 | D3 | 6 | 8C | C2 | 5F | 7 | 58 | AA | 8A | C4 | AA | 8E | C2 | AD | 97 |
| 6E0 | FF | 25 | E4 | 6 | 58 | 59 | 5F | 8C | C2 | 7 | F3 | AA | 8E | C2 | AD | 97 |
| 6F0 | FF | 25 | 11 | 1 | 4B | 2 | 35 | 2 | 2 | 3 | A6 | 2 | AB | 1 | 5D | 2 |
| 700 | 40 | 2 | AB | 1 | B6 | 1 | 1E | 1 | 11 | 1 | 4B | 2 | 35 | 2 | 4 | 2 |
| 710 | 5D | 2 | F2 | 6 | 40 | 2 | D | 2 | 1E | 1 | 11 | 1 | AE | 3 | 35 | 2 |
| 720 | 35 | 2 | A0 | 6 | 5D | 2 | F2 | 6 | 40 | 2 | 40 | 2 | C3 | 6 | 1E | 1 |
| 730 | 32 | 7 | 59 | 87 | C8 | 87 | C8 | 87 | C8 | 87 | C8 | E2 | F6 | AD | 97 | FF |
| 740 | 25 | 11 | 1 | 0 | 1 | C8 | 0 | CD | 2 | 30 | 7 | 1E | 1 | 4F | 7 | 5A |
| 750 | 2B | C0 | EC | 50 | AD | 97 | FF | 25 | 5A | 7 | 5A | 58 | EE | AD | 97 | FF |
| 760 | 25 | 63 | 7 | 8B | 46 | 0 | 89 | 46 | 2 | AD | 97 | FF | 25 | 6F | 7 | 5A |
| 770 | 5F | 58 | 59 | 57 | 52 | 51 | 50 | AD | 97 | FF | 25 | 7D | 7 | 8B | FC | FF |
| 780 | 75 | 6 | FF | 75 | 4 | AD | 97 | FF | 25 | 8B | 7 | 5F | 4F | 4F | FF | 25 |
| 790 | AD | 97 | FF | 25 | 96 | 7 | FB | F4 | FA | AD | 97 | FF | 25 | 9F | 7 | B0 |
| 7A0 | 8 | E6 | 6 | 90 | B0 | 9 | E6 | 6 | AD | 97 | FF | 25 | AE | 7 | 8B | 6 |
| 7B0 | 40 | 0 | 3D | 5A | A5 | 75 | 5 | B8 | 1 | 0 | EB | 2 | 2B | C0 | 50 | AD |
| 7C0 | 97 | FF | 25 | C5 | 7 | C7 | 6 | 40 | 0 | A5 | 5A | AD | 97 | FF | 25 | AD |
| 7D0 | 97 | FF | 25 | 11 | 1 | 5D | 2 | 8 | 1 | 10 | B6 | 1 | 5D | 2 | 58 | 7 |
| 7E0 | 9D | 7 | 1E | 1 | 11 | 1 | 4B | 2 | 8 | 1 | 4 | DC | 1 | 59 | 1 | 5 |
| 7F0 | D3 | 7 | 4F | 1 | 2 | 58 | 7 | 1E | 1 | 11 | 1 | 32 | 6 | 20 | 2 | 2E |

<u>LISTING NO. 3</u>

Sheet 3

| | | | | | | | | | | | | | | | | |
|---|---|---|---|---|---|---|---|---|---|---|---|---|---|---|---|---|
| 800 | | 6 | 20 | 2 | E4 | 7 | C3 | 7 | 1E | 1 | 11 | 1 | C3 | 7 | 1E | 1 | 11 |
| 810 | | 1 | 3A | 6 | 4 | 2 | 36 | 6 | 4 | 2 | A0 | 6 | 32 | 6 | 2C | 2 | C3 |
| 820 | | 7 | 1E | 1 | 11 | 1 | B9 | 2 | 67 | 2 | 87 | 2 | 5D | 2 | 65 | 1 | 7E |
| 830 | | 2 | D | 2 | 8 | 1 | 2 | 8A | 1 | F6 | 1E | 1 | 11 | 1 | E4 | 1 | 5D |
| 840 | | 2 | E4 | 1 | DC | 1 | 1E | 1 | 11 | 1 | AE | 3 | 3B | 8 | 59 | 1 | 5 |
| 850 | | 28 | 3 | 4F | 1 | B | 67 | 2 | E4 | 1 | 59 | 1 | 2 | 5D | ? | 55 | 2 |

| Addr | Col 77 | | | | | | | Col 78 | | | | | | |
|------|----|----|----|----|----|----|----|----|----|----|----|----|----|----|
| 860 | 1E | 1 | 11 | 1 | AE | 3 | 4 | 2 | 5D | 2 | 4 | 2 | 67 | 2 | 47 | 8 |
| 870 | DC | 1 | 59 | 1 | 2 | 5D | 2 | 55 | 2 | 1E | 1 | 30 | 1 | 0 | 80 | 11 |
| 880 | 1 | 7B | 8 | 72 | 2 | 72 | 2 | 8 | 1 | 2 | CD | 2 | 67 | 2 | 87 | 2 |
| 890 | 5D | 2 | 65 | 1 | 7E | 2 | 62 | 8 | 8 | 1 | 2 | 8A | 1 | F6 | 1E | 1 |
| 8A0 | A2 | 8 | 59 | 5F | 5A | 53 | 55 | 56 | 8B | F2 | BB | 0 | 0 | 8B | EB | AD |
| 8B0 | F7 | 2D | 83 | C7 | 2 | 3 | D8 | 13 | EA | E2 | F4 | 8B | C3 | 8B | CD | 5E |
| 8C0 | 5D | 5B | 50 | 51 | AD | 97 | FF | 25 | 11 | 1 | FC | 3 | 4 | 2 | 8 | 1 |
| 8D0 | 0 | 65 | 1 | 8 | 1 | 74 | 1 | | FA | 0 | 1 | A | 4 | FC | 3 | 4 |
| 8E0 | 2 | 23 | 8 | FC | 3 | 4 | 2 | 4B | 2 | 4 | 4 | D | 2 | C3 | 2 | B9 |
| 8F0 | 2 | 0 | 4 | D | 2 | 1E | 1 | 11 | 1 | 0 | 4 | 4 | 2 | 92 | 2 | 0 |
| 900 | 1 | A | 4 | FC | 3 | 4 | 2 | A0 | 8 | 4 | 4 | 4 | 2 | 72 | 3 | 1E |
| 910 | 1 | 11 | 1 | FC | 3 | 4 | 2 | C3 | 2 | B9 | 2 | 0 | 4 | D | 2 | 35 |
| 920 | 2 | 5D | 2 | 40 | 2 | B9 | 2 | 8 | 1 | 0 | 65 | 1 | AE | 3 | 7E | 2 |
| 930 | 87 | 2 | F7 | 8 | 5D | 2 | 7E | 2 | 87 | 2 | D | 2 | 8 | 1 | 2 | 8A |
| 940 | 1 | EA | BB | 3 | 1E | 1 | 11 | 1 | A6 | 2 | B9 | 2 | 67 | 2 | 87 | 2 |
| 950 | 5D | 2 | 65 | 1 | 7E | 2 | AF | 2 | 4 | 2 | 7E | 2 | 4 | 2 | 92 | 2 |
| 960 | 7E | 2 | D | 2 | 8 | 1 | 2 | 8A | 1 | EA | 1E | 1 | 6E | 9 | 6 | 1E |
| 970 | 56 | 53 | 8E | 6 | CE | 3 | 2B | F6 | BB | 0 | 0 | 2B | D2 | B9 | 0 | 8 |
| 980 | 8E | 1E | D2 | 3 | 2B | C0 | 26 | AC | D7 | 3 | D0 | E2 | F9 | 5B | 5E | 1F |
| 990 | 7 | 52 | AD | 97 | FF | 25 | 11 | 1 | 94 | 7 | 8 | 1 | F | 41 | 7 | 0 |
| 9A0 | 1 | 0 | 1 | 8 | 1 | 0 | 65 | 1 | 7E | 2 | 8 | 1 | 2 | 58 | 7 | 8 |
| 9B0 | 1 | 2 | 8 | 1 | 4 | D3 | 7 | 8 | 1 | 1 | 8 | 1 | 4 | D3 | 7 | 8 |
| 9C0 | 1 | 2 | 41 | 7 | 94 | 7 | 6C | 9 | 1C | 4 | 7E | 2 | B9 | 2 | 87 | 2 |
| 9D0 | D | 2 | 74 | 1 | D3 | 1E | 1 | 11 | 1 | C8 | 8 | 1C | 4 | 0 | 4 | 4 |
| 9E0 | 2 | 87 | 2 | 1C | 4 | 0 | 1 | 0 | 1 | 0 | 4 | 4 | 2 | 92 | 2 | 11 |
| 9F0 | 9 | 1C | 4 | 0 | 1 | 0 | 1 | 0 | 4 | 4 | 2 | 92 | 2 | AE | 3 | 46 |
| A00 | 9 | A6 | 2 | 7F | 8 | 0 | 4 | 4 | 2 | 87 | 2 | 1C | 4 | 92 | 2 | C3 |
| A10 | 2 | 1E | 1 | 11 | 1 | 96 | 9 | D7 | 9 | 8 | 1 | 8 | 87 | 2 | 4B | 2 |
| A20 | 8 | 1 | 2 | 58 | 7 | 8 | 1 | 2 | 8 | 1 | 4 | D3 | 7 | 4E | 6 | 2C |
| A30 | 2 | C3 | 7 | 1E | 1 | 11 | 1 | AC | 7 | 59 | 1 | E | 26 | 6 | 20 | 2 |
| A40 | B9 | 2 | 7A | 6 | 87 | 2 | 4 | 2 | 89 | 7 | 1E | 1 | 4E | A | 58 | B9 |
| A50 | 8 | 0 | 2B | D2 | 8A | 16 | 4E | 0 | 80 | FA | 0 | 75 | D | BA | 1 | 0 |
| A60 | D1 | EA | D0 | DA | 84 | C2 | E1 | FA | EB | 10 | BA | 1 | 0 | D1 | EA | D0 |
| A70 | D2 | 84 | C2 | E1 | FA | F7 | D9 | 83 | C1 | 7 | 51 | AD | 97 | FF | 25 | 81 |
| A80 | A | 5A | 59 | D1 | E1 | D1 | E1 | D1 | E1 | D1 | E1 | 2B | C0 | 8A | 6 | 4E |
| A90 | 0 | 3C | 0 | 58 | 75 | C | 2B | CA | 3A | C8 | 73 | 3 | 51 | EB | 1 | 50 |
| AA0 | EB | A | 3 | CA | 3A | C8 | 73 | 3 | 50 | EB | 1 | 51 | AD | 97 | FF | 25 |
| AB0 | B2 | A | 5F | 2B | C0 | A0 | 4E | 0 | 1E | 8E | 1E | CE | 3 | 3C | 0 | 75 |
| AC0 | 5 | BA | FF | FF | EB | 3 | BA | 1 | 0 | 8A | 5 | A | C0 | 75 | D | 2B |
| AD0 | C0 | B9 | 8 | 0 | 3 | FA | 8A | 5 | A | C0 | E1 | F8 | 1F | 57 | AD | 97 |
| AE0 | FF | 25 | 11 | 1 | 46 | 6 | 20 | 2 | E8 | 3 | 0 | 1 | FF | 0 | AB | 1 |
| AF0 | DC | 1 | 59 | 1 | F | 0 | 1 | 80 | 3C | 0 | 1 | 49 | 4 | 0 | 1 | C8 |
| B00 | 3 | 4F | 1 | C | 0 | 1 | 70 | 3C | 0 | 1 | 48 | 4 | 0 | 1 | C7 | 3 |
| B10 | 65 | 1 | 7E | 2 | B0 | A | CC | 3 | 67 | 2 | A0 | 6 | 4C | A | 7F | A |
| B20 | 8 | 1 | 40 | 8A | 1 | EC | 4B | 2 | 8 | 1 | 10 | 5A | 3 | 5D | 2 | 8 |
| B30 | 1 | 7 | AB | 1 | 1E | 1 | 11 | 1 | 72 | 2 | 87 | 2 | 4B | 2 | E4 | 1 |
| B40 | 59 | 1 | 5 | 8 | 1 | 8 | 92 | 2 | 4B | 2 | 8 | 1 | 8 | 5A | 3 | 72 |
| B50 | 2 | 87 | 2 | 5D | 2 | 8 | 1 | 8 | 30 | 3 | 1E | 1 | 5E | B | 59 | 58 |
| B60 | B | C9 | 79 | 6 | F7 | D9 | D3 | E8 | EB | 2 | D3 | E0 | 50 | AD | 97 | FF |
| B70 | 25 | 73 | B | 58 | 8A | E0 | 5F | 5A | D1 | E2 | D1 | E2 | D1 | E2 | D1 | E2 |
| B80 | B9 | 40 | 0 | 1E | 8E | 1E | CE | 3 | 3 | FA | 8A | 5 | 22 | C4 | E1 | F8 |
| B90 | 1F | 57 | AD | 97 | FF | 25 | 11 | 1 | 46 | 6 | 20 | 2 | F0 | 3 | 0 | 1 |
| BA0 | FF | 0 | AB | 1 | DC | 1 | 59 | 1 | 6 | 8 | 1 | 4F | 1 | 3 | 8 |
| BB0 | 1 | FF | E2 | A | 36 | B | 8 | 1 | 1 | 5D | 2 | 5C | B | AE | 3 | 8 |
| BC0 | 1 | 1 | 72 | 2 | 72 | 2 | 71 | B | 8 | 1 | FF | 6D | 7 | 71 | B | AE |
| BD0 | 3 | 22 | 6 | 8 | 1 | 24 | 87 | 2 | D | 2 | 22 | 6 | 8 | 1 | 26 | 87 |
| BE0 | 2 | D | 2 | 87 | 2 | 8 | 1 | 2 | D8 | 2 | 87 | 2 | 8 | 1 | 10 | 5A |
| BF0 | 3 | 1E | 1 | F5 | B | 5F | 1E | 8E | 1E | CE | 3 | BA | 10 | 0 | B9 | 40 |

LISTING NO. 3
Sheet 4

```
C00     0 B4 FF  3 FA 8A  5 3A    C4 E0 F8 1F 57 AD 97 FF
C10    25 13  C 59 8B F9 1E 8E    1E CE  3 B4 FF 8A  5 3A
C20    E0 75 1F 4F 8A  5 3A E0    75 13 83 C7  2 8A  5 3A
C30    E0 75  5 B8  0  0 EB  3    B8 11  0 EB  3 B8  F  0
C40    EB  3 B8 10  0 1F 50 AD    97 FF 25 11  1  8  1  0
C50    87  2 4B  2 11  C 4B  2    CC  1 59  1 F3 55  2 1E
C60     1 63  C 5F 2B C0 A0 4E     0 1E 8E 1E CE  3 3C  0
C70    75  C BA  1  0 81 E7 F0     7 83 C7  2 EB  9 BA FF
C80    FF 83 CF  F 83 EF  2 B4    FF B9  C  0  3 FA 8A  5
C90    3A C4 E1 F8 1F 57 AD 97    FF 25 11  1 46  6 20  2
CA0     0  1 FF  0 C1  1 46  6    2C  2 1E  1 11  1 61  C
CB0    B0  A CC  3 67  2 A0  6    4C  A 5D  2  8  1  F AB
CC0     1  8  1  8 CD  2 87  2    1E  1 11  1  0  1  8  4
CD0    F3  B 4B  C 4B  2 22  6     8  1 2C 87  2  D  2  8
CE0     1 40 92  2 4B  2 9A  C    AC  C 9A  C 5D  2 AC  C
CF0    AE  3 22  6  8  1 2A 87     2  D  2 22  6  8  1 28
D00    87  2  D  2 87  2  8  1     2 D8  2 87  2 1E  1 11
D10     1 42  6 20  2 87  2  8     1  2 E4  7  8  1 20  8
D20     1  4 E4  7 3E  6 20  2    87  2  8  1  2 E4  7  8
D30     1  B  8  1  4 E4  7 1E     1 11  1 76  6  8  7 76
D40     6 20  2  8  1  2 E4  7     8  1 2B  8  1  4 E4  7
D50    1E  1 11  1  0  1 FF  0    C1  1  0  1 80  0 39  D
D60    1E  1 11  1 AE  3 D8  3    F4  1 5D  2 D4  3 F4  1
D70    B6  1 72  2 72  2 E0  3    FC  1 5D  2 DC  3 FC  1
D80    B6  1 B6  1 CC  1 1E  1    11  1  8  1  1  8  1  4
D90    E4  7 94  7  8  1  2 41     7 94  7 96  B CA  C 5D
DA0     2 AE  3 22  6  8  1 22    87  2  D  2 22  6  8  1
DB0    20 87  2  D  2 1E  1 11     1 88  D 4A  6 20  2 59
DC0     1 25 AE  3 62  D 59  1    19 F8  3  4  2 CC  1 59
DD0     1  B EC  3 52  D  8  1    FF F8  3  D  2  F  D 4F
DE0     1  2 BB  3 4F  1  2 BB     3 1E  1 11  1 C3  7  8
DF0     1  0 F8  3  D  2 E4  3    2A  6 2C  2 B7  D 35  A
E00     8  1  1 41  7 35  A 2A     6 20  2 CC  1 59  1 EC
E10    E4  3 52  D 1E  1 11  1    EC  3 2A  6 2C  2 C3  7
E20    1E  1 CF  0  1  0  0 C4     3  8  1  4 87  2  8  1
E30    3C E6  2 35  A  8  1  0    59  1 F8 1E  1
```

We claim:

1. Apparatus for examining the ocular fundus of an eye comprising:
  (a) illuminating means for illuminating the ocular fundus, said illuminating means including aperture means having the form of non-overlapping apertures positioned substantially side by side and image forming means for forming an image of said aperture means on a part of the ocular fundus;
  (b) imaging means, responsive to reflections from said illuminated ocular fundus, for forming an image of the ocular fundus at a detecting plane, said imaging means including stereo means for providing a stereo pair of images of the ocular fundus at said detecting plane;
  (c) detecting means for detecting an image of the ocular fundus appearing at said detecting plane; and
  (d) electronic data processing means connected to said connecting means for electronically processing and digitally analyzing said image thereby to display information about the ocular fundus under examination.

2. Apparatus according to claim 1 wherein said means for illuminating comprises means for filtering the light.

3. Apparatus according to claim 2 wherein said means for filtering comprises a plurality of filters being selectable to filter the light at different wavelengths.

4. Apparatus according to claim 3 wherein said data processing means comprises means for controlling said filtering means to select any one of the plurality of filters.

5. Apparatus according to claim 1 wherein said imaging means comprises means for producing an image of the ocular fundus at the detecting plane having indicia means from which three-dimensional information may be determined by said data processing means.

6. Apparatus according to claim 1 wherein said means for providing a stereo pair comprises:
  (a) means for imaging the pupil of the eye at an imaging plane;
  (b) means for providing a pair of apertures at the imaging plane, each of the apertures transmitting light therethrough; and (c) means for spatially separating the light being transmitted through one of the apertures relative to the light being transmitted through the other of the apertures.

7. Apparatus according to claim 6 wherein said means for spatially separating comprises a biprism.

8. Apparatus according to claim 5 wherein said aperture is an array of slits.

9. Apparatus according to claim 5 wherein said detecting means has distortion, and further comprising means for producing calibration data at the detecting plane to correct for the distortion.

10. Apparatus according to claim 9 wherein said means for producing calibration data comprises:
  (a) aperture means for providing at least one aperture in the optical path of said imaging means;
  (b) means for illuminating said aperture means; and
  (c) means for imaging said at least one aperture at the detecting plane.

11. Apparatus according to claim 3 wherein said detecting means has different sensitivity to light at different wavelengths, and further comprising means for providing optical sensitivity data at the detecting plane to correct for the different sensitivity.

12. Apparatus according to claim 1 wherein said data processing means stores a plurality of images of the ocular fundus which are detected by said detecting means.

13. Apparatus according to claim 12 wherein said data processing means includes means for registering two or more of the plurality of images with one another.

14. Apparatus according to claim 13 wherein said means for registering comprises:
  (a) a display;
  (b) means for simultaneously displaying two of the plurality of images on said display; and
  (c) means for moving one of the displayed images relative to the other.

15. Apparatus according to claim 14 wherein said means for registering further comprises means for determining and storing the amount and direction of movement of the one simultaneously displayed image relative to the other.

16. Apparatus according to claim 13 further comprising:
  (a) means for determining the intensity of each two corresponding picture elements of the registered images;
  (b) means for determining a difference in intensity between each two corresponding picture elements; and
  (c) means for displaying a difference image representing the difference in intensity.

17. Apparatus according to claim 13 further comprising:
  (a) means for determining the intensity of each two corresponding picture elements of the registered images;
  (b) means for determining a ratio of intensities of each two corresponding picture elements; and
  (c) means for displaying a ratio image representing the ratio.

18. Apparatus according to claim 1 wherein said data processing means comprises means for determining the distance between any corresponding features in the stereo pair of images.

19. Apparatus according to claim 18 wherein said data processing means further comprises means, connected to said determining means, for displaying three-dimensional information of a region of the ocular fundus.

20. Apparatus according to claim 19 wherein the three-dimensional information is a depth-profile map.

21. Apparatus according to claim 1, wherein said imaging means has an optical axis, at least part of which is common with the optical axis of said illuminating means, and including automatic aligning means for detecting pupil position and for automatically aligning the eye relative to said optical axis.

22. An apparatus according to claim 1, wherein the aperture means together with the image-forming means and the imaging means together with the stereo means are operable to produce relatively dark areas between relatively light illuminated areas which, in turn, provides an increased contrast as well as improved contrast resolution and depth analysis of the fundus of the examined eye.

23. Apparatus for examining the ocular fundus of an eye comprising:
  (a) illuminating means having an optical axis for illuminating the ocular fundus;
  (b) imaging means, responsive to reflections from said illuminated ocular fundus, for forming an image of the ocular fundus at a detecting plane, said imaging means having an optical axis, at least a part of which is common with the optical axis of said illuminating means, said imaging means further including automatic aligning means for detecting pupil position and automatically aligning the eye relative to said optical axis;
  (c) detecting means for detecting an image of the ocular fundus appearing at said detecting plane; and
  (d) electronic data processing means connected to said detecting means for electronically processing and digitally analyzing said image thereby to display information about the ocular fundus under examination.

24. An apparatus according to claim 23, wherein the aperture means together with the image-forming means and the imaging means together the stereo means are operable to produce relatively dark areas between relatively light illuminated areas which, in turn, provides an increased contrast as well as improved contrast resolution and depth analysis of the fundus of the examined eye.

* * * * *